US005663300A

United States Patent [19]
Suzuki

[11] Patent Number: 5,663,300
[45] Date of Patent: Sep. 2, 1997

[54] PROTOCADHERIN-42

[75] Inventor: Shintaro Suzuki, Torrance, Calif.

[73] Assignee: Doheny Eye Institute, Los Angeles, Calif.

[21] Appl. No.: 453,274

[22] Filed: May 30, 1995

Related U.S. Application Data

[62] Division of Ser. No. 998,003, Dec. 29, 1992.
[51] Int. Cl.$^6$ ............................................ C07K 14/705
[52] U.S. Cl. ............................................ 530/350; 530/395
[58] Field of Search ........................................ 530/350, 395

[56] References Cited

PUBLICATIONS

Amagai et al., "Autoantibodies against a Novel Epithelial Cadherin in Pemphigus Vulgaris, a Disease of Cell Adhesion", Cell, 67: 869–877 (Nov. 29, 1991).
Angerer et al., "Demonstration of Tissue–Specific Gene Expression by in situ Hybridization", Methods in Enzymology, 152: 649–660 (1987).
Ausubel et al., Eds., Current Protocols in Molecular Biology, Sections 6.6.1–6.1.4, 6.2.1–6.2.3, John Wiley & Sons, New York (1987).
Chen et al., "Cell–Cell Contacts Mediated by E–Cadherin (Uvomorulin) Restrict Invasive behavior of L–Cells", J. Cell Biol., 114(2):319–327 (Jul. 1991).
Detrick et al., "The Effects of N–Cadherin Misexpression on Morphogenesis in Xenopus Embryos", Neuron, 4: 493–506 (Apr. 1990).
Donalies et al., "Expression of M–cadherin, a Member of the Cadherin Multigene Family, Correlates with Differentiation of Skeletal Muscle Cells", PNAS, USA, 88:8024–8028 (Sep. 1991).
Frixen et al., "E–Cadherin–Mediated Cell–Cell Adhesion Prevents Invasiveness of Human Carcinoma Cells", J. Cell Biol., 113(1): 173–185 (Apr. 1991).
Fujimori et al., "Ecotopic Expression of N–cadherin Perturbs Histogenesis in Xenopus Embryos", Development, 110:97–103 (1990).
Gallin et al., "Sequence Analysis of a cDNA Clone Encoding the Liver Cell Adhesion Molecule, L–CAM", PNAS, USA, 84: 2808–2812 (May 1987).
Goodwin et al., "Desmoglein Shows Extensive Homology to the Cadherin Family of Cell Adhesion Molecules", Biochem. Biophys. Res. Commun., 173(3): 1224–1230 (Dec. 31, 1990).
Hatta et al., "Cloning and Expression of cDNA Encoding a Neural Calcium–dependent Cell Adhesion Molecule: Its Identity in the Cadherin Gene Family", J. Cell Biol., 106: 873–881 (Mar. 1988).
Holton et al., "Desmosomal Glycoproteins 2 and 3 (desmocollins) Show N Terminal Similarity to Calcium–Dependent Cell–Cell Adhesion Molecules", J. Cell. Science, 97:239–246 (1990).
Inuzuka et al., "R–Cadherin: A Novel Ca$^{2+}$–Dependent Cell–Cell Adhesion Molecule Expressed in the Retina", Neuron, 7: 69–71 (1991).

Kenneth, "Cell Fusion ", Methods in Enzymol, 58:345–359 (1978).
Kintner et al., "Regulation of Embryonic Cell Adhesion by the Cadherin Cytoplasmic Domain", Cell, 69:225–236 (Apr. 17, 1992).
Koch et al., "Identification of Desmoglein, a Constitutive Desmosomal Glycoprotein, as a member of the Cadherin Family of Cell Adhesion Molecules", Eur. J. Cell Biol, 53: 1–12 (1990).
Liaw et al., "Identification and Cloning of Two Species of Cadherins in Bovine ENdothelial Cells", EMBO J., 9(9): 2701–2708 (1990).
Mahoney et al., "The fat Tumor Suppressor Gene in Drosophila Encodes a Novel Member of the Cadherin Gene Superfamily", Cell, 67: 853–868 (Nov. 29, 1991).
Maniatis et al., Molecular Cloning: A Laboratory Manual, Cold Spring Harbor, New York: Cold Spring Harbor Laboratory, p. 196 (1982).
Maruyama et al., "Detection of Calcium Binding Proteins by $^{45}$Ca Autoradiography on Nitrocellulose Membrane after Sodium Dodecyl Sulfate Gel Electrophoresis$^1$ ", J. Biochem., 95: 511–519 (1984).
Matsunaga et al., "Guidance of Optic Nerve Fibers by N–cadherin Adhesion Molecules ", Nature, 334: 62–64 (Jul. 1988).
Miyatani et al., "Neural Cadherin: Role in Selective Cell–Cell Adhesion", Science, 245: 631–635 (Aug. 1989).
Nagafuchi et al., "Transformation of Cell Adhesion Properties by Exogenously Introduced E–cadherin cDNA ", Nature , 329: 341–343 (Sep. 1987).
Napolitano et al., "Molecular Cloning and Characterization of B–Cadherin, a Novel Chick Cadherin", J. Cell Biol., 113(4): 893–905 (May 1991).
Nose et al., "Isolation of Placental Cadherin cDNA: Identification of a Novel Gene Family of Cell–Cell Adhesion Molecules", EMBO J., 6(12):3655–3661 (1987).
Porter et al., "Dystrophin Colocalizes with β–Spectrin in Distinct Subsarcolemmal Domains in Mammalian Skeletal Muscle", J. Cell. Biol., 117(5): 997–1005 (Jun. 1992).
Ranscht et al., "T–Cadherin, a Novel Cadherin Cell Adhesion Mol. in the Nervous System Lacks the Conserved Cytoplasmic Region", Neuron, 7: 391–402 (Sep. 1991).
Ringwald et al., "The Structure of Cell–Adhesion Molecule Uvomorulin. Insights into the Molecular Mechanism of Ca$^{2+}$–Dependent Cell Adhesion", EMBO J., 6(12): 3647–3653 (1987).

(List continued on next page.)

*Primary Examiner*—Stephen Walsh
*Assistant Examiner*—Karen E. Brown
*Attorney, Agent, or Firm*—Marshall, O'Toole, Gerstein, Murray & Borun

[57] ABSTRACT

Polynucleotide sequences encoding novel cadherin-related polypeptides, designated protocadherins, and variants thereof are provided by the invention as well as methods and materials for the recombinant production of the same. Antibody substances specific for protocadherins are also disclosed as useful for modulating the natural binding and/or regulatory activities of the protocadherins.

3 Claims, 3 Drawing Sheets

PUBLICATIONS

Shimoyama et al., "Molecular Cloning of a Human $Ca^{2+}$-Dependent Cell-Cell Adhesion Molecule Homologous to Mouse Placental Cadherin: Its Low Expression in Human Placental Tissues", *J. Cell Biol.*, 109: 1787–1794 (Oct. 1989).

Suzuki et al., "Diversity of the Cadherin Family: Evidence for Eight New Cadherins in Nervous Tissue", *Cell Regulation*, 2: 261–270 (Apr. 1991).

Suzuki et al., "Evidence for Cadherin Superfamily, " *Cell. Struc. Func.*, 16: 605 (Nov. 23, 1991).

Suzuki et al., "Evidence for Cadherin Superfamily", *J. Cell. Biol.*, 115: 72a (Abstract 416) (Dec. 9, 1991).

Takeichi, "Cadherin Cell Adhesion Receptors as a Morphogenetic Regulator", *Science*, 251: 1451–1455 (Mar. 1991).

Takeichi, "Cadherins: A Molecular Family Important in Selective Cell–Cell Adhesion", *Annu. Rev. Biochem.*, 59: 237–252 (1990).

Thomas, "Hybridization of Denatured RNA and Small DNA Fragments Transferred to Nitrocellulose", *PNAS, USA*, 77(9): 5201–5205 (Sep. 1980).

Towbin et al., "Electrophoretic Transfer of Proteins from Polyacrylamide Gels to Nitrocellulose Sheets: Procedure and Some Applications", *PNAS*, 76: 4350–4354 (Sep. 1979).

Urushihara et al., "Immunological Detection of Cell Surface Components Related with Aggregation of Chinese Hamster and Chick Embryonic Cells", *Dev. Biol.*, 70: 206–216 (1979).

Vanderbark et al., "Experimental Allergic Encephalomyelitis and Cellular Immunity in the Lewis Rat", *Cell Immunol.*, 12: 85–93 (1974).

Vleminckx et al., "Genetic Manipulation of E-Cadherin Expression by Epithelial Tumor Cells Reveals an Invasion Suppressor Role", *Cell*, 66: 107–119 (Jul. 12, 1991).

FIGURE 1A

```
PC43  EC 1   ASTVIHYEIPEEREK------GFAVGNVVANL---GLDLGSLSA--
      EC 2   PTQEMKLEISEAVAP------GTRFPLESAH----DPDLGSNSL--
      EC 3   NQSLYRARVPGGCTS------GTRVQVLAT-----DLDEGPNGE--
      EC 4   TVTSVYSPVPEDAS-------GTVIALLSVT----DLDAGENGL--
      EC 5   SQSSYDVYIEENNLP------GAPILNLSVW----DPDAPQNAR--
      EC 6   LYPRPGGSSVEMLPRGTSA--GHLVSRVVGW----DADAGHNAW--

PC42  EC 1   VPEEQPPNTLI----------GSL-----------AADYGFPDVG-
      EC 2   ASPVITLAIPENTNI------GSLFPIPLAS----DRDAGPNGV--
      EC 3   ERPSYEAELSENSPI------GHSVIQVKAN----DSDQGANAE--
      EC 4   EIRGIGLVTHQDGMANISEDVAEETAVALVQVSDRDEGENAA--
      EC 5   TQSVTEVAFPENNKP------GEVIAEITAS----DADSGSNAE--
      EC 6   MLSGYNFSVMENMPA------LSPVGMVTVI----DGDKGENAQ--
      EC 7   TAPSNTSHKLLTPQTRL----GETVSQVAAE----DFDSGVNAE--

FAT   EC18   EDTVYSFDIPENAQR------GYQVGQIVAR----DADLGQNAQ--

N-CAD EC 1   DWVIPPINLPENSRG------PFPQELVRIRS---DRDKNLSLRYT
      EC 2   LHQVWNGTVPEGSKP------GTYVMTVTAI----DADDPNALNGM
      EC 3   TAMTFYGEVPENRVD------IIVANLTVT-----DKDQPHTPAWN
      EC 4   APNPKIIRQEEGLHA------GTMLTTFTAG----DPDRYMQQN--
      EC 5   LPQEAETCETPDPNSINITTAL-------------DYDIDPNAGP--

MOTIF        *****o****v*En****----GT*v***v*A*---D*D*G*N**--
```

```
PC43  EC 1   RRFPVVSGASRR------FFEVNRET----GEMFVNDR----
      EC 2   QTYELSRNEY--------FALRVQTREDSTKYAELVLERA--
      EC 3   IIYSFGSHNRAGVRQL--FALDLVT----GMLTIKGR-----
      EC 4   VTCEVPPGLP--------FSLTSSLKNYFTLKTSAD------
      EC 5   LSFFLLEQGAETGLVGRYFTINRDN----GIVSSLVP-----
      EC 6   LSYSLFGSPNQSL-----FAIGLHT----GQISTARPV----

PC42  EC 1   HLYKLEVGAP--------YLRVDGKT----GDIFTTETS---
      EC 2   ASYELQVAED--------QEEKQPQLIVMGN-----------
      EC 3   IEYTFHQAPEVVRRL---LRLDRNT----GLITVQGP-----
      EC 4   VTCVVAGDVP--------FQLRQASETGSDSKKKYFLQTTTP
      EC 5   LVYSLEPEPAAKGL----FTISPET----GEIQVKTS-----
      EC 6   VQLSVEQDNGD-------FVIQNGT----GTILSSLS-----
      EC 7   LIYSIAGGNPYGL-----FQIGSHS-----GAITLEKE----

FAT   EC18   LSYGVVSDWANDV-----FSLNPQT-----GMLTLTAR----

N-CAD EC 1   VTGPGADQPPTGI-----FIINPIS----GQLSVTKP-----
      EC 2   LRYRIVSQAPSTPSPNM-FTINNET----GDIIVAAG-----
      EC 3   AVYRISGGDPTGR-----FAIQTDPNSND-GLVTVVKP----
      EC 4   IRYTKLSDPAN-------WLKIDPVN---GQITTIAV-----
      EC 5   FAFDLPLSPVTIKRN---WTITRLN----GDFAQLNLK----

MOTIF        I*o*I************o*I****T-----G*I*T****---
```

FIGURE 1B

```
PC43    EC 1    LDRLELCGTLPSCTVTLELVVENP------------------LELFSVEVVIQDINDNNPAF
        EC 2    LDREREPSLQLVLTALDGGTPAL-------------------SASLPIHIKVLDANDNAPVF
        EC 3    LDFEDTKLHEIYIQAKDKGANPE-------------------GAHCKVLVEVVDVNDNAPEI
        EC 4    LDRETVPEYNLSITARDAGTPSL-------------------SALTIVRVQVSDINDNPPQS
        EC 5    LDYEDRREFELTAHISDGGTPVL-------------------ATNISVNIFVTDRNDNAPQV
        EC 6    QDTDSPRQTLTVL-IKDNGEPSLSTTATLTVSVTEDSPEARAEFPSGSAPREQKKN

PC42    EC 1    IDREGLRECONQLPGDPCILEFEVSITDLVQNAS--PRLLEGQIEVQDINDNTPNF
        EC 2    LDRERWDSYDLTIKVQDGGSPPR-------------------ATSALLRVTVLDTNDNAPKF
        EC 3    VDREDLSTLRFSVLAKDRGTNPK-------------------SARAQVVVTVKDMNDNAPTI
        EC 4    LDYEKVKDYTIEIVAVDSGNPPL-------------------SSTNSLKVQVVDVNDNAPVF
        EC 5    LDREQRESYELKVVAADRGSPSL-------------------QGTATVLVNVLDCNDNDPKF
        EC 6    FDREQQSTYTFQLKAVDGGVPPR-------------------SAYVGTINVLDENDNAPYI
        EC 7    IERRHHGLHRLVVKVSDRGKPPRYGTALVHLYVNETLANRTLLETLGHSLDTPLD
                                                          IDIAGDPEYERSKQRGN

FAT     EC18    LDYEEVQHYILIVQAQDNGQPSL-------------------STTITVYCNVLDLNDNAPIF

N-CAD   EC 1    LDREQIARFHLRAHAVDINGNQV-------------------ENPIDIVINVIDMNDNRPEF
        EC 2    LDRENVQQYTLIIQATDMEGIPTYGL----------------SNTATAVITVTDVNDNPPEF
        EC 3    IDFETNRMFVLTVAAENQVPLAKGIQHPP-------------QSTATVSVTVIDVNE-NPYF
        EC 4    LDRESPNVKNNIYNATFLASDNGIPPM---------------SGTGTLQIYLLDINDNAPQV
        EC 5    IKFLEAGIYEVPIIITDSGNPPKSNIS---------------ILRVRVCQCDFNGDCTDVDR

MOTIF           LDRE*****o*L*v*A*D*G*P**------------------**t*TV*v*V*D*NDNAP*F
```

FIGURE 1C

PROTOCADHERIN-42

This is a Rule 60 Divisional of U.S. patent application Ser. No. 07/998,003, filed Dec. 29, 1992.

FIELD OF THE INVENTION

The present invention relates, in general, to materials and methods relevant to cell-cell adhesion. More particularly, the invention relates to novel adhesion proteins, designated protocadherins, and to polynucleotide sequences encoding the protocadherins. The invention also relates to methods for inhibiting binding of the protocadherins to their natural ligands/antiligands.

BACKGROUND

In vivo, intercellular adhesion plays an important role in a wide range of events including morphogenesis and organ formation, leukocyte extravasation, tumor metastasis and invasion, and the formation of cell junctions. Additionally, cell-cell adhesion is crucial for the maintenance of tissue integrity.

Intercellular adhesion is mediated by specific cell surface adhesion molecules. Cell adhesion molecules have been classified into at least four families including the immunoglobulin superfamily, the integrin superfamily, the selectin family and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain (the N-terminal 113 amino acids of the domain appear to be directly involved in binding) consisting of five subdomains characterized by sequences unique to cadherins, a hydrophobic membrane-spanning domain and a C-terminal cytoplasmic domain that interacts with the cytoskeleton through catenins and other cytoskeleton-associated proteins. Some cadherins lack a cytoplasmic domain, however, and appear to function in cell-cell adhesion by a different mechanism than cadherins having a cytoplasmic domain. The cytoplasmic domain is required for the adhesive function of the extracellular domain in cadherins that do have an cytoplasmic domain. Binding between members of the cadherin family expressed on different cells is homophilic (i.e., a member of the cadherin family binds to cadherins of its own or a closely related subclass) and $Ca^{2+}$-dependent. For recent reviews on cadherins, see Takeichi, *Annu. Rev. Biochem.*, 59:237–252 (1990) and Takeichi, *Science*, 251:1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvement in $Ca^{2+}$-dependent cell adhesion and their unique immunological characteristics and tissue localization. With the later immunological identification of N-cadherin, which was found to have a different tissue distribution than E-cadherin, it became apparent that a new family of $Ca^{2+}$-dependent cell-cell adhesion molecules had been discovered.

The molecular cloning of the genes encoding E-cadherin [see Nagafuchi et al., *Nature*, 329:341–343 (1987)], N-cadherin [Hatta et al., *J. Cell. Biol.*, 106:873–881 (1988)], and P-cadherin [Nose et al., *EMBO J.*, 6:3655–3661 (1987)] provided structural evidence that the cadherins comprised a family of cell adhesion molecules. Cloning of L-CAM [Gallin et al., *Proc. Natl. Acad. Sci. USA*, 84:2808–2812 (1987)] and uvomorulin [Ringwald et al., *EMBO J.*, 6:3647–3653 (1986)] revealed that they were identical to E-cadherin. Comparisons of the amino acid sequences of E-, N-, and P-cadherins showed a level of amino acid similarity of about 45%–58% among the three subclasses. Liaw et al., *EMBO J.*, 9:2701–2708 (1990) describes the use of PCR with degenerate oligonucleotides based on conserved regions of the E-, N- and P-cadherins to amplify N- and P-cadherin from a bovine microvascular endothelial cell cDNA.

The isolation by PCR of eight additional cadherins was reported in Suzuki et al., *Cell Regulation*, 2:261–270 (1991). Subsequently, several other cadherins were described including R-cadherin [Inuzuka et al., *Neuron*, 7:69–79 (1991)], M-cadherin [Donalies, *Proc. Natl. Acad. Sci. USA*, 88:8024–8028 (1991)], B-cadherin [Napolitano, *J. Cell. Biol.*, 113:893–905 (1991)] and T-cadherin [Ranscht, *Neuron*, 7:391–402 (1991)].

Additionally, proteins distantly related to cadherins such as desmoglein [Goodwin et. al., *Biochem. Biophys. Res. Commun.*, 173:1224–1230 (1990) and Koch et al., *Eur. J. Cell Biol.*, 53:1–12 (1990)] and the desmocollins [Holton et al., *J. Cell Science*, 97:239–246 (1990)] have been described. The extracellular domains of these molecules are structurally related to the extracellular domains of typical cadherins, but each has a unique cytoplasmic domain. Mahoney et al., *Cell*, 67:853–868 (1991) describes a tumor suppressor gene of *Drosophila*, called *fat*, that also encodes a cadherin-related protein. The *fat* tumor suppressor comprises 34 cadherin-like subdomains followed by four. EGF-like repeats, a transmembrane domain, and a novel cytoplasmic domain. The identification of these cadherin-related proteins is evidence that a large superfamily characterized by a cadherin extracellular domain motif exists.

Studies of the tissue expression of the various cadherin-related proteins reveal that each subclass of molecule has a unique tissue distribution pattern. For example, E-cadherin is found in epithelial cells while N-cadherin is found in neural and muscle cells. Expression of cadherin-related proteins also appears to be spatially and temporally regulated during development because individual proteins appear to be expressed by specific cells and tissues at specific developmental stages [for review see Takeichi (1991), supra]. Both the ectopic expression of cadherin-related proteins and the inhibition of native expression of cadherin-related proteins hinders the formation of normal tissue structure [Detrick et al., *Neuron*, 4:493–506 (1990); Fujimori et al., *Development*, 110:97–104 (1990); Kintner, *Cell*, 69:225–236 (1992)].

The unique temporal and tissue expression pattern of the different cadherins and cadherin-related proteins is particularly significant when the role each subclass of proteins may play in vivo in normal events (e.g., the maintenance of the intestinal epithelial barrier) and in abnormal events (e.g., tumor metastasis or inflammation) is considered. Different subclasses or combinations of subclasses of cadherin-related proteins are likely to be responsible for different cell-cell adhesion events in which therapeutic detection and/or intervention may be desirable. For example, auto-antibodies from patients with pemphigus vulgaris, an autoimmune skin disease characterized by blister formation caused by loss of cell adhesion, react with a cadherin-related protein offering direct support for adhesion function of cadherins in vivo [Amagai et al., *Cell*, 67:869–877 (1991)]. Studies have also suggested that cadherins and cadherin-related proteins may have regulatory functions in addition to adhesive activity. Matsunaga et al., *Nature*, 334:62–64 (1988) reports that N-cadherin has neurite outgrowth promoting activity. The *Drosophila fat* tumor supressor gene appears to regulate cell growth and supress tumor invasion as does mammalian E-cadherin [see Mahoney et al., supra; Frixen et al., *J. Cell. Biol.*, 113:173–185 (1991); Chen et al., *J. Cell, Biol.*, 114:319–327 (1991); and Vleminckx et al., *Cell*, 66:107–119 (1991)]. Thus, therapeutic intervention in the regulatory activities of cadherin-related proteins expressed in specific tissues may be desirable.

There thus continues to exist a need in the art for the identification and characterization of additional cadherin-related proteins which participate in cell-cell adhesion and/ or regulatory events. Moreover, to the extent that cadherin-related proteins might form the basis for the development of therapeutic and diagnostic agents, it is essential that the genes encoding the proteins be cloned. Information about the DNA sequences and amino acid sequences encoding the cadherin-related proteins would provide for the large scale production of the proteins by recombinant techniques and for the identification of the tissues/cells naturally producing the proteins. Such sequence information would also permit the preparation of antibody substances or other novel binding molecules specifically reactive with the cadherin-related proteins that may be useful in modulating the natural ligand/ antiligand binding reactions in which the proteins are involved.

SUMMARY OF THE INVENTION

The present invention provides cadherin-related materials and methods that are relevant to cell-cell adhesion. In one of its aspects, the present invention provides purified and isolated polynucleotide sequences (e.g., DNA and RNA, both sense and antisense strands) encoding the novel cell adhesion molecules designated herein as protocadherins, including protocadherin-42 and protocadherin-43. Preferred polynucleotide sequences of the invention include genomic and cDNA sequences as well as wholly or partially synthesized DNA sequences, and biological replicas thereof. Biologically active vectors comprising the polynucleotide sequences are also contemplated.

Specifically illustrating protocadherin polynucleotide sequences of the present invention are the inserts in the plasmids pRC/RSV-pc42 and pRC/RSV-pc43 which were deposited with the American Type Culture Collection (ATCC), 12301 Parklawn Drive, Rockville, Md. 20852 on Dec. 16, 1992 and were assigned ATCC Accession Nos. 69162 and 69163, respectively.

The scientific value of the information contributed through the disclosures of the DNA and amino acid sequences of the present invention is manifest. For example, knowledge of the sequence of a partial or complete DNA encoding a protocadherin makes possible the isolation by DNA/DNA hybridization of full length cDNA or genomic DNA sequences that encode the protein and, in the case of genomic DNA sequences, that specify protocadherin-specific regulatory sequences such as promoters, enhancers and the like. DNA/DNA hybridization procedures utilizing the DNA sequences of the present invention also allow the isolation of DNAs encoding heterologous species proteins homologous to the protocadherins specifically illustrated herein.

According to another aspect of the invention, host cells, especially eucaryotic and procaryotic cells, are stably transformed or transfected with the polynucleotide sequences of the invention in a manner allowing the expression of protocadherin polypeptides in the cells. Host cells expressing protocadherin polypeptide products, when grown in a suitable culture medium, are particularly useful for the large scale production of protocadherin polypeptides, fragments and variants thereby enabling the isolation of the desired polypeptide products from the cells or from the medium in which the cells are grown.

The novel protocadherin protein products of the invention may be obtained as isolates from natural tissue sources, but are preferably produced by recombinant procedures involving the host cells of the invention. The products may be obtained in fully or partially glycosylated, partially or wholly de-glycosylated, or non-glycosylated forms depending on the host cell selected or recombinant production and/or post-isolation processing.

Protocadherin variants according to the invention may comprise polypeptide analogs wherein one or more of the specified amino acids is deleted or replaced or wherein one or more non-naturally encoded amino acids are added: (1) without loss, and preferably with enhancement, of one or more of the biological activities or immunological characteristics specific for a protocadherin; or (2) with specific disablement of a particular ligand/antiligand binding function.

Also contemplated by the present invention are antibody substances (e.g., monoclonal and polyclonal antibodies, chimeric and humanized antibodies, antibody domains including Fab, Fab', $F(ab')_2$, Fv or single variable domains, and single chain antibodies) which are specific for the protocadherins of the invention. Antibody substances can be developed using isolated natural, recombinant or synthetic protocadherin polypeptide products or host cells expressing such products on their surfaces. The antibody substances may be utilized for purifying protocadherin polypeptides of the invention, for determining tissue expression of polypeptides and as antagonists of the ligand/antiligand binding activities of the protocadherins. Specifically illustrating monoclonal antibodies of the present invention are the protocadherin-43 specific monoclonal antibodies produced by the hybridoma cell line designated 38I2C which was deposited with the ATCC on Dec. 2, 1992 and was assigned ATCC Accession No. HB 11207.

Numerous other aspects and advantages of the present invention will be apparent upon consideration of the following detailed description, reference being made to the drawings wherein FIG. 1A–C is an alignment of protocadherin amino acid sequences of the invention with the amino acid sequences of N-cadherin and of the *Drosophila fat* tumor suppressor.

BRIEF DESCRIPTION OF THE DRAWING

FIG. 1A–1C presents an alignment of the amino acid sequences of the deduced acid sequences of extracellular subdomains of PC42 (EC-1 through EC-7) (SEQ ID NO:95), PC43 (EC-1 through EC-6) (SEQ ID NO:97), mouse N-cadherin (EC-1 through EC-5) (SEQ ID NO:98) and *drosophila fat* EC-18 (SEQ ID NO:99). A sequence on a line in FIG. 1A continues on the same line in FIGS. 1B and 1C. The numbers in the parenthesis indicate the positions at which the amino acid appears in a SEQ ID NO.

DETAILED DESCRIPTION

The present invention is illustrated by the following examples wherein Examples 1, 2 and 3 describe the isolation by PCR of protocadherin polynucleotide sequences of the invention. Example 4 presents the construction of expression plasmids including polynucleotides encoding protocadherin-42 or protocadherin-43 and the transfection of L cells with the plasmids. The generation of antibodies to protocadherin-42 and protocadherin-43 is described in Example 5. Example 6 presents the results of immunoassays of transfected L cells for the expression of protocadherin-42 or protocadherin-43. Example 7 describes the cell aggregation properties of transfected L cells. The calcium-binding properties of pc43 are described in Example 8. The results of assays of various tissues and cell lines for the expression of protocadherin-42 and protocadherin-43 by Northern blot, Western blot and in situ hybridization are respectively presented in Examples 9, 10 and 11.

EXAMPLE 1

The polymerase chain reaction (PCR) was used to isolate novel rat cDNA fragments encoding cadherin-related polypeptides.

Design of PCR Primers

Two regions of conserved amino acid sequence, one from the middle of the third cadherin extracellular subdomain (EC-3) and the other from the C-terminus of the fourth extracellular subdomain (EC-4), were identified by comparison of the published amino acid sequences for L-CAM (Gallin et al., supra), E-cadherin (Nagafuchi et al., supra), mouse P-cadherin (Nose et al., supra), uvomorulin (Ringwald et al., supra), chicken N-cadherin (Hatta et al., supra), mouse N-cadherin [Miyatani et al., *Science*, 245:631–635 (1989)] and human P-cadherin [Shimoyama et al., *J. Cell. Biol.*, 109:1787–1794 (1989)], and the corresponding degenerate oligonucleotides respectively set out below in IUPAC nomenclature were designed for use as PCR primers.

Primer 1 (SEQ ID NO: 1)

5' AARSSNNTNGAYTRYGA 3'

Primer 2 (SEQ ID NO: 2)

3' TTRCTRTTRCGNGGNNN 5'

The degenerate oligonucleotides were synthesized using an Applied Biosystems model 380B DNA synthesizer (Foster City, Calif.).

Cloning of cDNA Sequences by PCR

PCR was carried out in a manner similar to that described in Suzuki et al., *Cell Regulation*, 2:261–270 (1991) on a rat brain cDNA preparation. Total RNA was prepared from rat brain by the guanidium isothiocyanate/cesium chloride method described in Maniatis et al., pp. 196 in *Molecular Cloning: A Laboratory Manual*, Cold Spring Harbor, N.Y.: Cold Spring Harbor Laboratory (1982). Brain poly(A)$^+$ RNAs were then isolated using a FastTrack® kit (Invitrogen, San Diego, Calif.) and cDNA was prepared using a cDNA synthesis kit (Boehringer Mannheim Biochemicals, Indianapolis, Ind.). The PCR reaction was initiated by adding 2.5 units of Taq DNA polymerase (Boehringer Mannheim Biochemicals) to 100 ng template cDNA and 10 µg of each primer, after which 35 reaction cycles of denaturation at 94° C. for 1.5 minutes, annealing at 45° C. for 2 minutes, and polymerization at 72° C. for 3 minutes were carded out. Two major bands of about 450 base pairs (bp) and 130 bp in size were found when the products of the PCR reaction were subjected to agarose gel electrophoresis. The 450 bp band corresponded to the expected length between the two primer sites corresponding to the middle of the third cadherin extracellular subdomain (EC-3) and the carboxyl terminus of the fourth cadherin extracellular subdomain (EC-4), but the 130 bp band could not be predicted from any of the previously identified cadherin sequences. The 450 bp and 130 bp bands were extracted by a freezing and thawing method. The resulting fragments were phosphorylated at the 5' end with T4 polynucleotide kinase and subcloned by a blunt-end ligation into the Sma I site of M13mp18 (Boehringer Mannheim Biochemicals) in a blunt end ligation for sequence analysis. Sequencing of the fragments was carried out by the dideoxynucleotide chain termination method using a Sequenase kit (United States Biochemicals, Cleveland, Ohio). DNA and amino acid sequence were analyzed using the Beckman Microgenie program (Fullerton, Calif.).

Analysis of cDNA Sequences

Nineteen novel partial cDNA clones were isolated. The DNA and deduced amino acid sequences of the clones (including sequences corresponding to the PCR primers) are set out as follows: RAT-123 (SEQ ID NOs: 3 and 4, respectively), RAT-212 (SEQ ID NOs: 5 and 6), RAT-214 (SEQ ID NOs: 7 and 8), RAT-216 (SEQ ID NOs: 9 and 10), RAT-218 (SEQ ID NOs: 11 and 12), RAT-224 (SEQ ID NOs: 13 and 14), RAT-312 (SEQ ID NOs: 15 and 16), RAT-313 (SEQ ID NOs: 17 and 18), RAT-314 (SEQ ID NOs: 19 and 20), RAT-315 (SEQ ID NOs: 21 and 22), RAT-316 (SEQ ID NOs: 23 and 24), RAT-317 (SEQ ID NOs: 25 and 26), RAT-321 (SEQ ID NOs: 27 and 28), RAT-323 (SEQ ID NOs: 29 and 30), RAT-336 (SEQ ID NOs: 31 and 32), RAT-352 (SEQ ID NOs: 33 and 34), RAT-411 (SEQ ID NOs: 35 and 36), RAT-413 (SEQ ID NOs: 37 and 38), and RAT-551 (SEQ ID NOs: 39 and 40).

The deduced amino acid sequences of the cDNA clones are homologous to, but distinct from the known cadherins. The cadherins described thus far have highly conserved, short amino acid sequences in the third extracellular subdomain (EC-3) including the consensus sequence D-Y-E or D-F-E located at the middle region of the subdomain and the consensus sequence D-X-N-E-X-P-X-F (SEQ ID NO: 41) or D-X-D-E-X-P-X-F (SEQ ID NO: 42) at its end (Hatta et al., supra), while the corresponding sequences of other subdomains, except for the fifth extracellular subdomain (EC-5), are D-R-E and D-X-N-D-N-X-P-X-F (SEQ ID NO: 43), respectively. In contrast, the deduced amino acid sequences of the new clones that correspond to cadherin extracellular subdomains include the sequence D-Y-E or D-F-E at one end, but have the sequence D-X-N-D-N-X-P-X-F (SEQ ID NO:43) instead of D-X-N-E-X-P-X-F (SEQ ID NO:41) or D-X-D-E-X-P-X-F (SEQ ID NO:42), at the other end. The polypeptides encoded by the partial clones are homologous to previously identified cadherins but did not show significant homology to any other sequences in Genbank. Therefore, the partial cDNAs appear to comprise a new subclass of cadherin-related molecules.

EXAMPLE 2

Various cDNA fragments structurally similar to the rat cDNAs described in Example 1 were isolated from human, mouse, and Xenopus brain cDNA preparations and from *Drosophila* and *C. elegans* whole body cDNA preparations by PCR using Primers 1 and 2 as described in Example 1. The DNA and deduced amino acid sequences of the resulting PCR fragments (including sequences corresponding to the PCR primers) are set out as follows: MOUSE-321 (SEQ ID NOs: 44 and 45), MOUSE-322 (SEQ ID NOs: 46 and 47), MOUSE-324 (SEQ ID NOs: 48 and 49), MOUSE-326 (SEQ ID NOs: 50 and 51), HUMAN-11 (SEQ ID NOs: 52 and 53), HUMAN-13 (SEQ ID NOs: 54 and 55), HUMAN-21 (SEQ ID NOs: 56 and 57), HUMAN-24 (SEQ ID NOs: 58 and 59), HUMAN-32 (SEQ ID NOs: 60 and 61), HUMAN-42 (SEQ ID NOs: 62 and 63), HUMAN-43 (SEQ ID NOs: 64 and 65), HUMAN-212 (SEQ ID NOs: 66 and 67), HUMAN-213 (SEQ ID NOs: 68 and 69), HUMAN-215 (SEQ ID NOs: 70 and 71), HUMAN-223 (SEQ ID NOs: 72 and 73), HUMAN-410 (SEQ ID NOs: 74 and 75), HUMAN-443 (SEQ ID NOs: 76 and 77), XENOPUS-21 (SEQ ID NOs: 78 and 79), XENOPUS-23 (SEQ ID NOs: 80 and 81), XENOPUS-25 (SEQ. ID NOs: 82 and 83), XENOPUS-31 (SEQ ID NOs: 84 and 85), DROSOPHILA-12 (SEQ ID NOs: 86 and 87), DROSOPHILA-13 (SEQ ID NOs: 88 and 89), DROSOPHILA-14 (SEQ ID NOs: 90 and 91) and C.ELEGANS-41 (SEQ ID NOs: 92 and 93). Comparison of the deduced amino acid sequences indicates significant similarity between sets of these clones. In particular, there are three sets of clones that appear to be cross-species homologues: RAT-218, MOUSE-322 and HUMAN-43; RAT-314, MOUSE-321 and HUMAN-11; and MOUSE-326 and HUMAN-42.

EXAMPLE 3

To ascertain the complete structure of the new proteins defined by the PCR products, two full length human cDNAs corresponding to the partial cDNAs HUMAN-42 and HUMAN-43 were isolated.

Isolation of Full-Length Human cDNAs

A human fetal brain cDNA library (Stratagene, La Jolla, Calif.) in the λZapII vector was screened by the plaque hybridization method [described in Ausubel et al., Eds., *Current Protocols in Molecular Biology*, Sections 6.1.1 to 6.1.4 and 6.2.1 to 6.2.3, John Wiley & Sons, New York (1987)] with $^{32}$P-labelled HUMAN-42 and HUMAN-43 DNA fragments. The positive clones were plaque-purified and, using a helper virus, the inserts were cut out by an in vivo excision method in the form of a Bluescript SK(+) plasmid. The insert sequences were then subcloned into the M13 vector (Boehringer Mannheim, Biochemicals) for sequencing. Several overlapping cDNA clones were isolated with each probe including two cDNAs which contained the putative entire coding sequences of two novel proteins designated protocadherin-42 (pc42) and protocadherin-43 (pc43). The DNA and deduced amino acid sequences of pc42 are set out in SEQ ID NOs: 94 and 95, respectively, while the DNA and deduced amino acid sequences of pc43 are set out in SEQ ID NOs: 96 and 97, respectively.

Analysis of Full-Length Human Clones

Comparison of the full length cDNA sequences of pc42 and pc43 to the sequences of the various DNA fragments originally obtained by PCR reveals that MOUSE-326 and HUMAN-42 correspond to a portion of the fourth extracellular subdomain (EC-4) of pc42, and RAT-314, MOUSE-321, and HUMAN-11 correspond to a portion of the third extracellular subdomain (EC-3) of pc43 and RAT-218, MOUSE-322 and HUMAN-43 correspond to a portion of the fifth extracellular domain (EC-5) of pc43.

The overall structures of pc42 and pc43 are similar to that of typical cadherins but also have distinct features. Both protocadherin cDNA sequences contain putative translation initiation sites and translated amino acid sequences start with typical signal sequences, but the clones lack the prosequences that are present in all known cadherin precursors. The cDNAs encode proteins having a large N-terminal extracellular domain and a relatively short C-terminal cytoplasmic domain connected by a transmembrane sequence. The extracellular domains of pc42 and pc43 are different in length and pc42 contains seven subdomains that closely resemble the typical cadherin extracellular subdomain while pc43 has six such subdomains. The sizes of the protocadherin cytoplasmic domains are similar to those of typical cadherins, but the sequences do not show any significant homology with those of known cadherins or cadherin-related proteins.

Amino acid identity determinations between extracellular subdomains of human pc42 and pc43, and of mouse N-cadherin (SEQ ID NO: 98) (presented as an example of a "typical" cadherin) and the eighteenth extracellular subdomain of *Drosophila fat* tumor suppressor (EC-18, SEQ ID NO: 99) (the eighteenth extracellular subdomain of fat is a prototypical fat subdomain) are presented in Table 1 below, wherein, for example, "N-EC-1×pc42" indicates that the first extracellular subdomain of N-cadherin was compared to the extracellular subdomain of pc42 indicated on the horizonal axis.

TABLE 1

|  | EC-1 | EC-2 | EC-3 | EC-4 | EC-5 | EC-6 | EC-7 |
|---|---|---|---|---|---|---|---|
| N-EC-1 × pc42 | 20 | 27 | 26 | 26 | 31 | 29 | 17 |
| N-EC-1 × pc43 | 31 | 23 | 23 | 26 | 31 | 24 |  |
| N-EC-2 × pc42 | 28 | 30 | 32 | 30 | 37 | 31 | 19 |
| N-EC-2 × pc43 | 30 | 28 | 30 | 36 | 29 | 30 |  |
| N-EC-3 × pc42 | 21 | 26 | 30 | 29 | 31 | 30 | 22 |
| N-EC-3 × pc43 | 25 | 18 | 26 | 28 | 28 | 25 |  |
| N-EC-4 × pc42 | 28 | 28 | 26 | 25 | 29 | 27 | 17 |
| N-EC-4 × pc43 | 21 | 25 | 28 | 28 | 29 | 24 |  |
| N-EC-5 × pc42 | 24 | 21 | 25 | 24 | 24 | 19 | 12 |
| N-EC-5 × pc43 | 15 | 21 | 20 | 20 | 25 | 16 |  |
| fat EC-18 × pc42 | 22 | 35 | 32 | 34 | 42 | 35 | 19 |
| fat EC-18 × pc43 | 32 | 30 | 36 | 36 | 33 | 29 |  |

The amino acid identity values between the extracellular subdomains of pc42 and pc43, and N-cadherin EC-1 through EC-5 and *Drosophila fat* EC-18 are mostly less than 40%. These identity values are comparable to the values between the subdomains of other cadherin subclasses. However, higher identity values indicate that pc42 and pc43 are more closely related to fat than to N-cadherin.

Amino acid identity determinations between extracellular subdomains of human pc42 and pc43 are presented in Table 2 below.

TABLE 2

|  | pc42 | | | | | | |
|---|---|---|---|---|---|---|---|
|  | EC-1 | EC-2 | EC-3 | EC-4 | EC-5 | EC-6 | EC-7 |
| EC-1 | 33 | 27 | 29 | 26 | 25 | 26 | 25 |
| EC-2 | 26 | 38 | 29 | 33 | 34 | 28 | 21 |
| EC-3 | 26 | 32 | 41 | 30 | 32 | 31 | 22 |
| EC-4 | 25 | 34 | 30 | 41 | 39 | 31 | 18 |
| EC-5 | 23 | 32 | 29 | 27 | 36 | 34 | 16 |
| EC-6 | 25 | 25 | 26 | 25 | 28 | 23 | 26 |

The identity values between respective EC-1, EC-2, EC-3, EC-4, EC-5 subdomains and the last subdomains of pc42 and pc43 are generally higher values than values obtained for comparisons of the protocadherins to N-cadherin. These results suggest that pc42 and pc43 are more closely related to one another than they are to classic cadherins.

FIG. 1A–1C presents an alignment of the deduced amino acid sequences of the extracellular subdomains of pc42 (EC-1 through EC-7), pc43 (EC-1 through EC-6), mouse N-cadherin (EC-1 through EC-5) and *Drosophila fat* EC-18. A sequence on a line in FIG. 1A continues on the same line in FIGS. 1B and 1C. Gaps were introduced to maximize homology. The amino acid residues described by capital letters in the "motif" line are present in more than half of the subdomains of N-cadherin, pc42, pc43 and *Drosophila fat*. The amino acid residues described by small letters in the motif line are less well conserved in human pc42, pc43, and

*Drosophila fat*. FIG. 1A–1C shows that many amino acids characteristic of other cadherin extracellular domain repeats are conserved in the pc42 and pc43 sequences, including the cadherin sequence motifs DXD, DRE and DXNDNXPXF (SEQ ID NO: 43), two glycine residues, and one glutamic acid residue. Additionally, pc42 and pc43 share unique features in comparison to N-cadherin. More amino acids at specific sites are conserved between pc42 and pc43, such as the DXDXGXN (SEQ ID NO: 100) protocadherin sequence motif near the amino terminus of the pc42 and pc43 subdomains and the AXDXGXP (SEQ ID NO: 101) sequence motif near the carboxyl terminus of the subdomains. Additionally, both protocadherins share regions that do not show significant homology with the typical cadherin motif (of N-cadherin) near the carboxyl terminus of EC-1, in the middle of EC-2 and EC-4, and at the carboxyl terminus of the last repeat. A cysteine residue is located at a similar position in the middle of EC-4 of pc42 and pc43. In general, the extracellular subdomains of pc42 and pc43 are more similar to EC-18 of fat than the extracellular subdomains of N-cadherin.

Possible Alternative Splicing

Sequence analysis of various overlapping protocadherin cDNA clones revealed that some clones contained unique sequences at the 3' end, although the 5' end sequences were identical to other clones. The sequences forming the boundaries of the 3' end regions are consistent with the consensus sequence of mRNA splicing, suggesting that these clones may correspond to alternatively spliced mRNAs. The DNA and deduced amino acid sequences of one possible product of alternative splicing of pc42 mRNA are set out in SEQ ID NOs: 102 and 103. The DNA and deduced amino acid sequences of two possible products of alternative splicing of pc43 mRNA are respectively presented in SEQ ID NO: 104 and 105, and SEQ ID NOs: 106 and 107.

EXAMPLE 4

The full length human cDNAs encoding pc42 and pc43 were expressed in L cells (ATCC CCL 1) using the pRC/RSV expression vector (Invitrogen, San Diego, Calif.). The cDNAs were isolated from the Bluescript SK(+) clones described in Example 2 by digestion with SspI followed by blunt-ending with DNA polymerase and digestion with XbaI (for pc42), or by double digestion with SpeI and EcoRV (for pc43). The pRC/RSV expression vector was digested with HindIII, followed by blunt-ending and re-digestion with XbaI for insertion of pc42 sequences, or by digested with XbaI followed by blunt-ending and re-digestion with SpeI for insertion of pc43 sequences. The isolated protocadherin DNAs were ligated into the linearized pRC/RSV vector. The resulting pc42 expression plasmid designated pRC/RSV-pc42 (ATCC 69162) and pc43 expression plasmid designated pRC/RSV-pc43 (ATCC 69163) were purified by CsCl gradient centrifugation and transfected into L cells by a Ca-phosphate method.

The pc42 and pc43 transfectants were morphologically similar to the parental cells. Northern blot analysis of L cells transfected with pc42 or pc43 DNA sequences showed that the transfected cells expressed mRNAs of a size expected to encode the particular protocadherin.

EXAMPLE 5

Rabbit polyclonal antibodies specific for pc42 and pc43 were generated as well as a mouse monoclonal antibody specific for pc43.

Preparation of Polyclonal Antibodies Specific for pc42 and pc43

DNA sequences encoding portions of the extracellular domain of pc42 and pc43 were each fused to a maltose binding protein-encoding sequence and expressed in bacteria. Specifically, DNAs corresponding to EC-4 through EC-7 of pc42 and EC-3 through EC-5 of pc43 were prepared by PCR and subcloned in the correct reading frame into the multicloning site of the pMAL expression vector (New England Bioiabs, Beverly, Mass.) which contains sequences encoding maltose binding protein immediately upstream of the multicloning site. The resulting plasmids were then introduced into *E. coli* NM522 cells (Invitrogen, San Diego, Calif.) by a single step transformation method. Expression of the fusion proteins was induced by the addition of IPTG and the fusion proteins were purified from cell extracts by amylose resin affinity chromatography (New England Biolabs) as described by the manufacturer. The fusion proteins were used for the immunization of rabbits without further purification.

Polyclonal antibodies were prepared in rabbits by immunization at four subcutaneous sites with 500 µg of purified fusion protein in Freund's complete adjuvant. Subsequent immunizations with 100 µg of the fusion protein were in Freund's incomplete adjuvant. Immune sera was passed through sepharose coupled to maltose binding protein (New England Biolabs) and polyclonal antibodies were purified from immune sera using Sepharose affinity columns prepared by reaction of the purified fusion protein with CNBr Sepharose (Pharmacia). Reactivity of the polyclonal sera with purified pc42 fusion protein and pc42 transfected cell extracts (described in Example 4) was confirmed.

Preparation of Monoclonal Antibodies to pc43

The pc43 fusion protein (containing the EC-3 through EC-5 subdomains of pc43) was used to generate monoclonal antibodies in mice according to the method of Kennett, *Methods in Enzymol.*, 58:345–359 (1978). Briefly, mice were immunized with the pc43 fusion protein (100 µg) at two subcutaneous sites. The spleen from the highest titer mouse was fused to the NS1 myeloma cell line. The resulting hybridoma supernatants were screened in a ELISA assay for reactivity with the pc43 fusion protein and with maltose binding protein. The fusion wells with the highest reactivity to the pc43 extracellular domains were subcloned. The hybridoma cell line designated 38I2C (ATCC HB 11207) produced a IgG$_1$ subtype monoclonal antibody specific for pc43. Reactivity of the monoclonal antibody produced by hybridoma cell line 38I2C to pc43 was confirmed by immunoblotting the pc43 L cell transfectants described in Example 4. The 38I2C monoclonal antibody is specific for human pc43.

EXAMPLE 6

L cells transfected with DNA sequences encoding pc42 and pc43 as prepared in Example 4 were assayed for expression of the protocadherins by immunoblot and by immunofluorescence microscopy.

Immunoblot Analysis of Protocadherin Transfectants

Cell extracts of pc42 and pc43 transfectants were subjected to SDS-PAGE and then blotted electrophoretically onto a PVDF membrane (Millipore, Bedford, Mass.). The membranes were incubated with 5% skim milk in Tris-buffered saline (TBS) for two hours and then respectively with either pc42 polyclonal sera or pc43 monoclonal antibody for one hour. The membranes were washed three times (for 5 minutes each wash) with TBS containing 0.05% Tween 20 and respectively incubated with alkaline phosphatase-conjugated anti-rabbit IgG antibody or anti-mouse IgG antibody (Promega, Madison, Wis.) in the same buffer for one hour. After washing the membranes with TBS containing 0.05% Tween 20, reactive bands were visualized by using Western Blue solution (Promega).

Anti-pc42 polyclonal antibodies stained a band of about 170 kDa molecular weight in pc42 transfected cells, but not parental L cells. The pc43-specific monoclonal antibody (38I2C) and polyclonal antibodies stained two adjacent bands of about 150 kDa molecular weight in pc43 transfected cells. The pc43 antibodies did not stain bands in parental L-cells. The molecular weights indicated by the staining of bands by the pc42 and pc43 antibodies are significantly larger than the molecular weights predicted from the deduced amino acid sequences. This discrepancy in molecular weight is common among various cadherin-related proteins and may be attributable to the glycosylation and/or cadherin specific structural properties. The pc42 antibody also stained smaller bands, which may be proteolytic degradation products.

When transfected cells were trypsinized and cell extracts were prepared, run on SDS/PAGE and immunoblotted with the appropriate antibody, the pc42 and pc43 polypeptides expressed by the transfected cells were found to be highly sensitive to proteolysis and were easily digested by 0.01% trypsin treatment. In contrast to the classic cadherins, however, these proteins were not protected from the digestion in the presence of 1–5 mM $Ca^{2+}$.

Immunofluorescence Microscopy

Transfected cells were grown on a cover slip precoated with fibronectin and were fixed with 4% paraformaldehyde for 5 minutes at room temperature or with cold methanol on ice for 10 minutes followed by 4% paraformaldehyde fixation. After washing with TBS, the cells were incubated with TBS containing 1% BSA for 30 minutes and then with anti-pc42 polyclonal antibody or anti-pc43 monoclonal antibody in TBS containing 1% BSA for 1 hour at room temperature. Cover slips were then washed with TBS containing 0.01% BSA and respectively incubated with FITC-conjugated anti-rabbit antibody or anti-mouse antibody (Cappel, Durham, N.C.) for 60 minutes at room temperature. The cells were washed again with TBS containing 0.01% BSA and subjected to fluorescence microscopy. Both pc42- specific and pc43-specific polyclonal antibodies stained the cell periphery of transfected cells expressing the protocadherin proteins, mainly at the cell-cell contact sites. The antibodies did not stain the parent L cells, nor did rabbit preimmune sera stain the pc42 and pc43 transfectants.

EXAMPLE 7

The cell aggregation properties of the transfected L cells expressing protocadherin proteins were examined. Transfected L cells were cultured in Dulbecco's Modified Eagles Medium (DMEM) (Gibco, Grand Island, N.Y.) supplemented with 10% fetal bovine serum at 37° C. in 5% $CO_2$. Cells grown near confluence were treated with 0.01% trypsin in the presence of 1 mM EGTA for 25 minutes on a rotary shaker at 37° C. and collected by centrifugation. The cells were washed three times with $Ca^{2+}$ free HEPES-buffered saline (HBS) after adding soybean trypsin inhibitor, and were resuspended in HBS containing 1% BSA. The cell aggregation assay [Urushihara et al., *Dev. Biol.*, 70:206–216 (1979)] was performed by incubating the resuspended cells in a 1:1 mixture of DMEM and HBS containing 1% BSA, 2 mM $CaCl_2$ and 20 µg/ml of deoxyribonucelease on a rotary shaker at 37° C. for 30 minutes to 6 hours.

The pc42 and pc43 transfectants did not show any significant cell aggregation activity during periods of incubation less than 1 hour. This is in contrast to the cell aggregation that occurs with classic cadherins in similar experiments (Nagafuchi et al., supra, and Hatta et al., supra). However, prolonged incubation of transfected cells (more than 1–2 hours) resulted in gradual re-aggregation of the cells into small aggregates. Similar results were obtained when single cell suspensions of transfected cells were prepared by trypsin treatment in the presence of $Ca^{2+}$. No re-aggregation was observed under the same conditions when untransfected L cells or L cells transfected with pRC/RSV vector alone were tested.

EXAMPLE 8

The procedures of Maruyama et al., *J. Biochem.*, 95:511–519 (1984) were used to determine the calcium binding properties of pc43 by Western blot analysis in the presence or absence of calcium-45. The pc43 fusion protein described in Example 5 containing pc43 subdomains EC-3 through EC-5 was compared to the calcium binding protein calmodulin. Samples of purified pc43 fusion protein were run on SDS/PAGE and electrophoretically transferred to PVDF membrane. Binding of the $^{45}Ca^{2+}$ to the pc43 fusion protein was detected by autoradiography and was determined to be nearly as efficient as binding of $^{45}Ca^{2+}$ to calmodulin. In contrast, there was no binding of calcium to purified maltose binding protein lacking the pc43 extracellular domain. The pc43 subdomains EC-3 through EC-5 contain sequences highly homologous to the putative $Ca^{2+}$ binding motifs found in E-cadherin. [See, Ringwald et al., *EMBO J.*, 6:3647–3653.]

EXAMPLE 9

The expression of mRNA encoding pc42 and pc43 was assayed in various tissues and cell lines by Northern blot.

Total RNAs were prepared by the guanidium isothiocyanate method and poly(A)+ RNAs were isolated using a FastTrack kit (Invitrogen). RNA preparations were electrophoresed in a 0.8% agarose gel under denaturing conditions and transferred onto a nitrocellulose filter using a capillary method. Northern blot analyses were performed according to the method of Thomas, *Proc. Natl. Acad. Sci. USA*, 77:5201–5205 (1980). The final wash was in 0.2× standard saline citrate containing 0.1% sodium dodecyl sulfate at 65° C. for 10 minutes.

Protocadherin mRNA Expression in Adult Rat Tissues

Total mRNA preparations of rat tissues including brain, heart, liver, lung, skin, kidney and muscle were separated electrophoretically under denaturing conditions (10 µg mRNA/lane) and transferred onto nitrocellulose filters. The filters were hybridized with $^{32}P$-labelled cDNA fragments MOUSE-326 (which corresponds to EC-4 of human pc42) and RAT-218 (which corresponds to EC-5 of human pc43). The mRNAs of both protocadherins were highly expressed in brain. The pc42 probe detected a major band of 7 kb and a minor band of 4 kb in size, possibly representing the products of alternative splicing. The pc43 probe hybridized to a major band of 5 kb in size and with minor bands of smaller sizes.

Developmental Expression of Protocadherin mRNA in Rat Brain

To examine the developmental regulation of mRNA expression of the protocadherins, brain mRNA from rats at embryonic days 17 and 20, neonatal days 5 and 11 and from adult rats was prepared and subjected to Northern blot analysis as described above for other rat tissues. β-actin was used as an internal standard. mRNA levels for pc42 and pc43 proteins increased during embryonic development of the brain as compared with β-actin expression.

Protocadherin mRNA Expression in Human Cell Lines

Several neuronal and glial cell lines (including human SK-N-SH neuroblastoma, human U251 glioma, and mouse Neuro-2a neuroblastoma cell lines) were assayed by Northern blot using $^{32}$P-labelled for expression of pc42 and pc43 mRNA. Human cell lines were probed with HUMAN-42 (which corresponds to EC-4 of human pc42) and HUMAN-43 (which Corresponds to EC-5 of human pc43) cDNA fragments while the mouse cell line was probed with MOUSE-326 (which corresponds to EC-4 of human pc42) and RAT-322 (which corresponds to EC-5 of human pc43) cDNA fragments. SK-N-SH human neuroblastoma cells and U251 human glioma cells were found to express pc43 mRNA and Neuro-2a mouse neuroblastoma cells were found to express pc42 mRNA.

EXAMPLE 10

Expression of pc43 protein in various human and rat tissues was assayed by Western blot.

Analysis of Rat Cardiac Muscle Extracts for pc43 Protein Expression

A rat heart non-ionic detergent extract was prepared by freezing a heart in liquid nitrogen after removal, powdering in a mortar and pestle, grinding briefly in a polytron in 0.5% Nonidet P40 in [10 mM PIPES (pH 6.8), 50 mM NaCl, 250 mM $NH_4SO_4$, 300 mM sucrose, 3 mM $MgCl_2$] and microfuging for 15 minutes. Samples were separated by SDS/PAGE and electrophoretically transferred to nitrocellulose (Towbin et al., *PNAS* 76:4350–4354, 1979). Two pc43 protein bands with molecular weights of 150 KDa and 140 KDa were detected with rabbit polyclonal antibodies to pc43 by the immunoblot method described in Example 6.

Analysis of Tissue Sections for pc43 Protein Expression

To determine the localization of the protocadherins in various tissues, human and rat adult tissues were removed, incubated in 30% sucrose in PBS for 30 minutes at 4° C., embedded in OCT compound (Tissue-Tek, Elkhart, Ind.) in cryomolds and quickly frozen. Six micron sections were cut and placed on glass slides. The slides were washed with PBS and fixed in 3% p-formaldehyde for 5 minutes. To permeablize the tissue sections, the slides were immersed in –20° C. acetone for 10 minutes and air dried. The sections were blocked with 2% goat serum and 1% BSA in PBS for 30 minutes and then incubated with the rabbit anti-pc43 polyclonal antisera for 1 hour at room temperature. The sections were rinsed 3 times in PBS containing 0.1% BSA and incubated with a biotinylated anti-rabbit (Vector Laboratories, Burlingame, Calif.) in 1% BSA in PBS for 30 minutes. After rinsing 3 times, strepavidin-conjugated with FITC (Vector Laboratories) was added for 30 minutes and again washed 3 times. For co-localization studies, an appropriate primary antibody was used with a TRITC-conjugated secondary antibody.

Immunolocalization of pc43 in cardiac muscle shows that pc43 is localized in a repeating pattern which is consistent with pc43 being associated with the sarcomeres. Sarcomeres are repetitive contractile units between the *fascia adherens* in skeletal and cardiac muscle. Co-localization with cytoskeletal proteins shows that pc43 is present at the ends of the sarcomeres in the Z lines which are associated with desmin and the actin-binding protein vinculin, and alpha-actinin. The thin microfilaments of F-actin are associated with the thick myosin filaments between the Z lines. In contrast, N-cadherin is localized at the ends of cardiac myocytes at the *fascia adherens* junctions at sites of mycocyte:myocyte contact. The localization of pc43 in cardiac muscle suggests that pc43 may play a role in muscle contraction in the anchoring of the contractile apparatus to the plasma membrane.

Similar localization for pc43 was observed in rat skeletal muscle. Ultrastructural studies have shown that dystrophin, the gene product lacking in Duchenne muscular dystrophy, is a component of the sarcolemma [Porter et al., *J. Cell. Biol.*, 117:997–1005 (1992)]. The sarcolemma is connected to the contractile apparatus at the M and Z lines where pc43 is localized.

Reactivity of anti-pc43 polyclonal antibody and monoclonal antibody 38I2C on frozen sections of rat and human cerebellum, respectively, shows that the major sites of pc43 expression are located in Purkinje cells and the granule cell layer which contains numerous small neurons.

Analysis of pc43 Protein Expression in Human Cell Lines

Immunocytochemical localization of pc43 in Sk-N-SH neuroblastoma cells and UW28 astrocytoma cells using anti-pc43 antibodies reveals a punctate cell surface distribution of pc43 and in some cells there is a localization at the tips of extensions of neuronal foot processes. At sites of cell-cell contact of UW28 astrocytoma cells, pc43 is organized in a series of parallel lines. The lines start at the contact site and extend approximately 5 micron. F-actin microfilaments were identified with rhodamine-phalloidin (Molecular Probes, Eugene, Oreg., as described by the manufacturer) showing that the micro filaments in the cell appear to end in the pc43 linear structures which extend from the edge of the cell at sites of cell contact.

Immunoblotting studies with pc43 specific antibodies show that a protein with a molecular weight of 140 kDa is recognized in human Sk-N-SH neuroblastoma cells and in UW28 astrocytoma cells.

EXAMPLE 11

In situ hybridization experiments using protocadherin specific RNA probes were preformed on cryosections of rat tissue.

Sense and antisense $^{35}$S-riboprobes were made using the standard procedure described by Promega (Madison, Wis.). An approximately 400 bp EcoRI-XbaI fragment of the MOUSE-326 cDNA clone was used as a pc42 specific probe. This fragment encodes the middle of EC-3 to the end of EC-4 of pc42. An approximately 700 bp SmaI fragment of the RAT-218 cDNA clone was used as a pc43 specific probe. The fragment encodes the end of EC-3 to the end of EC-5 of pc43.

Rat adult tissues were harvested and immediately embedded with OCT Compound (Tissue-Tek) in cryomolds and quickly frozen in a bath of 95% ethanol/dry ice. The frozen blocks were stored at –80° C. until cut. Six micron tissue sections were cut using a cryostat (Reichert-Jung, Model #2800 Frigocut N, Leica, Inc., Gilroy, Calif.). Cut tissue sections were stored at –80° C.

The in situ protocol used was a variation of that described by Angerer et al., *Methods in Enzymology*, 152:649–660, 1987. All solutions were treated with diethylpyrocarbonate (DEPC, Sigma, St. Louis, Mo.) to remove RNase contamination. The tissue sections were first fixed in 4% paraformaldehyde at 4° C. for 20 minutes. To remove excess paraformaldehyde and stop the tissue fixation, the slides were washed in PBS (phosphate buffered saline), denatured in a graded series of alcohols (70, 95, 100%) and then dried. To prevent the tissue from detaching from the glass slide during the in situ procedure, the tissue sections were treated in a poly-L-lysine solution (Sigma) at tooth temperature for 10 minutes. To denature all RNA in the tissue, the sections were placed in a solution of 70% formamide/2×SSC [0.15M NaCl/0.3M Na citrate, pH 7.0] at 70° C. for 2 minutes after which they were rinsed in chilled 2× SSC, alehydrated in a graded series of alcohols and then dried. Once dried, the sections were prehybridized in hybridization buffer (50% formamide/50 mM DTT (dithiothrietol)/0.3M NaCl/20 mM Tris, pH 8.0/5 mM EDTA/1× Denhardt's (0.02% Ficoll Type 400/0.02% polyvinylpyrrolidone/0.02% BSA)/10% Dextran Sulfate) at the final hybridization temperature for approximately 4 hours. After prehybridization, approximately $1×10^6$ cpm of the appropriate riboprobe was added to each section. The sections were generally hybridized at 45° C. overnight (12–16 hours). To insure that the hybridization seen was specific, in some experiments the hybridization stringency was increased by raising the hybridization temperature to 50° C. As both the 45° C. and 50° C. experiments gave comparable results, the standard hybridization temperature used was 45° C.

To remove excess, nonhybridized probe, the sections were put through a series of washes. The sections were first rinsed in 4× SSC to remove the bulk of the hybridization solution and probe. Next a 15 minute wash in 4× SSC/50 mM DTT was carried out at room temperature. Washes at increased stringencies were also utilized. A 40 minute wash in 50% formamide/2× SSC/50 mM DTT was performed at 60° C. Four final room temperature washes were carried out for 10 minutes each: two in 2× SSC and two in 0.1× SSC. The washed slides were dehydrated in a graded series of alcohols and dried.

To visualize the hybridized probe, the slides were dipped in Kodak NTB2 nuclear emulsion (International Biotechnology, New Haven, Conn.) which had been diluted 1:1 in $dH_2O$. Once dry, the slides were stored at 4° C. in light-tight boxes for the appropriate exposure time. The in situ slides were independently viewed by two persons and scored positive or negative for hybridization signal.

All in situ hybridization studies were performed on rat tissue. Because results from Northern blot experiments (see Example 9) indicated that both pc42 and pc43 are expressed in adult brain, in situ hybridization studies were carried out to localize the expression of these molecules to specific brain cell types. Hybridization seen in the normal adult rat brian was specific (no background hybridization was seen with the sense probes) and was localized to specific regions in the brain. The overall pattern of expression seen for pc42 and pc43 was very similar, with the major difference being in the level of expression. pc43 appears to be expressed at a lower level than pc42. Both molecules are expressed in the germinal and pyramidal cells of the hippocampus, Purkinje cells of the cerebellum and neurons in grey matter. In addition, pc42 is expressed in glial cells in the white matter but, in contrast to the expression of pc43 in glioma cell lines (as described in Example 9), expression of pc43 in normal glial cells was not observed. In the spinal chord, both protocadherins are expressed in the motor neurons in the gray matter and pc42 is expressed in the glial cells in the white matter.

When expression of both protocadherin molecules was determined in brains and spinal chords from rats having EAE (experimental allergic encephalomyelitis) [Vandenbark et al., Cell. Immunol., 12:85–93 (1974)], the same structures as described above were found to be positive. In addition, expression of pc42 was observed in the leukocytic infiltrates in the EAE tissues. Expression of pc42 in leukocytes was confirmed by in situ hybridization analysis of two leukocytic cell lines, RBL-1 and y3.

While the present invention has been described in terms of specific methods and compositions, it is understood that variations and modifications will occur to those skilled in the art. Therefore, only such limitations as appear in the claims should be placed on the invention.

---

What is claimed is:

1. A purified and isolated full-length mammalian protocadherin-42 polypeptide.

2. The protocadherin-42 polypeptide of claim 2 consisting of the amino acid sequence set forth in SEQ ID NO: 95.

3. A purified and isolated protocadherin-42 polypeptide fragment comprising amino acid residues 354 through 818 of SEQ ID NO: 95.

* * * * *

UNITED STATES PATENT AND TRADEMARK OFFICE
CERTIFICATE OF CORRECTION

PATENT NO. : 5,663,300

DATED : September 2, 1997

INVENTOR(S) : Shintaro Suzuki

It is certified that error appears in the above-identified patent and that said Letters Patent is hereby corrected as shown below:

On the title page, item[56]:

Under References Cited, Other Publications, Fujimori *et al.*, replace "Ecotopic" with --Ectopic--.

Under References Cited, Other Publications, Liaw *et al.*, replace "ENdothelial" with --Endothelial--.

Column 2, line 30, after "four" delete --.--.

Column 3, line 2, replace "supressor" with --suppressor--.

Column 3, line 3, replace "supress" with --suppress--.

Column 10, line 8, replace "Bioiabs" with --Biolabs--.

Column 13, line 8, replace "Corresponds" with --corresponds--.

Column 14, line 24, replace "micro filaments" with --microfilaments--.

Column 14, line 35, replace "preformed" with --performed--.

Column 14, line 64, replace "tooth" with --room--.

Column 15, line 1, replace "alehydrated" with --dehydrated--.

UNITED STATES PATENT AND TRADEMARK OFFICE
CERTIFICATE OF CORRECTION

PATENT NO. : 5,663,300
DATED : September 2, 1997
INVENTOR(S) : Shintaro Suzuki

It is certified that error appears in the above-identified patent and that said Letters Patent is hereby corrected as shown below:

Column 16, line 7, replace "brian" with --brain--.

Column 129, line 53, replace "claim 2" with --claim 1--.

Signed and Sealed this

Twenty-first Day of March, 2000

Attest:

Attesting Officer

Q. TODD DICKINSON

Commissioner of Patents and Trademarks

SEQUENCE LISTING ( 1 ) GENERAL INFORMATION:

( i i i ) NUMBER OF SEQUENCES: 107

( 2 ) INFORMATION FOR SEQ ID NO:1:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

AARSSNNTNG AYTRYGA 17

( 2 ) INFORMATION FOR SEQ ID NO:2:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

TTRCTRTTRC GNGGNNN 17

( 2 ) INFORMATION FOR SEQ ID NO:3:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
AAGGGAGTGG ACTTTGAGGA GCAGCCTGAG CTTAGTCTCA TCCTCACGGC TTTGGATGGA      60
GGGACTCCAT CCAGGTCTGG GACTGCATTG GTTCAAGTGG AAGTCATAGA TGCCAATGAC     120
AACGCACCGT A                                                          131
```

( 2 ) INFORMATION FOR SEQ ID NO:4:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Lys Gly Val Asp Phe Glu Glu Gln Pro Glu Leu Ser Leu Ile Leu Thr
 1               5                  10                  15

Ala Leu Asp Gly Gly Thr Pro Ser Arg Ser Gly Thr Ala Leu Val Gln
            20                  25                  30

Val Glu Val Ile Asp Ala Asn Asp Asn Ala Pro
            35                  40
```

( 2 ) INFORMATION FOR SEQ ID NO:5:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
AAACGCATGG ATTTCGAGGA GTCTTCCTCC TACCAGATCT ATGTGCAAGC TACTGACCGG      60
GGACCAGTAC CCATGGCGGG TCATTGCAAG GTGTTGGTGG ACATTATAGA TGTGAACGAC     120
AACGCACCTA A                                                          131
```

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Lys Ala Met Asp Phe Glu Glu Ser Ser Ser Tyr Gln Ile Tyr Val Gln
 1               5                  10                  15

Ala Thr Asp Arg Gly Pro Val Pro Met Ala Gly His Cys Lys Val Leu
            20                  25                  30
```

```
          Val  Asp  Ile  Ile  Asp  Val  Asn  Asp  Asn  Ala  Pro
                    35                  40
```

( 2 ) INFORMATION FOR SEQ ID NO:7:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
AAGCGACTGG  ACTTTGAGAC  CCTGCAGACC  TTCGAGTTCA  GCGTGGGTGC  CACAGACCAT    60

GGCTCCCCCT  CGCTCCGCAG  TCAGGCTCTG  GTGCGCGTGG  TGGTGCTGGA  CCACAATGAC   120

AATGCCCCCA  A                                                            131
```

( 2 ) INFORMATION FOR SEQ ID NO:8:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Lys  Arg  Leu  Asp  Phe  Glu  Thr  Leu  Gln  Thr  Phe  Glu  Phe  Ser  Val  Gly
 1             5                      10                       15

Ala  Thr  Asp  His  Gly  Ser  Pro  Ser  Leu  Arg  Ser  Gln  Ala  Leu  Val  Arg
          20                      25                      30

Val  Val  Val  Leu  Asp  His  Asn  Asp  Asn  Ala  Pro
          35                      40
```

( 2 ) INFORMATION FOR SEQ ID NO:9:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
AAGGGCCTGG  ATTACGAGGC  ACTGCAGTCC  TTCGAGTTCT  ACGTGGGCGC  TACAGATGGA    60

GGCTCACCCG  CGCTCAGCAG  CCAGACTCTG  GTGCGGATGG  TGGTGCTGGA  TGACAACGAC   120

AACGCCCCTA  A                                                            131
```

( 2 ) INFORMATION FOR SEQ ID NO:10:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Lys  Gly  Leu  Asp  Tyr  Glu  Ala  Leu  Gln  Ser  Phe  Glu  Phe  Tyr  Val  Gly
 1             5                      10                       15

Ala  Thr  Asp  Gly  Gly  Ser  Pro  Ala  Leu  Ser  Ser  Gln  Thr  Leu  Val  Arg
```

20                      25                          30
        Met Val Val Leu Asp Asp Asn Asp Asn Ala Pro
                    35                  40

( 2 ) INFORMATION FOR SEQ ID NO:11:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

AAGGCGTTTG ATTTTGAGGA TCAGAGAGAG TTCCAGCTAA CCGCTCATAT AAACGACGGA        60

GGTACCCCGG TTTTGGCCAC CAACATCAGC GTGAACATAT TTGTTACTGA CCGCAATGAC       120

AACGCCCCGC A                                                            131

( 2 ) INFORMATION FOR SEQ ID NO:12:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

Lys Ala Phe Asp Phe Glu Asp Gln Arg Glu Phe Gln Leu Thr Ala His
        1               5                   10                  15

Ile Asn Asp Gly Gly Thr Pro Val Leu Ala Thr Asn Ile Ser Val Asn
                        20                  25                  30

Ile Phe Val Thr Asp Arg Asn Asp Asn Ala Pro
                    35                  40

( 2 ) INFORMATION FOR SEQ ID NO:13:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AAGGCGGTGG ATTACGAAAT CACCAAGTCC TATGAGATAG ATGTTCAAGC CCAAGATCTG        60

GGTCCCAATT CTATTCCTGC TCATTGCAAA ATTATAATTA AGGTCGTGGA TGTCAACGAC       120

AACGCTCCCA A                                                            131

( 2 ) INFORMATION FOR SEQ ID NO:14:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

Lys Ala Val Asp Tyr Glu Ile Thr Lys Ser Tyr Glu Ile Asp Val Gln
        1               5                   10                  15

Ala Gln Asp Leu Gly Pro Asn Ser Ile Pro Ala His Cys Lys Ile Ile
        20                      25                  30

Ile Lys Val Val Asp Val Asn Asp Asn Ala Pro
        35                  40

( 2 ) INFORMATION FOR SEQ ID NO:15:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TATGACCATG ATTACGAGAC AACCAAAGAA TATACACTGC GGATCCGGGC CCAGGATGGT    60

GGCCGGACTC CACTTTCCAA CGTCTCCGGT CTAGTAACCG TGCAGGTCCT AGACATCAAC   120

GACAATGCCC CCCCA   135

( 2 ) INFORMATION FOR SEQ ID NO:16:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

Tyr Asp His Asp Tyr Glu Thr Thr Lys Glu Tyr Thr Leu Arg Ile Arg
1               5                   10                  15

Ala Gln Asp Gly Gly Arg Thr Pro Leu Ser Asn Val Ser Gly Leu Val
        20                      25                  30

Thr Val Gln Val Leu Asp Ile Asn Asp Asn Ala Pro
        35                  40

( 2 ) INFORMATION FOR SEQ ID NO:17:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GGGGGGTCGA TTACGAGGAG AACGGCATGT TAGAGATCGA CGTGCAGGCC AGAGACCTAG    60

GACCTAACCC AATTCCAGCC CATTGCAAGG TCACAGTCAA GCTCATCGAC CGCAATGATA   120

ACGCCCCCA   129

( 2 ) INFORMATION FOR SEQ ID NO:18:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
        Arg  Gly  Val  Asp  Tyr  Glu  Glu  Asn  Gly  Met  Leu  Glu  Ile  Asp  Val  Gln
        1              5                        10                       15

Ala  Arg  Asp  Leu  Gly  Pro  Asn  Pro  Ile  Pro  Ala  His  Cys  Lys  Val  Thr
                       20                       25                       30

Val  Lys  Leu  Ile  Asp  Arg  Asn  Asp  Asn  Ala  Pro
                  35                       40
```

(2) INFORMATION FOR SEQ ID NO:19:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
AAGGGGTTGG  ACTACGAAGA  CACCAAACTC  CATGAGATTT  ACATCCAGGC  CAAAGACAAA         60

GGTGCCAATC  CGGAAGGAGC  GCATTGCAAA  GTACTGGTAG  AGGTTGTGGA  CGTTAACGAC        120

AATGCCCCTC  A                                                                 131
```

(2) INFORMATION FOR SEQ ID NO:20:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
        Lys  Gly  Leu  Asp  Tyr  Glu  Asp  Thr  Lys  Leu  His  Glu  Ile  Tyr  Ile  Gln
        1              5                        10                       15

Ala  Lys  Asp  Lys  Gly  Ala  Asn  Pro  Glu  Gly  Ala  His  Cys  Lys  Val  Leu
                       20                       25                       30

Val  Glu  Val  Val  Asp  Val  Asn  Asp  Asn  Ala  Pro
                  35                       40
```

(2) INFORMATION FOR SEQ ID NO:21:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
AAGGGTTTGG  ACTTTGAGCA  AGTAGATGTC  TACAAAATCC  GCGTTGACGC  GACGGACAAA         60

GGACACCCTC  CGATGGCAGG  CCATTGCACT  GTTTTAGTGA  GGGTATTGGA  TGAAAACGAC        120

AATGCGCCTC  T                                                                 131
```

(2) INFORMATION FOR SEQ ID NO:22:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein ( x i ) SEQUENCE DESCRIPTION: SEQ ID NO:22:

Lys Gly Leu Asp Phe Glu Gln Val Asp Val Tyr Lys Ile Arg Val Asp
1               5                   10                  15

Ala Thr Asp Lys Gly His Pro Pro Met Ala Gly His Cys Thr Val Leu
            20                  25                  30

Val Arg Val Leu Asp Glu Asn Asp Asn Ala Pro
        35                  40

( 2 ) INFORMATION FOR SEQ ID NO:23:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

AAGGGTATAG ACTTCGAGCA GATCAAGGAC TTCAGCTTTC AAGTGGAAGC CCGGGACGCC    60

GGCAGTCCCC AGGCGCTGTC CGGCAACTGC ACTGTCAACA TCTTGATAGT GGATCAGAAC    120

GACAACGCCC CTAA    134

( 2 ) INFORMATION FOR SEQ ID NO:24:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

Lys Gly Ile Asp Phe Glu Gln Ile Lys Asp Phe Ser Phe Gln Val Glu
1               5                   10                  15

Ala Arg Asp Ala Gly Ser Pro Gln Ala Leu Ala Gly Asn Thr Thr Val
            20                  25                  30

Asn Ile Leu Ile Val Asp Gln Asn Asp Asn Ala Pro
        35                  40

( 2 ) INFORMATION FOR SEQ ID NO:25:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

AAGCCGTTCG ACTATGAGCA AACCGCCAAC ACGCTGGCAC AGATTGACGC CGTGCTGGAA    60

AAACAGGGCA GCAATAAATC GAGCATTCTG GATGCCACCA TTTTCCTGGC CGATAAAAAC    120

GACAATGCGC CAGA    134

( 2 ) INFORMATION FOR SEQ ID NO:26:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:26:

```
Lys Pro Phe Asp Tyr Glu Gln Thr Ala Asn Thr Leu Ala Gln Ile Asp
1               5                   10                  15

Ala Val Leu Glu Lys Gln Gly Ser Asn Lys Ser Ser Ile Leu Asp Ala
            20                  25                  30

Thr Ile Phe Leu Ala Asp Lys Asn Asp Asn Ala Pro
        35                  40
```

(2) INFORMATION FOR SEQ ID NO:27:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:27:

```
AAGCGGCTGG ATTTCGAACA GTTCCAGCAG CACAAGCTGC TCGTAAGGGC TGTTGATGGA        60
GGAATGCCGC CACTGAGCAG CGATGTGGTC GTCACTGTGG ATGTCACCGA CCTCAACGAT       120
AACGCGCCCT A                                                            131
```

(2) INFORMATION FOR SEQ ID NO:28:

(i) SEQUENCE CHARACTERISTICS:
        (A) LENGTH: 43 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:28:

```
Lys Arg Leu Asp Phe Glu Gln Phe Gln Gln His Lys Leu Leu Val Arg
1               5                   10                  15

Ala Val Asp Gly Gly Met Pro Pro Leu Ser Ser Asp Val Val Val Thr
            20                  25                  30

Val Asp Val Thr Asp Leu Asn Asp Asn Ala Pro
        35                  40
```

(2) INFORMATION FOR SEQ ID NO:29:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:29:

```
AAGGGGATAG ACTTTGAGAG TGAGAATTAC TATGAATTTG ATGTGCGGGC TCGCGATGGG        60
GGTTCTCCAG CCATGGAGCA ACATTGCAGC CTTCGAGTGG ATCTGCTGGA CGTAAATGAC       120
AACGCCCCAC T                                                            131
```

(2) INFORMATION FOR SEQ ID NO:30:

(i) SEQUENCE CHARACTERISTICS:
        (A) LENGTH: 43 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:30:

| Lys | Gly | Ile | Asp | Phe | Glu | Ser | Glu | Asn | Tyr | Tyr | Glu | Phe | Asp | Val | Arg |
|---|---|---|---|---|---|---|---|---|---|---|---|---|---|---|---|
| 1 | | | | 5 | | | | | 10 | | | | | 15 | |

| Ala | Arg | Asp | Gly | Gly | Ser | Pro | Ala | Met | Glu | Gln | His | Cys | Ser | Leu | Arg |
|---|---|---|---|---|---|---|---|---|---|---|---|---|---|---|---|
| | | | 20 | | | | | 25 | | | | | 30 | | |

| Val | Asp | Leu | Leu | Asp | Val | Asn | Asp | Asn | Ala | Pro |
|---|---|---|---|---|---|---|---|---|---|---|
| | | 35 | | | | | 40 | | | |

(2) INFORMATION FOR SEQ ID NO:31:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
AAGGCATTGG ACTTTGAGGC CCGGCGACTG TATTCGCTGA CAGTTCAGGC CACGGACCGA      60
GGCGTGCCCT CGCTCACCGG GCGTGCCGAA GCGCTTATCC AGCTGCTAGA TGTCAACGAC     120
AACGCACCCA T                                                          131
```

(2) INFORMATION FOR SEQ ID NO:32:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

| Lys | Ala | Leu | Asp | Phe | Glu | Ala | Arg | Arg | Leu | Tyr | Ser | Leu | Thr | Val | Gln |
|---|---|---|---|---|---|---|---|---|---|---|---|---|---|---|---|
| 1 | | | | 5 | | | | | 10 | | | | | 15 | |

| Ala | Thr | Asp | Arg | Gly | Val | Pro | Ser | Leu | Thr | Gly | Arg | Ala | Glu | Ala | Leu |
|---|---|---|---|---|---|---|---|---|---|---|---|---|---|---|---|
| | | | 20 | | | | | 25 | | | | | 30 | | |

| Ile | Gln | Leu | Leu | Asp | Val | Asn | Asp | Asn | Ala | Pro |
|---|---|---|---|---|---|---|---|---|---|---|
| | | 35 | | | | | 40 | | | |

(2) INFORMATION FOR SEQ ID NO:33:

(i) SEQUENCE CHARACTERISTICS:
        (A) LENGTH: 125 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
AAGCCAATTG ATTACGAGGC AACTCCATAC TATAACATGG AAATTGTAGC CACAGACAGC      60
GGAGGTCTTT CGGGAAAATG CACTGTGTCT ATACAGGTGG TGGATGTGAA CGACAACGCC     120
CCCAA                                                                 125
```

(2) INFORMATION FOR SEQ ID NO:34:

(i) SEQUENCE CHARACTERISTICS:
        (A) LENGTH: 41 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:34:

| Lys | Pro | Ile | Asp | Tyr | Glu | Ala | Thr | Pro | Tyr | Tyr | Asn | Met | Glu | Ile | Val |
|---|---|---|---|---|---|---|---|---|---|---|---|---|---|---|---|
| 1 | | | | 5 | | | | | 10 | | | | | 15 | |

| Ala | Thr | Asp | Ser | Gly | Gly | Leu | Ser | Gly | Lys | Cys | Thr | Val | Ser | Ile | Gln |
|---|---|---|---|---|---|---|---|---|---|---|---|---|---|---|---|
| | | | 20 | | | | | 25 | | | | | 30 | | |

| Val | Val | Asp | Val | Asn | Asp | Asn | Ala | Pro |
|---|---|---|---|---|---|---|---|---|
| | | 35 | | | | 40 | | |

( 2 ) INFORMATION FOR SEQ ID NO:35:

( i ) SEQUENCE CHARACTERISTICS:
( A ) LENGTH: 446 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:35:

```
AAGCGGGTAG ACTTCGAAAT GTGCAAAAGA TTTTACCTTG TGGTGGAAGC TAAAGACGGA        60
GGCACCCCAG CCCTCAGCAC GGCAGCCACT GTCAGCATCG ACCTCACAGA TGTGAATGAT       120
AACCCTCCTC GGTTCAGCCA AGATGTCTAC AGTGCTGTCA TCAGTGAGGA TGCCTTAGAG       180
GGGGACTCTG TCATTCTGCT GATAGCAGAA GATGTGGATA GCAAGCCTAA TGGACAGATT       240
CGGTTTTCCA TCGTGGGTGG AGATAGGGAC AATGAATTTG CTGTCGATCC AATCTTGGGA       300
CTTGTGAAAG TTAAGAAGAA ACTGGACCGG GAGCGGGTGT CAGGATACTC CCTGCTCATC       360
CAGGCAGTAG ATAGTGGCAT TCCTGCAATG TCCTCAACGA CAACTGTCAA CATTGATATT       420
TCTGATGTGA ACGACAACGC CCCCCT                                            446
```

( 2 ) INFORMATION FOR SEQ ID NO:36:

( i ) SEQUENCE CHARACTERISTICS:
( A ) LENGTH: 148 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:36:

| Lys | Arg | Val | Asp | Phe | Glu | Met | Cys | Lys | Arg | Phe | Tyr | Leu | Val | Val | Glu |
|---|---|---|---|---|---|---|---|---|---|---|---|---|---|---|---|
| 1 | | | | 5 | | | | | 10 | | | | | 15 | |

| Ala | Lys | Asp | Gly | Gly | Thr | Pro | Ala | Leu | Ser | Thr | Ala | Ala | Thr | Val | Ser |
|---|---|---|---|---|---|---|---|---|---|---|---|---|---|---|---|
| | | | 20 | | | | | 25 | | | | | 30 | | |

| Ile | Asp | Leu | Thr | Asp | Val | Asn | Asp | Asn | Pro | Pro | Arg | Phe | Ser | Gln | Asp |
|---|---|---|---|---|---|---|---|---|---|---|---|---|---|---|---|
| | | | 35 | | | | | 40 | | | | | 45 | | |

| Val | Tyr | Asp | Ala | Val | Ile | Ser | Glu | Asp | Ala | Leu | Glu | Gly | Asp | Ser | Val |
|---|---|---|---|---|---|---|---|---|---|---|---|---|---|---|---|
| | | 50 | | | | | 55 | | | | | 60 | | | |

| Ile | Leu | Leu | Ile | Ala | Glu | Asp | Val | Asp | Ser | Lys | Pro | Asn | Gly | Gln | Ile |
|---|---|---|---|---|---|---|---|---|---|---|---|---|---|---|---|
| 65 | | | | | 70 | | | | | 75 | | | | | 80 |

| Arg | Phe | Ser | Ile | Val | Gly | Gly | Asp | Arg | Asp | Asn | Glu | Phe | Ala | Val | Asp |
|---|---|---|---|---|---|---|---|---|---|---|---|---|---|---|---|
| | | | | 85 | | | | | 90 | | | | | 95 | |

| Pro | Ile | Leu | Gly | Leu | Val | Lys | Val | Lys | Lys | Leu | Asp | Arg | Glu | Arg |
|---|---|---|---|---|---|---|---|---|---|---|---|---|---|---|
| | | | 100 | | | | | 105 | | | | | 110 | |

```
        Val  Ser  Gly  Tyr  Ser  Leu  Leu  Ile  Gln  Ala  Val  Asp  Ser  Gly  Ile  Pro
             115                 120                      125

Ala  Met  Ser  Ser  Thr  Thr  Thr  Val  Asn  Ile  Asp  Ile  Ser  Asp  Val  Asn
             130                 135                      140

Asp  Asn  Ala  Pro
        145
```

( 2 ) INFORMATION FOR SEQ ID NO:37:

( i ) SEQUENCE CHARACTERISTICS:
        ( A ) LENGTH: 440 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

```
AAGGGGGTTG  ATTATGAGAC  AAACCCACGG  CTACGACTGG  TGCTACAGGC  AGAGAGTGGA       60
GGAGCCTTTG  CTTTCTCGGT  GCTGACCCTG  ACCCTTCAAG  ATGCCAATGA  CAATGCTCCC      120
CGTTTCCTGC  AGCCTCACTA  CGTGGCTTTC  CTGCCAGAGT  CCCGACCCTT  GGAAGGGCCC      180
CTGCTGCAGG  TGGAAGCAGA  CGACCTGGAT  CAAGGCTCTG  GAGGACAGAT  CTCCTACAGT      240
CTGGCTGCAT  CCCAGCCAGC  ACGGGGCTTG  TTCCATGTAG  ACCCAGCCAC  AGGCACTATC      300
ACTACCACAG  CCATCCTGGA  CCGGGAAATC  TGGGCTGAAA  CACGGCTGGT  ACTGATGGCC      360
ACAGACAGAG  GAAGCCCAGC  ATTGGTGGGC  TCAGCTACCC  TGACAGTGAT  GGTCATCGAT      420
ACCAACGACA  ATGCTCCCCT                                                     440
```

( 2 ) INFORMATION FOR SEQ ID NO:38:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

```
        Lys  Gly  Val  Asp  Tyr  Glu  Thr  Asn  Pro  Arg  Leu  Arg  Leu  Val  Leu  Gln
        1                 5                        10                      15

Ala  Glu  Ser  Gly  Gly  Ala  Phe  Ala  Phe  Ser  Val  Leu  Thr  Leu  Thr  Leu
                       20                  25                      30

Gln  Asp  Ala  Asn  Asp  Asn  Ala  Pro  Arg  Phe  Leu  Gln  Pro  His  Tyr  Val
                  35                      40                 45

Ala  Phe  Leu  Pro  Glu  Ser  Arg  Pro  Leu  Glu  Gly  Pro  Leu  Leu  Gln  Val
             50                       55                 60

Glu  Ala  Asn  Asp  Leu  Asp  Gln  Gly  Ser  Gly  Gln  Ile  Ser  Tyr  Ser
        65                 70                      75                      80

Leu  Ala  Ala  Ser  Gln  Pro  Ala  Arg  Gly  Leu  Phe  His  Val  Asp  Pro  Ala
                            85                       90                      95

Thr  Gly  Thr  Ile  Thr  Thr  Thr  Ala  Ile  Leu  Asp  Arg  Glu  Ile  Trp  Ala
                       100                      105                 110

Glu  Thr  Arg  Leu  Val  Leu  Met  Ala  Thr  Asp  Arg  Gly  Ser  Pro  Ala  Leu
                  115                      120                 125

Val  Gly  Ser  Ala  Thr  Leu  Thr  Val  Met  Val  Ile  Asp  Thr  Asn  Asp  Asn
             130                 135                      140

Ala  Pro
        145
```

( 2 ) INFORMATION FOR SEQ ID NO:39:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
AAGGTCTCGA  TTATGAGGCA  ACTCCATATT  ATAACGTGGA  AATTGTAGCC  ACAGATGGTG      60
GGGGCCTTTC  AGGAAAATGC  ACTGTGGCTA  TAGAAGTGGT  GGATGTGAAC  GACGGCGCTC     120
CAAT                                                                      124
```

( 2 ) INFORMATION FOR SEQ ID NO:40:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

```
Lys  Gly  Leu  Asp  Tyr  Glu  Ala  Thr  Pro  Tyr  Tyr  Asn  Val  Glu  Ile  Val
 1                    5                           10                          15

Ala  Thr  Asp  Gly  Gly  Ala  Phe  Asp  Glu  Asn  Cys  Thr  Val  Ala  Ile  Glu
                20                       25                       30

Val  Val  Asp  Val  Asn  Asp  Asn  Ala  Pro
                35                       40
```

( 2 ) INFORMATION FOR SEQ ID NO:41:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

```
Asp  Xaa  Asn  Glu  Xaa  Pro  Xaa  Phe
 1                    5
```

( 2 ) INFORMATION FOR SEQ ID NO:42:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

```
Asp  Xaa  Asp  Glu  Xaa  Pro  Xaa  Phe
 1                    5
```

( 2 ) INFORMATION FOR SEQ ID NO:43:

( i ) SEQUENCE CHARACTERISTICS:
        ( A ) LENGTH: 9 amino acids
        ( B ) TYPE: amino acid ( C ) STRANDEDNESS: single
( D ) TOPOLOGY: linear ( i i ) MOLECULE TYPE: DNA ( x i ) SEQUENCE DESCRIPTION: SEQ ID NO:43:

Asp Xaa Asn Asp Asn Xaa Pro Xaa Phe
1               5

( 2 ) INFORMATION FOR SEQ ID NO:44:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:44:

| | | | | | |
|---|---|---|---|---|---|
| AAGCGGATGG | ATTTTGAAGA | CACCAAACTC | CATGAGATTT | ACATCCAGGC | CAAAGACAAA | 60 |
| GGTGCCAATC | CCGAAGGAGC | GCATTGCAAA | GTACTTGTAG | AGGTTGTAGA | CGTAAACGAC | 120 |
| AACGCCCCAG | T | | | | | 131 |

( 2 ) INFORMATION FOR SEQ ID NO:45:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:45:

Leu Arg Met Asp Phe Glu Asp Thr Lys Leu His Glu Ile Tyr Ile Gln
1               5                   10                  15

Ala Lys Asp Lys Gly Ala Asn Pro Glu Gly Ala His Cys Lys Val Leu
                20                  25                  30

Val Glu Val Val Asp Val Asn Asp Asn Ala Pro
            35                  40

( 2 ) INFORMATION FOR SEQ ID NO:46:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:46:

| | | | | | |
|---|---|---|---|---|---|
| AAGGCTTTGG | ATTACGAGGA | TCAGAGAGAG | TTCCAACTAA | CAGCTCATAT | AAACGACGGA | 60 |
| GGTACCCCAG | TCTTAGCCAC | CAACATCAGC | GTGAACGTAT | TTGTTACTGA | CCGCAATGAT | 120 |
| AACGCCCCCT | A | | | | | 131 |

( 2 ) INFORMATION FOR SEQ ID NO:47:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:47:

```
Lys Ala Leu Asp Tyr Glu Asp Gln Arg Glu Phe Gln Leu Thr Ala His
1               5                   10                      15

Ile Asn Asp Gly Gly Thr Pro Val Leu Ala Thr Asn Ile Ser Val Asn
                20                  25                  30

Val Phe Val Thr Asp Arg Asn Asp Asn Ala Pro
        35                  40
```

( 2 ) INFORMATION FOR SEQ ID NO:48:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

```
AAGCGCTTGG ACTACGAGGA GAGTAACAAT TATGAAATTC ACGTGGATGC TACAGATAAA    60
GGATACCCAC CTATGGTTGC TCACTGCACC GTACTCGTGG GAATCTTGGA TGAAAATGAC   120
AACGCACCCA T                                                        131
```

( 2 ) INFORMATION FOR SEQ ID NO:49:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:49:

```
Lys Arg Leu Asp Tyr Glu Glu Ser Asn Asn Tyr Glu Ile His Val Asp
1               5                   10                      15

Ala Thr Asp Lys Gly Tyr Pro Pro Met Val Ala His Cys Thr Val Leu
                20                  25                  30

Val Gly Ile Leu Asp Glu Asn Asp Asn Ala Pro
        35                  40
```

( 2 ) INFORMATION FOR SEQ ID NO:50:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

```
AAACCGGTGG ACTACGAGAA AGTCAAAGAC TATACCATCG AGATCGTGGC TGTGGATTCC    60
GGCAACCCTC CACTCTCTAG CACCAACTCC CTCAAGGTGC AGGTGGTAGA CGTCAACGAT   120
AACGCCCCTC T                                                        131
```

( 2 ) INFORMATION FOR SEQ ID NO:51:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear 5,663,300

43                                                                                      44

-continued ( i i ) MOLECULE TYPE: protein ( x i ) SEQUENCE DESCRIPTION: SEQ ID NO:51:

Lys Pro Val Asp Tyr Glu Lys Val Lys Asp Tyr Thr Ile Glu Ile Val
1               5                   10                  15

Ala Val Asp Ser Gly Asn Pro Pro Leu Ser Ser Thr Asn Ser Leu Lys
            20                  25                  30

Val Gln Val Val Asp Val Asn Asp Asn Ala Pro
        35                  40

( 2 ) INFORMATION FOR SEQ ID NO:52:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

AAGCCTTTTG ATTTCGAGGA CACCAAACTC CATGAGATTT ACATCCAGGC CAAAGACAAG      60

GGCGCCAATC CGAAGGAGC ACATTGCAAA GTGTTGGTGG AGGTTGTGGA TGTGAACGAC       120

AATGCCCCTC A                                                          131

( 2 ) INFORMATION FOR SEQ ID NO:53:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:53:

Lys Pro Phe Asp Phe Glu Asp Thr Lys Leu His Glu Ile Tyr Ile Gln
1               5                   10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
        35                  40

( 2 ) INFORMATION FOR SEQ ID NO:54:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

AAAGGTGTCG ATTACGAGGT GAGTCCACGG CTGCGACTGG TGCTGCAGGC AGAGAGTCGA      60

GGAGCCTTTG CCTTCACTGT GCTGACCCTG ACCCTGCAAG ATGCCAACGA CAACGCCCCG     120

AG                                                                    122

( 2 ) INFORMATION FOR SEQ ID NO:55:

( i ) SEQUENCE CHARACTERISTICS:
        ( A ) LENGTH: 40 amino acids
        ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:55:

```
Lys Gly Val Asp Tyr Glu Val Ser Pro Arg Leu Arg Leu Val Leu Gln
1               5                   10                  15

Ala Glu Ser Arg Gly Ala Phe Ala Phe Thr Val Leu Thr Leu Thr Leu
            20                  25                  30

Gln Asp Ala Asn Asp Asn Ala Pro
        35                  40
```

( 2 ) INFORMATION FOR SEQ ID NO:56:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:56:

```
AAAGGGATTG ATTACGAGCA GTTGAGAGAC CTACAGCTGT GGGTGACAGC CAGCGACAGC        60
GGGGACCCGC CTCTTAGCAG CAACGTGTCA CTGAGCCTGT TGTGCTGGA CCAGAACGAC       120
AACGCCCCCC T                                                            131
```

( 2 ) INFORMATION FOR SEQ ID NO:57:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:57:

```
Lys Gly Ile Asp Tyr Glu Gln Leu Arg Asp Leu Gln Leu Trp Val Thr
1               5                   10                  15

Ala Ser Asp Ser Gly Asp Pro Pro Leu Ser Ser Asn Val Ser Leu Ser
            20                  25                  30

Leu Phe Val Leu Asp Gln Asn Asp Asn Ala Pro
        35                  40
```

( 2 ) INFORMATION FOR SEQ ID NO:58:

( i ) SEQUENCE CHARACTERISTICS:
( A ) LENGTH: 125 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:58:

```
AAGGCGGTCG ATTTTGAGCG CACATCCTCT TATCAACTCA TCATTCAGGC CACCAATATG        60
GCAGGAATGG CTTCCAATGC TACAGTCAAT ATTCAGATTG TTGATGAAAA CGACAACGCC       120
CCCCA                                                                   125
```

( 2 ) INFORMATION FOR SEQ ID NO:59:

( i ) SEQUENCE CHARACTERISTICS:

( A ) LENGTH: 41 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:59:

| Lys | Ala | Val | Asp | Phe | Glu | Arg | Thr | Ser | Ser | Tyr | Gln | Leu | Ile | Ile | Gln |
|---|---|---|---|---|---|---|---|---|---|---|---|---|---|---|---|
| 1 | | | | 5 | | | | | 10 | | | | | 15 | |
| Ala | Thr | Asn | Met | Ala | Gly | Met | Ala | Ser | Asn | Ala | Thr | Val | Asn | Ile | Gln |
| | | | 20 | | | | | 25 | | | | | 30 | | |
| Ile | Val | Asp | Glu | Asn | Asp | Asn | Ala | Pro | | | | | | | |
| | | | 35 | | | | | 40 | | | | | | | |

( 2 ) INFORMATION FOR SEQ ID NO:60:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:60:

```
AAACGGCTAG ACTTTGAAAA GATACAAAAA TATGTTGTAT GGATAGAGGC CAGAGATGGT      60
GGTTTCCCTC CTTTCTCCTC TTACGAGAAA CTTGATATAA CAGTATTAGA TGTCAACGAT     120
AACGCGCCTA A                                                          131
```

( 2 ) INFORMATION FOR SEQ ID NO:61:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:61:

| Lys | Arg | Leu | Asp | Phe | Glu | Lys | Ile | Gln | Lys | Tyr | Val | Val | Trp | Ile | Glu |
|---|---|---|---|---|---|---|---|---|---|---|---|---|---|---|---|
| 1 | | | | 5 | | | | | 10 | | | | | 15 | |
| Ala | Arg | Asp | Gly | Gly | Phe | Pro | Pro | Phe | Ser | Ser | Tyr | Glu | Lys | Leu | Asp |
| | | | 20 | | | | | 25 | | | | | 30 | | |
| Ile | Thr | Val | Leu | Asp | Val | Asn | Asp | Asn | Ala | Pro | | | | | |
| | | | 35 | | | | | 40 | | | | | | | |

( 2 ) INFORMATION FOR SEQ ID NO:62:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:62:

```
AAGGGGATCG ATTATGAGAA GGTCAAAGAC TACACCATTG AGATTGTGGC TGTGGACTCT      60
GGCAACCCCC CACTCTCCAG CACTAACTCC CTCAAGGTGC AGGTGGTGGA CGTCAATGAC     120
AACGCACCGT G                                                          131
```

( 2 ) INFORMATION FOR SEQ ID NO:63:

(i) SEQUENCE CHARACTERISTICS:
  (A) LENGTH: 43 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:63:

| Lys | Gly | Ile | Asp | Tyr | Glu | Lys | Val | Lys | Asp | Tyr | Thr | Ile | Glu | Ile | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Val | Asp | Ser | Gly | Asn | Pro | Pro | Leu | Ser | Ser | Thr | Asn | Ser | Leu | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Gln | Val | Val | Asp | Val | Asn | Asp | Asn | Ala | Pro |
|-----|-----|-----|-----|-----|-----|-----|-----|-----|-----|-----|
|     |     | 35  |     |     |     |     | 40  |     |     |     |

(2) INFORMATION FOR SEQ ID NO:64:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:64:

```
AAGGGACTCG ACTACGAGGA TCGGCGGGAA TTTGAATTAA CAGCTCATAT CAGCGATGGG      60
GGCACCCCGG TCCTAGCCAC CAACATCAGC GTGAACATAT TTGTCACTGA TCGCAACGAT     120
AATGCCCCCG T                                                          131
```

(2) INFORMATION FOR SEQ ID NO:65:

(i) SEQUENCE CHARACTERISTICS:
    (A) LENGTH: 43 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:65:

| Lys | Gly | Leu | Asp | Tyr | Glu | Asp | Arg | Arg | Glu | Phe | Glu | Leu | Thr | Ala | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Ser | Asp | Gly | Gly | Thr | Pro | Val | Leu | Ala | Thr | Asn | Ile | Ser | Val | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | Phe | Val | Thr | Asp | Arg | Asn | Asp | Asn | Ala | Pro |
|-----|-----|-----|-----|-----|-----|-----|-----|-----|-----|-----|
|     |     | 35  |     |     |     |     | 40  |     |     |     |

(2) INFORMATION FOR SEQ ID NO:66:

(i) SEQUENCE CHARACTERISTICS:
    (A) LENGTH: 470 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:66:

```
AAGGGTTTGG ACTACGAGAC CACACAGGCC TACCAGCTCA CGGTCAACGC CACAGATCAA      60
GACAACACCA GGCCTCTGTC CACCCTGGCC AACTTGGCCA TCATCATCAC AGATGTCCAG     120
GACATGGACC CCATCTTCAT CAACCTGCCT TACAGCACCA ACATCTACGA GCATTCTCCT     180
```

```
CCGGGCACGA CGGTGCGCAT CATCACCGCC ATAGACCAGG ATCAAGGACG TCCCCGGGGC       240

ATTGGCTACA CCATCGTTTC AGGGAATACC AACAGCATCT TTGCCCTGGA CTACATCAGC       300

GGAGTGCTGA CCTTGAATGG CCTGCTGGAC CGGGAGAACC CCCTGTACAG CCATGGCTTC       360

ATCCTGACTG TGAAGGGCAC GGAGCTGAAC GATGACCGCA CCCCATCTGA CGCTACAGTC       420

ACCACGACCT TCAATATCCT GGTTATTGAC ATCAACGACA ACGCCCCACT                  470
```

(2) INFORMATION FOR SEQ ID NO:67:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:67:

```
Lys Gly Leu Asp Tyr Glu Thr Thr Gln Ala Tyr Gln Leu Thr Val Asn
 1               5                  10                  15

Ala Thr Asp Gln Asp Asn Thr Arg Pro Leu Ser Thr Leu Ala Asn Leu
            20                  25                  30

Ala Ile Ile Ile Thr Asp Val Gln Asp Met Asp Pro Ile Phe Ile Asn
        35                  40                  45

Leu Pro Tyr Ser Thr Asn Ile Tyr Glu His Ser Pro Gly Thr Thr
    50                  55                  60

Val Arg Ile Ile Thr Ala Ile Asp Gln Asp Gln Gly Arg Pro Arg Gly
65                  70                  75                  80

Ile Gly Tyr Thr Ile Val Ser Gly Asn Thr Asn Ser Ile Phe Ala Leu
                85                  90                  95

Asp Tyr Ile Ser Gly Val Leu Thr Leu Asn Gly Leu Leu Asp Arg Glu
                100                 105                 110

Asn Pro Leu Tyr Ser Gly Gly Phe Ile Leu Thr Val Lys Gly Thr Glu
            115                 120                 125

Leu Asn Asp Asp Arg Thr Pro Ser Asp Ala Thr Val Thr Thr Thr Phe
    130                 135                 140

Asn Ile Leu Val Ile Asp Ile Asn Asp Asn Ala Pro
145                 150                 155
```

(2) INFORMATION FOR SEQ ID NO:68:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

```
AAGGGGGTCG ATTACGAGGT ACTACAGGCC TTTGAGTTCC ACGTGAGCGC CACAGACCGA       60

GGCTCACCGG GGCTCAGCAG CCAGGCTCTG GTGCGCGTGG TGGTGCTGGA CGACAATGAC      120

AACGCTCCCG T                                                           131
```

(2) INFORMATION FOR SEQ ID NO:69:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:69:

Lys Gly Val Asp Tyr Glu Val Leu Gln Ala Phe Glu Phe His Val Ser
1               5                   10                  15

Ala Thr Asp Arg Gly Ser Pro Gly Leu Ser Ser Gln Ala Leu Val Arg
            20                  25                  30

Val Val Val Leu Asp Asp Asn Asp Asn Ala Pro
        35                  40

(2) INFORMATION FOR SEQ ID NO:70:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:70:

```
AAGGGGCTGG ATTATGAGCA GTTCCAGACC CTACAACTGG GAGTGACCGC TAGTGACAGT      60
GGAAACCCAC CATTAAGAAG CAATATTTCA CTGACCCTTT TCGTGCTGGA CCAGAATGAT     120
AACGCCCCAA A                                                         131
```

(2) INFORMATION FOR SEQ ID NO:71:

(i) SEQUENCE CHARACTERISTICS:
    (A) LENGTH: 43 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:71:

Lys Gly Leu Asp Tyr Glu Gln Phe Gln Thr Leu Gln Leu Gly Val Thr
1               5                   10                  15

Ala Ser Asp Ser Gly Asn Pro Pro Leu Arg Ser Asn Ile Ser Leu Thr
            20                  25                  30

Leu Phe Val Leu Asp Gln Asn Asp Asn Ala Pro
        35                  40

(2) INFORMATION FOR SEQ ID NO:72:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:72:

```
AAGCGGGTTG ATTACGAGGA TGTCCAGAAA TACTCGCTGA GCATTAAGGC CCAGGATGGG      60
CGGCCCCCGC TCATCAATTC TTCAGGGGTG GTGTCTGTGC AGGTGCTGGA TGTCAACGAC     120
AATGCCCCGG A                                                         131
```

(2) INFORMATION FOR SEQ ID NO:73:

(i) SEQUENCE CHARACTERISTICS:
    (A) LENGTH: 43 amino acids
    (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:73:

Lys Arg Val Asp Tyr Glu Asp Val Gln Lys Tyr Ser Leu Ser Ile Lys
1               5                   10                  15

Ala Gln Asp Gly Arg Pro Pro Leu Ile Asn Ser Ser Gly Val Val Ser
            20                  25                  30

Val Gln Val Leu Asp Val Asn Asp Asn Ala Pro
        35                  40

( 2 ) INFORMATION FOR SEQ ID NO:74:

( i ) SEQUENCE CHARACTERISTICS:
    ( A ) LENGTH: 125 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:74:

AAACCGGTAG ACTTTGAGCT ACAGCAGTTC TATGAAGTAG CTGTGGTGGC TTGGAACTCT        60

GAGGGATTTC ATGTCAAAAG GGTCATTAAA GTGCAACTTT TAGATGACAA CGACAATGCC       120

CCGAT                                                                    125

( 2 ) INFORMATION FOR SEQ ID NO:75:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:75:

Lys Pro Val Asp Phe Glu Leu Gln Gln Phe Tyr Glu Val Ala Val Val
1               5                   10                  15

Ala Trp Asn Ser Glu Gly Phe His Val Lys Arg Val Ile Lys Val Gln
            20                  25                  30

Leu Leu Asp Asp Asn Asp Asn Ala Pro
        35                  40

( 2 ) INFORMATION FOR SEQ ID NO:76:

( i ) SEQUENCE CHARACTERISTICS:
    ( A ) LENGTH: 125 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:76:

AAGGGATTAG ATTTTGAAAC TTTGCCCATT TACACATTGA TAATACAAGG AACTAACATG        60

GCTGGTTTGT CCACTAATAC AACGGTTCTA GTTCACTTGC AGGATGAGAA TGATAACGCC       120

CCAAA                                                                    125

( 2 ) INFORMATION FOR SEQ ID NO:77:

( i ) SEQUENCE CHARACTERISTICS:

( A ) LENGTH: 41 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:77:

```
Lys Gly Leu Asp Phe Glu Thr Leu Pro Ile Tyr Thr Leu Ile Ile Gln
1               5                   10                  15

Gly Thr Asn Met Ala Gly Leu Ser Thr Asn Thr Thr Val Leu Val His
            20                  25                  30

Leu Gln Asp Glu Asn Asp Asn Ala Pro
            35                  40
```

( 2 ) INFORMATION FOR SEQ ID NO:78:

( i ) SEQUENCE CHARACTERISTICS:
( A ) LENGTH: 134 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:78:

| | | | | | | |
|---|---|---|---|---|---|---|
| AAGCGGGCGG | ATTTCGAGGC | GATCCGGGAG | TACAGTCTGA | GGATCAAAGC | GCAGGACGGG | 60 |
| GGGCGGCCTC | CCCTCAGCAA | CACCACGGGC | ATGGTCACAG | TGCAGGTCGT | GGACGTCAAT | 120 |
| GACAACGCAC | CCCT | | | | | 134 |

( 2 ) INFORMATION FOR SEQ ID NO:79:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:79:

```
Lys Arg Ala Asp Phe Glu Ala Ile Arg Glu Tyr Ser Leu Arg Ile Lys
1               5                   10                  15

Ala Gln Asp Gly Gly Arg Pro Pro Leu Ser Asn Thr Thr Gly Met Val
            20                  25                  30

Thr Val Gln Val Val Asp Val Asn Asp Asn Ala Pro
            35                  40
```

( 2 ) INFORMATION FOR SEQ ID NO:80:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:80:

| | | | | | | |
|---|---|---|---|---|---|---|
| AAGCGGTTGG | ATTACGAAAA | GGCATCGGAA | TATGAAATCT | ATGTTCAAGC | CGCTGACAAA | 60 |
| GGCGCTGTCC | CTATGGCTGG | CCATTGCAAA | GTGTTGCTGG | AGATCGTGGA | TGTCAACGAC | 120 |
| AACGCCCCCT | T | | | | | 131 |

( 2 ) INFORMATION FOR SEQ ID NO:81:

( i ) SEQUENCE CHARACTERISTICS:
   ( A ) LENGTH: 43 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:81:

Lys Arg Leu Asp Tyr Glu Lys Ala Ser Glu Tyr Glu Ile Tyr Val Gln
1               5                   10                  15

Ala Ala Asp Lys Gly Ala Val Pro Met Ala Gly His Cys Lys Val Leu
            20                  25                  30

Leu Glu Ile Val Asp Val Asn Asp Asn Ala Pro
            35                  40

( 2 ) INFORMATION FOR SEQ ID NO:82:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:82:

```
AAGGGGATCG ATTATGAGGA TCAGGTCTCT TACACATTAG CAGTAACAGC ACATGACTAT     60
GGCATCCCTC AAAAATCAGA CACTACCTAT TTGGAAATCT TAGTAATTGA TGTTAACGAC    120
AACGCGCCCC A                                                         131
```

( 2 ) INFORMATION FOR SEQ ID NO:83:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:83:

Lys Gly Ile Asp Tyr Glu Asp Gln Val Ser Tyr Thr Leu Ala Val Thr
1               5                   10                  15

Ala His Asp Tyr Gly Ile Pro Gln Lys Ser Asp Thr Thr Tyr Leu Glu
            20                  25                  30

Ile Leu Val Ile Asp Val Asn Asp Asn Ala Pro
            35                  40

( 2 ) INFORMATION FOR SEQ ID NO:84:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:84:

```
AAAGGGTTAG ATTTCGAGGG CACTAAAGAT TCAGCGTTTA AAATAGTGGC AGCTGACACA     60
GGGAAGCCCA GCCTCAACCA GACAGCCCTG GTGAGAGTAG AGCTGGAGGA TGAGAACGAC    120
AACGCCCCAA T                                                         131
```

( 2 ) INFORMATION FOR SEQ ID NO:85:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:85:

```
Lys Gly Leu Asp Phe Glu Gly Thr Lys Asp Ser Ala Phe Lys Ile Val
1               5                   10                  15

Ala Ala Asp Thr Gly Lys Pro Ser Leu Asn Gln Thr Ala Leu Val Arg
            20              25                  30

Val Glu Leu Glu Asp Glu Asn Asp Asn Ala Pro
        35              40
```

( 2 ) INFORMATION FOR SEQ ID NO:86:

( i ) SEQUENCE CHARACTERISTICS:
    ( A ) LENGTH: 130 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:86:

```
AAGGGTGTGG ATTTTGAAAG TGTGCGTAGC TACAGGCTGG TTATTCGTGC TCAAGATGGA      60

GGCAGCCCCT CCAGAAGTAA CACCACCCAG CTCTTGGTCA ACGTCATCGA TCGAATGACA      120

ATGCGCCGCT                                                             130
```

( 2 ) INFORMATION FOR SEQ ID NO:87:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:87:

```
Lys Gly Val Asp Phe Glu Ser Val Arg Ser Tyr Arg Leu Val Ile Arg
1               5                   10                  15

Ala Gln Asp Gly Gly Ser Pro Ser Arg Ser Asn Thr Thr Gln Leu Leu
            20              25                  30

Val Asn Val Ile Asp Val Asn Asp Asn Ala Pro
        35              40
```

( 2 ) INFORMATION FOR SEQ ID NO:88:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:88:

```
AAGGGTGTGG ACTTCGAGCT GACACATCTG TATGAGATTT GGATTGAGGC TGCCGATGGA      60

GACACGCCAA GTCTGCGTAG TGTAACTCTT ATAACGCTCA ACGTAACGGA TGCCAATGAC      120
```

AATGCTCCCA A 131

(2) INFORMATION FOR SEQ ID NO:89:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:89:

```
Lys Gly Val Asp Phe Glu Leu Thr His Leu Tyr Glu Ile Trp Ile Glu
 1               5                  10                  15
Ala Ala Asp Gly Asp Thr Pro Ser Leu Arg Ser Val Thr Leu Ile Thr
            20                  25                  30
Leu Asn Val Thr Asp Ala Asn Asp Asn Ala Pro
            35                  40
```

(2) INFORMATION FOR SEQ ID NO:90:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:90:

```
CAAGGCGTTT GATTTGAAG AGACAAGTAG ATATGTGTTG AGTGTGGAAG CTAAGGATGG      60
AGGAGTACAC ACAGCTCACT GTAATGTTCA AATAGAAATT GTTGACGAGA ATGACAATGC    120
CCCAGAGGTG ACATTCATGT CCTTCTCTAA CCAGATTCCA GAGGATTCAG ACCTTGGAAC    180
TGTAATAGCC CTCATAAAAG TGCGAGACAA GGATTCTGGG CAAAATGGCA TGGTGACATG    240
CTATACTCAG GAAGAAGTTC CTTTCAAATT AGAATCCACC TCGAAGAATT ATTACAAGCT    300
GGTGATTGCT GGAGCCCTAA ACCGGGAGCA GACAGCAGAC TACAACGTCA CAATCATAGC    360
CACCGACAAG GGCAAACCAG CCCTTTCCTC CAGGACAAGC ATCACCCTGC ACATCTCCGA    420
CATCAACGAT AATGCCCCCG T                                              441
```

(2) INFORMATION FOR SEQ ID NO:91:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:91:

```
Lys Ala Phe Asp Phe Glu Glu Thr Ser Arg Tyr Val Leu Ser Val Glu
 1               5                  10                  15
Ala Lys Asp Gly Gly Val His Thr Ala His Cys Asn Val Gln Ile Glu
            20                  25                  30
Ile Val Asp Glu Asn Asp Asn Ala Pro Glu Val Thr Phe Met Ser Phe
            35                  40                  45
Ser Asn Gln Ile Pro Glu Asp Ser Asp Leu Gly Thr Val Ile Ala Leu
            50                  55                  60
Ile Lys Val Arg Asp Lys Asp Ser Gly Gln Asn Gly Met Val Thr Cys
65                  70                  75                  80
```

5,663,300

65

66

-continued

```
Tyr  Thr  Gln  Glu  Glu  Val  Pro  Phe  Lys  Leu  Glu  Ser  Thr  Ser  Lys  Asn
               85                      90                      95

Tyr  Tyr  Lys  Leu  Val  Ile  Ala  Gly  Ala  Leu  Asn  Arg  Glu  Gln  Thr  Ala
               100                     105                     110

Asp  Tyr  Asn  Val  Thr  Ile  Ile  Ala  Thr  Asp  Lys  Gly  Lys  Pro  Ala  Leu
               115                     120                     125

Ser  Ser  Arg  Thr  Ser  Ile  Thr  Leu  His  Ile  Ser  Asp  Ile  Asn  Asp  Asn
               130                     135                     140

Ala  Pro
145
```

( 2 ) INFORMATION FOR SEQ ID NO:92:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:92:

```
AAGCGAGTGG ATTACGAGGC CACTCGGAAT TATAAGCTGA GAGTTAAGGC TACTGATCTT      60

GGGATTCCAC CGAGATCTTC TAACATGACA CTGTTCATTC ATGTCCTTGA TGTTAACGAC     120

AACGCTCCCT T                                                          131
```

( 2 ) INFORMATION FOR SEQ ID NO:93:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:93:

```
Lys  Arg  Val  Asp  Tyr  Glu  Ala  Thr  Arg  Asn  Tyr  Lys  Leu  Arg  Val  Lys
1                   5                        10                      15

Ala  Thr  Asp  Leu  Gly  Ile  Pro  Pro  Arg  Ser  Ser  Asn  Met  Thr  Leu  Phe
               20                       25                      30

Ile  His  Val  Leu  Asp  Val  Asn  Asp  Asn  Ala  Pro
               35                       40
```

( 2 ) INFORMATION FOR SEQ ID NO:94:

( i ) SEQUENCE CHARACTERISTICS:
        ( A ) LENGTH: 4104 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 495..3572

( x i ) SEQUENCE DESCRIPTION: SEQ ID NO:94:

```
CCTCTATTCG ACATTCTCTT TGGATTGTTT TGCTATAACT TGAAATTTGG GATGTCACAA      60

ACGAAACTGT CATCTGTTTC CGCCAAACTG TGGTTCTGCT AATCTCCCAG GCTGGCAGCA     120

TTGGAGACTT GCTGACTTCT TTCATCCCCC ACTCTTTTCA CCTGAAATTC CTTTCCTTGG     180
```

-continued

| | | | | | |
|---|---|---|---|---|---|
| TTTTGCTCTA | AGTCCTATGC | TTCAGTCAGG | GGCCAACCAA | ATCTCACTGC | CTCCTTTTTA | 240 |
| TCATGAAGCC | TTTGATCACT | GATAGTTCTT | TTTATATCTT | GAAAAATCAC | CCTTCCCAGT | 300 |
| ACAGTTAATA | TTTAGTATCT | CTACTCATCT | TGGCACTTAC | TCACAGCTCC | ATAATTCAGT | 360 |
| CGTTTTCGTA | CCTCTTCATG | GTGATGGGGA | GCCCTTTGGA | GGTGGTGACT | GTGCTTTATA | 420 |
| CTCCTCATGA | TGCTTCACAT | GTGGCAGGCG | TGGAGTGCCC | GGAGGCGGCC | CTCCTGATTC | 480 |
| TGGGGCCTCC | CAGG ATG GAG | CCC CTG AGG | CAC AGC CCA | GGC CCT GGG GGG | | 530 |
| | Met Glu<br>1 | Pro Leu Arg<br>5 | His Ser Pro | Gly Pro Gly Gly<br>10 | |

```
CAA CGG CTA CTG CTG CCC TCC ATG CTG CTA GCA CTG CTG CTC CTG CTG      578
Gln Arg Leu Leu Leu Pro Ser Met Leu Leu Ala Leu Leu Leu Leu Leu
         15                  20                  25

GCT CCA TCC CCA GGC CAC GCC ACT CGG GTA GTG TAC AAG GTG CCG GAG      626
Ala Pro Ser Pro Gly His Ala Thr Arg Val Val Tyr Lys Val Pro Glu
         30                  35                  40

GAA CAG CCA CCC AAC ACC CTC ATT GGG AGC CTC GCA GCC GAC TAT GGT      674
Glu Gln Pro Pro Asn Thr Leu Ile Gly Ser Leu Ala Ala Asp Tyr Gly
45                  50                  55                  60

TTT CCA GAT GTG GGG CAC CTG TAC AAG CTA GAG GTG GGT GCC CCG TAC      722
Phe Pro Asp Val Gly His Leu Tyr Lys Leu Glu Val Gly Ala Pro Tyr
                 65                  70                  75

CTT CGC GTG GAT GGC AAG ACA GGT GAC ATT TTC ACC ACC GAG ACC TCC      770
Leu Arg Val Asp Gly Lys Thr Gly Asp Ile Phe Thr Thr Glu Thr Ser
         80                  85                  90

ATC GAC CGT GAG GGG CTC CGT GAA TGC CAG AAC CAG CTC CCT GGT GAT      818
Ile Asp Arg Glu Gly Leu Arg Glu Cys Gln Asn Gln Leu Pro Gly Asp
         95                 100                 105

CCC TGC ATC CTG GAG TTT GAG GTA TCT ATC ACA GAC CTC GTG CAG AAT      866
Pro Cys Ile Leu Glu Phe Glu Val Ser Ile Thr Asp Leu Val Gln Asn
    110                 115                 120

GCG AGC CCC CGG CTG CTA GAG GGC CAG ATA GAA GTA CAA GAC ATC AAT      914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT      962
Asp Asn Thr Pro Asn Phe Ala Ser Pro Val Ile Thr Leu Ala Ile Pro
                145                 150                 155

GAG AAC ACC AAC ATC GGC TCA CTC TTC CCC ATC CCG CTG GCT TCA GAC     1010
Glu Asn Thr Asn Ile Gly Ser Leu Phe Pro Ile Pro Leu Ala Ser Asp
                160                 165                 170

CGT GAT GCT GGT CCC AAC GGT GTG GCA TCC TAT GAG CTG CAG GTG GCA     1058
Arg Asp Ala Gly Pro Asn Gly Val Ala Ser Tyr Glu Leu Gln Val Ala
        175                 180                 185

GAG GAC CAG GAG GAG AAG CAA CCA CAG CTC ATT GTG ATG GGC AAC CTG     1106
Glu Asp Gln Glu Glu Lys Gln Pro Gln Leu Ile Val Met Gly Asn Leu
        190                 195                 200

GAC CGT GAG CGC TGG GAC TCC TAT GAC CTC ACC ATC AAG GTG CAG GAT     1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG     1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG     1250
Leu Asp Thr Asn Asp Asn Ala Pro Lys Phe Glu Arg Pro Ser Tyr Glu
        240                 245                 250

GCC GAA CTA TCT GAG AAT AGC CCC ATA GGC CAC TCG GTC ATC CAG GTG     1298
Ala Glu Leu Ser Glu Asn Ser Pro Ile Gly His Ser Val Ile Gln Val
        255                 260                 265

AAG GCC AAT GAC TCA GAC CAA GGT GCC AAT GCA GAA ATC GAA TAC ACA     1346
```

```
Lys  Ala  Asn  Asp  Ser  Asp  Gln  Gly  Ala  Asn  Ala  Glu  Ile  Glu  Tyr  Thr
     270                 275                 280

TTC  CAC  CAG  GCG  CCC  GAA  GTT  GTG  AGG  CGT  CTT  CTT  CGA  CTG  GAC  AGG      1394
Phe  His  Gln  Ala  Pro  Glu  Val  Val  Arg  Arg  Leu  Leu  Arg  Leu  Asp  Arg
285                 290                 295                 300

AAC  ACT  GGA  CTT  ATC  ACT  GTT  CAG  GGC  CCG  GTG  GAC  CGT  GAG  GAC  CTA      1442
Asn  Thr  Gly  Leu  Ile  Thr  Val  Gln  Gly  Pro  Val  Asp  Arg  Glu  Asp  Leu
               305                 310                 315

AGC  ACC  CTG  CGC  TTC  TCA  GTG  CTT  GCT  AAG  GAC  CGA  GGC  ACC  AAC  CCC      1490
Ser  Thr  Leu  Arg  Phe  Ser  Val  Leu  Ala  Lys  Asp  Arg  Gly  Thr  Asn  Pro
               320                 325                 330

AAG  AGT  GCC  CGT  GCC  CAG  GTG  GTT  GTG  ACC  GTG  AAG  GAC  ATG  AAT  GAC      1538
Lys  Ser  Ala  Arg  Ala  Gln  Val  Val  Val  Thr  Val  Lys  Asp  Met  Asn  Asp
          335                 340                 345

AAT  GCC  CCC  ACC  ATT  GAG  ATC  CGG  GGC  ATA  GGG  CTA  GTG  ACT  CAT  CAA      1586
Asn  Ala  Pro  Thr  Ile  Glu  Ile  Arg  Gly  Ile  Gly  Leu  Val  Thr  His  Gln
     350                 355                 360

GAT  GGG  ATG  GCT  AAC  ATC  TCA  GAG  GAT  GTG  GCA  GAG  GAG  ACA  GCT  GTG      1634
Asp  Gly  Met  Ala  Asn  Ile  Ser  Glu  Asp  Val  Ala  Glu  Glu  Thr  Ala  Val
365                 370                 375                 380

GCC  CTG  GTG  CAG  GTG  TCT  GAC  CGA  GAT  GAG  GGA  GAG  AAT  GCA  GCT  GTC      1682
Ala  Leu  Val  Gln  Val  Ser  Asp  Arg  Asp  Glu  Gly  Glu  Asn  Ala  Ala  Val
               385                 390                 395

ACC  TGT  GTG  GTG  GCA  GGT  GAT  GTG  CCC  TTC  CAG  CTG  CGC  CAG  GCC  AGT      1730
Thr  Cys  Val  Val  Ala  Gly  Asp  Val  Pro  Phe  Gln  Leu  Arg  Gln  Ala  Ser
               400                 405                 410

GAG  ACA  GGC  AGT  GAC  AGC  AAG  AAG  AAG  TAT  TTC  CTG  CAG  ACT  ACC  ACC      1778
Glu  Thr  Gly  Ser  Asp  Ser  Lys  Lys  Lys  Tyr  Phe  Leu  Gln  Thr  Thr  Thr
               415                 420                 425

CCG  CTA  GAC  TAC  GAG  AAG  GTC  AAA  GAC  TAC  ACC  ATT  GAG  ATT  GTG  GCT      1826
Pro  Leu  Asp  Tyr  Glu  Lys  Val  Lys  Asp  Tyr  Thr  Ile  Glu  Ile  Val  Ala
     430                 435                 440

GTG  GAC  TCT  GGC  AAC  CCC  CCA  CTC  TCC  AGC  ACT  AAC  TCC  CTC  AAG  GTG      1874
Val  Asp  Ser  Gly  Asn  Pro  Pro  Leu  Ser  Ser  Thr  Asn  Ser  Leu  Lys  Val
445                 450                 455                 460

CAG  GTG  GTG  GAC  GTC  AAT  GAC  AAC  GCA  CCT  GTC  TTC  ACT  CAG  AGT  GTC      1922
Gln  Val  Val  Asp  Val  Asn  Asp  Asn  Ala  Pro  Val  Phe  Thr  Gln  Ser  Val
               465                 470                 475

ACT  GAG  GTC  GCC  TTC  CCG  GAA  AAC  AAC  AAG  CCT  GGT  GAA  GTG  ATT  GCT      1970
Thr  Glu  Val  Ala  Phe  Pro  Glu  Asn  Asn  Lys  Pro  Gly  Glu  Val  Ile  Ala
               480                 485                 490

GAG  ATC  ACT  GCC  AGT  GAT  GCT  GAC  TCT  GGC  TCT  AAT  GCT  GAG  CTG  GTT      2018
Glu  Ile  Thr  Ala  Ser  Asp  Ala  Asp  Ser  Gly  Ser  Asn  Ala  Glu  Leu  Val
               495                 500                 505

TAC  TCT  CTG  GAG  CCT  GAG  CCG  GCT  GCT  AAG  GGC  CTC  TTC  ACC  ATC  TCA      2066
Tyr  Ser  Leu  Glu  Pro  Glu  Pro  Ala  Ala  Lys  Gly  Leu  Phe  Thr  Ile  Ser
     510                 515                 520

CCC  GAG  ACT  GGA  GAG  ATC  CAG  GTG  AAG  ACA  TCT  CTG  GAT  CGG  GAA  CAG      2114
Pro  Glu  Thr  Gly  Glu  Ile  Gln  Val  Lys  Thr  Ser  Leu  Asp  Arg  Glu  Gln
525                 530                 535                 540

CGG  GAG  AGC  TAT  GAG  TTG  AAG  GTG  GTG  GCA  GCT  GAC  CGG  GGC  AGT  CCT      2162
Arg  Glu  Ser  Tyr  Glu  Leu  Lys  Val  Val  Ala  Ala  Asp  Arg  Gly  Ser  Pro
               545                 550                 555

AGC  CTC  CAG  GGC  ACA  GCC  ACT  GTC  CTT  GTC  AAT  GTG  CTG  GAC  TGC  AAT      2210
Ser  Leu  Gln  Gly  Thr  Ala  Thr  Val  Leu  Val  Asn  Val  Leu  Asp  Cys  Asn
               560                 565                 570

GAC  AAT  GAC  CCC  AAA  TTT  ATG  CTG  AGT  GGC  TAC  AAC  TTC  TCA  GTG  ATG      2258
Asp  Asn  Asp  Pro  Lys  Phe  Met  Leu  Ser  Gly  Tyr  Asn  Phe  Ser  Val  Met
               575                 580                 585

GAG  AAC  ATG  CCA  GCA  CTG  AGT  CCA  GTG  GGC  ATG  GTG  ACT  GTC  ATT  GAT      2306
```

```
       Glu Asn Met Pro Ala Leu Ser Pro Val Gly Met Val Thr Val Ile Asp
           590             595             600

GGA GAC AAG GGG GAG AAT GCC CAG GTG CAG CTC TCA GTG GAG CAG GAC            2354
Gly Asp Lys Gly Glu Asn Ala Gln Val Gln Leu Ser Val Glu Gln Asp
605             610             615             620

AAC GGT GAC TTT GTT ATC CAG AAT GGC ACA GGC ACC ATC CTA TCC AGC            2402
Asn Gly Asp Phe Val Ile Gln Asn Gly Thr Gly Thr Ile Leu Ser Ser
                625             630             635

CTG AGC TTT GAT CGA GAG CAA CAA AGC ACC TAC ACC TTC CAG CTG AAG            2450
Leu Ser Phe Asp Arg Glu Gln Gln Ser Thr Tyr Thr Phe Gln Leu Lys
            640             645             650

GCA GTG GAT GGT GGC GTC CCA CCT CGC TCA GCT TAC GTT GGT GTC ACC            2498
Ala Val Asp Gly Gly Val Pro Pro Arg Ser Ala Tyr Val Gly Val Thr
        655             660             665

ATC AAT GTG CTG GAC GAG AAT GAC AAC GCA CCC TAT ATC ACT GCC CCT            2546
Ile Asn Val Leu Asp Glu Asn Asp Asn Ala Pro Tyr Ile Thr Ala Pro
    670             675             680

TCT AAC ACC TCT CAC AAG CTG CTG ACC CCC CAG ACA CGT CTT GGT GAG            2594
Ser Asn Thr Ser His Lys Leu Leu Thr Pro Gln Thr Arg Leu Gly Glu
685             690             695             700

ACG GTC AGC CAG GTG GCA GCC GAG GAC TTT GAC TCT GGT GTC AAT GCC            2642
Thr Val Ser Gln Val Ala Ala Glu Asp Phe Asp Ser Gly Val Asn Ala
                705             710             715

GAG CTG ATC TAC AGC ATT GCA GGT GGC AAC CCT TAT GGA CTC TTC CAG            2690
Glu Leu Ile Tyr Ser Ile Ala Gly Gly Asn Pro Tyr Gly Leu Phe Gln
            720             725             730

ATT GGG TCA CAT TCA GGT GCC ATC ACC CTG GAG AAG GAG ATT GAG CGG            2738
Ile Gly Ser His Ser Gly Ala Ile Thr Leu Glu Lys Glu Ile Glu Arg
        735             740             745

CGC CAC CAT GGG CTA CAC CGC CTG GTG GTG AAG GTC AGT GAC CGC GGC            2786
Arg His His Gly Leu His Arg Leu Val Val Lys Val Ser Asp Arg Gly
    750             755             760

AAG CCC CCA CGC TAT GGC ACA GCC TTG GTC CAT CTT TAT GTC AAT GAG            2834
Lys Pro Pro Arg Tyr Gly Thr Ala Leu Val His Leu Tyr Val Asn Glu
765             770             775             780

ACT CTG GCC AAC CGC ACG CTG CTG GAG ACC CTC CTG GGC CAC AGC CTG            2882
Thr Leu Ala Asn Arg Thr Leu Leu Glu Thr Leu Leu Gly His Ser Leu
                785             790             795

GAC ACG CCG CTG GAT ATT GAC ATT GCT GGG GAT CCA GAA TAT GAG CGC            2930
Asp Thr Pro Leu Asp Ile Asp Ile Ala Gly Asp Pro Glu Tyr Glu Arg
            800             805             810

TCC AAG CAG CGT GGC AAC ATT CTC TTT GGT GTG GTG GCT GGT GTG GTG            2978
Ser Lys Gln Arg Gly Asn Ile Leu Phe Gly Val Val Ala Gly Val Val
        815             820             825

GCC GTG GCC TTG CTC ATC GCC CTG GCG GTT CTT GTG CGC TAC TGC AGA            3026
Ala Val Ala Leu Leu Ile Ala Leu Ala Val Leu Val Arg Tyr Cys Arg
    830             835             840

CAG CGG GAG GCC AAA AGT GGT TAC CAG GCT GGT AAG AAG GAG ACC AAG            3074
Gln Arg Glu Ala Lys Ser Gly Tyr Gln Ala Gly Lys Lys Glu Thr Lys
845             850             855             860

GAC CTG TAT GCC CCC AAG CCC AGT GGC AAG GCC TCC AAG GGA AAC AAA            3122
Asp Leu Tyr Ala Pro Lys Pro Ser Gly Lys Ala Ser Lys Gly Asn Lys
                865             870             875

AGC AAA GGC AAG AAG AGC AAG TCC CCA AAG CCC GTG AAG CCA GTG GAG            3170
Ser Lys Gly Lys Lys Ser Lys Ser Pro Lys Pro Val Lys Pro Val Glu
            880             885             890

GAC GAG GAT GAG GCC GGG CTG CAG AAG TCC CTC AAG TTC AAC CTG ATG            3218
Asp Glu Asp Glu Ala Gly Leu Gln Lys Ser Leu Lys Phe Asn Leu Met
        895             900             905

AGC GAT GCC CCT GGG GAC AGT CCC CGC ATC CAC CTG CCC CTC AAC TAC            3266
```

| | | | | | | | | | | | | | | | |
|---|---|---|---|---|---|---|---|---|---|---|---|---|---|---|---|
| Ser | Asp | Ala | Pro | Gly | Asp | Ser | Pro | Arg | Ile | His | Leu | Pro | Leu | Asn | Tyr |
| | 910 | | | | 915 | | | | | 920 | | | | | |

| CCA | CCA | GGC | AGC | CCT | GAC | CTG | GGC | CGC | CAC | TAT | CGC | TCT | AAC | TCC | CCA | 3314 |
|---|---|---|---|---|---|---|---|---|---|---|---|---|---|---|---|---|
| Pro | Pro | Gly | Ser | Pro | Asp | Leu | Gly | Arg | His | Tyr | Arg | Ser | Asn | Ser | Pro | |
| 925 | | | | 930 | | | | | 935 | | | | | 940 | | |

| CTG | CCT | TCC | ATC | CAG | CTG | CAG | CCC | CAG | TCA | CCC | TCA | GCC | TCC | AAG | AAG | 3362 |
|---|---|---|---|---|---|---|---|---|---|---|---|---|---|---|---|---|
| Leu | Pro | Ser | Ile | Gln | Leu | Gln | Pro | Gln | Ser | Pro | Ser | Ala | Ser | Lys | Lys | |
| | | | 945 | | | | 950 | | | | | 955 | | | | |

| CAC | CAG | GTG | GTA | CAG | GAC | CTG | CCA | CCT | GCA | AAC | ACA | TTC | GTG | GGC | ACC | 3410 |
|---|---|---|---|---|---|---|---|---|---|---|---|---|---|---|---|---|
| His | Gln | Val | Val | Gln | Asp | Leu | Pro | Pro | Ala | Asn | Thr | Phe | Val | Gly | Thr | |
| | | | 960 | | | | | 965 | | | | | 970 | | | |

| GGG | GAC | ACC | ACG | TCC | ACG | GGC | TCT | GAG | CAG | TAC | TCC | GAC | TAC | AGC | TAC | 3458 |
|---|---|---|---|---|---|---|---|---|---|---|---|---|---|---|---|---|
| Gly | Asp | Thr | Thr | Ser | Thr | Gly | Ser | Glu | Gln | Tyr | Ser | Asp | Tyr | Ser | Tyr | |
| | | 975 | | | | | 980 | | | | | 985 | | | | |

| CGC | ACC | AAC | CCC | CCC | AAA | TAC | CCC | AGC | AAG | CAG | GTA | GGC | CAG | CCC | TTT | 3506 |
|---|---|---|---|---|---|---|---|---|---|---|---|---|---|---|---|---|
| Arg | Thr | Asn | Pro | Pro | Lys | Tyr | Pro | Ser | Lys | Gln | Val | Gly | Gln | Pro | Phe | |
| | 990 | | | | | 995 | | | | | 1000 | | | | | |

| CAG | CTC | AGC | ACA | CCC | CAG | CCC | CTA | CCC | CAC | CCC | TAC | CAC | GGA | GCC | ATC | 3554 |
|---|---|---|---|---|---|---|---|---|---|---|---|---|---|---|---|---|
| Gln | Leu | Ser | Thr | Pro | Gln | Pro | Leu | Pro | His | Pro | Tyr | His | Gly | Ala | Ile | |
| 1005 | | | | | 1010 | | | | 1015 | | | | | 1020 | | |

| TGG | ACC | GAG | GTG | TGG | GAG | TGATGGAGCA | GGTTTACTGT | GCCTGCCCGT | | 3602 |
|---|---|---|---|---|---|---|---|---|---|---|
| Trp | Thr | Glu | Val | Trp | Glu | | | | | |
| | | | | 1025 | | | | | | |

| | | | | |
|---|---|---|---|---|
| GTTGGGGGCC | AGCCTGAGCC | AGCAGTGGGA | GGTGGGGCCT | TAGTGCCTCA | CCGGGCACAC | 3662 |
| GGATTAGGCT | GAGTGAAGAT | TAAGGGAGGG | TGTGCTCTGT | GGTCTCCTCC | CTGCCCTCTC | 3722 |
| CCCACTGGGG | AGAGACCTGT | GATTTGCCAA | GTCCCTGGAC | CCTGGACCAG | CTACTGGGCC | 3782 |
| TTATGGGTTG | GGGGTGGTAG | GCAGGTGAGC | GTAAGTGGGG | AGGGAAATGG | GTAAGAAGTC | 3842 |
| TACTCCAAAC | CTAGGTCTCT | ATGTCAGACC | AGACCTAGGT | GCTTCTCTAG | GAGGGAAACA | 3902 |
| GGGAGACCTG | GGGTCCTGTG | GATAACTGAG | TGGGGAGTCT | GCCAGGGGAG | GGCACCTTCC | 3962 |
| CATTGTGCCT | TCTGTGTGTA | TTGTGCATTA | ACCTCTTCCT | CACCACTAGG | CTTCTGGGGC | 4022 |
| TGGGTCCCAC | ATGCCCTTGA | CCCTGACAAT | AAAGTTCTCT | ATTTTTGGAA | AAAAAAAAA | 4082 |
| AAAAAAAAAA | AAAAAAAAA | AA | | | | 4104 |

( 2 ) INFORMATION FOR SEQ ID NO:95:

( i ) SEQUENCE CHARACTERISTICS:
        ( A ) LENGTH: 1026 amino acids
        ( B ) TYPE: amino acid
        ( D ) TOPOLOGY: linear ( i i ) MOLECULE TYPE: protein ( x i ) SEQUENCE DESCRIPTION: SEQ ID NO:95:

| Met | Glu | Pro | Leu | Arg | His | Ser | Pro | Gly | Pro | Gly | Gly | Gln | Arg | Leu | Leu |
|---|---|---|---|---|---|---|---|---|---|---|---|---|---|---|---|
| 1 | | | | 5 | | | | | 10 | | | | | 15 | |

| Leu | Pro | Ser | Met | Leu | Leu | Ala | Leu | Leu | Leu | Leu | Ala | Pro | Ser | Pro | |
|---|---|---|---|---|---|---|---|---|---|---|---|---|---|---|---|
| | | | 20 | | | | | 25 | | | | | 30 | | |

| Gly | His | Ala | Thr | Arg | Val | Val | Tyr | Lys | Val | Pro | Glu | Glu | Gln | Pro | Pro |
|---|---|---|---|---|---|---|---|---|---|---|---|---|---|---|---|
| | | | 35 | | | | | 40 | | | | | 45 | | |

| Asn | Thr | Leu | Ile | Gly | Ser | Leu | Ala | Ala | Asp | Tyr | Gly | Phe | Pro | Asp | Val |
|---|---|---|---|---|---|---|---|---|---|---|---|---|---|---|---|
| | 50 | | | | | 55 | | | | | 60 | | | | |

| Gly | His | Leu | Tyr | Lys | Leu | Glu | Val | Gly | Ala | Pro | Tyr | Leu | Arg | Val | Asp |
|---|---|---|---|---|---|---|---|---|---|---|---|---|---|---|---|
| 65 | | | | | 70 | | | | | 75 | | | | | 80 |

| Gly | Lys | Thr | Gly | Asp | Ile | Phe | Thr | Thr | Glu | Thr | Ser | Ile | Asp | Arg | Glu |
|---|---|---|---|---|---|---|---|---|---|---|---|---|---|---|---|
| | | | | 85 | | | | | 90 | | | | | 95 | |

| Gly | Leu | Arg | Glu | Cys | Gln | Asn | Gln | Leu | Pro | Gly | Asp | Pro | Cys | Ile | Leu |
|---|---|---|---|---|---|---|---|---|---|---|---|---|---|---|---|

|   |   |   |   |   | 100 |   |   |   |   | 105 |   |   |   |   | 110 |   |   |
|---|---|---|---|---|---|---|---|---|---|---|---|---|---|---|---|---|---|
| Glu | Phe | Glu 115 | Val | Ser | Ile | Thr | Asp | Leu 120 | Val | Gln | Asn | Ala | Ser 125 | Pro | Arg |
| Leu | Leu 130 | Glu | Gly | Gln | Ile 135 | Glu | Val | Gln | Asp | Ile 140 | Asn | Asp | Asn | Thr | Pro |
| Asn 145 | Phe | Ala | Ser | Pro | Val 150 | Ile | Thr | Leu | Ala | Ile 155 | Pro | Glu | Asn | Thr | Asn 160 |
| Ile | Gly | Ser | Leu | Phe 165 | Pro | Ile | Pro | Leu | Ala 170 | Ser | Asp | Arg | Asp | Ala 175 | Gly |
| Pro | Asn | Gly | Val 180 | Ala | Ser | Tyr | Glu | Leu 185 | Gln | Val | Ala | Glu 190 | Asp | Gln | Glu |
| Glu | Lys | Gln 195 | Pro | Gln | Leu | Ile | Val 200 | Met | Gly | Asn | Leu | Asp 205 | Arg | Glu | Arg |
| Trp | Asp 210 | Ser | Tyr | Asp | Leu | Thr 215 | Ile | Lys | Val | Gln | Asp 220 | Gly | Gly | Ser | Pro |
| Pro 225 | Arg | Ala | Thr | Ser | Ala 230 | Leu | Leu | Arg | Val | Thr 235 | Val | Leu | Asp | Thr | Asn 240 |
| Asp | Asn | Ala | Pro | Lys 245 | Phe | Glu | Arg | Pro | Ser 250 | Tyr | Glu | Ala | Glu | Leu 255 | Ser |
| Glu | Asn | Ser | Pro 260 | Ile | Gly | His | Ser | Val 265 | Ile | Gln | Val | Lys | Ala 270 | Asn | Asp |
| Ser | Asp | Gln 275 | Gly | Ala | Asn | Ala | Glu 280 | Ile | Glu | Tyr | Thr | Phe 285 | His | Gln | Ala |
| Pro | Glu 290 | Val | Val | Arg | Arg | Leu 295 | Leu | Arg | Leu | Asp | Arg 300 | Asn | Thr | Gly | Leu |
| Ile 305 | Thr | Val | Gln | Gly | Pro 310 | Val | Asp | Arg | Glu | Asp 315 | Leu | Ser | Thr | Leu | Arg 320 |
| Phe | Ser | Val | Leu | Ala 325 | Lys | Asp | Arg | Gly | Thr 330 | Asn | Pro | Lys | Ser | Ala 335 | Arg |
| Ala | Gln | Val | Val 340 | Val | Thr | Val | Lys | Asp 345 | Met | Asn | Asp | Asn | Ala 350 | Pro | Thr |
| Ile | Glu | Ile 355 | Arg | Gly | Ile | Gly | Leu 360 | Val | Thr | His | Gln | Asp 365 | Gly | Met | Ala |
| Asn | Ile 370 | Ser | Glu | Asp | Val | Ala 375 | Glu | Glu | Thr | Ala | Val 380 | Ala | Leu | Val | Gln |
| Val 385 | Ser | Asp | Arg | Asp | Glu 390 | Gly | Glu | Asn | Ala | Ala 395 | Val | Thr | Cys | Val | Val 400 |
| Ala | Gly | Asp | Val | Pro 405 | Phe | Gln | Leu | Arg | Gln 410 | Ala | Ser | Glu | Thr | Gly 415 | Ser |
| Asp | Ser | Lys | Lys 420 | Lys | Tyr | Phe | Leu | Gln 425 | Thr | Thr | Thr | Pro | Leu 430 | Asp | Tyr |
| Glu | Lys | Val 435 | Lys | Asp | Tyr | Thr | Ile 440 | Glu | Ile | Val | Ala | Val 445 | Asp | Ser | Gly |
| Asn | Pro 450 | Pro | Leu | Ser | Ser | Thr 455 | Asn | Ser | Leu | Lys | Val 460 | Gln | Val | Val | Asp |
| Val 465 | Asn | Asp | Asn | Ala | Pro 470 | Val | Phe | Thr | Gln | Ser 475 | Val | Thr | Glu | Val | Ala 480 |
| Phe | Pro | Glu | Asn | Asn 485 | Lys | Pro | Gly | Glu | Val 490 | Ile | Ala | Glu | Ile | Thr 495 | Ala |
| Ser | Asp | Ala | Asp 500 | Ser | Gly | Ser | Asn | Ala 505 | Glu | Leu | Val | Tyr | Ser 510 | Leu | Glu |
| Pro | Glu | Pro 515 | Ala | Ala | Lys | Gly | Leu 520 | Phe | Thr | Ile | Ser | Pro 525 | Glu | Thr | Gly |

-continued

| | | | | | | | | | | | | | | |
|---|---|---|---|---|---|---|---|---|---|---|---|---|---|---|
| Glu | Ile | Gln | Val | Lys | Thr | Ser | Leu | Asp | Arg | Glu | Gln | Arg | Glu | Ser | Tyr |
| 530 | | | | | 535 | | | | | 540 | | | | | |
| Glu | Leu | Lys | Val | Val | Ala | Ala | Asp | Arg | Gly | Ser | Pro | Ser | Leu | Gln | Gly |
| 545 | | | | | 550 | | | | | 555 | | | | | 560 |
| Thr | Ala | Thr | Val | Leu | Val | Asn | Val | Leu | Asp | Cys | Asn | Asp | Asn | Asp | Pro |
| | | | | 565 | | | | | 570 | | | | | 575 | |
| Lys | Phe | Met | Leu | Ser | Gly | Tyr | Asn | Phe | Ser | Val | Met | Glu | Asn | Met | Pro |
| | | | 580 | | | | | 585 | | | | | 590 | | |
| Ala | Leu | Ser | Pro | Val | Gly | Met | Val | Thr | Val | Ile | Asp | Gly | Asp | Lys | Gly |
| | | 595 | | | | | 600 | | | | | 605 | | | |
| Glu | Asn | Ala | Gln | Val | Gln | Leu | Ser | Val | Glu | Gln | Asp | Asn | Gly | Asp | Phe |
| | | 610 | | | | | 615 | | | | | 620 | | | |
| Val | Ile | Gln | Asn | Gly | Thr | Gly | Thr | Ile | Leu | Ser | Ser | Leu | Ser | Phe | Asp |
| 625 | | | | | 630 | | | | | 635 | | | | | 640 |
| Arg | Glu | Gln | Gln | Ser | Thr | Tyr | Thr | Phe | Gln | Leu | Lys | Ala | Val | Asp | Gly |
| | | | | 645 | | | | | 650 | | | | | 655 | |
| Gly | Val | Pro | Pro | Arg | Ser | Ala | Tyr | Val | Gly | Val | Thr | Ile | Asn | Val | Leu |
| | | | 660 | | | | | 665 | | | | | 670 | | |
| Asp | Glu | Asn | Asp | Asn | Ala | Pro | Tyr | Ile | Thr | Ala | Pro | Ser | Asn | Thr | Ser |
| | | 675 | | | | | 680 | | | | | 685 | | | |
| His | Lys | Leu | Leu | Thr | Pro | Gln | Thr | Arg | Leu | Gly | Glu | Thr | Val | Ser | Gln |
| | 690 | | | | | 695 | | | | | 700 | | | | |
| Val | Ala | Ala | Glu | Asp | Phe | Asp | Ser | Gly | Val | Asn | Ala | Glu | Leu | Ile | Tyr |
| 705 | | | | | 710 | | | | | 715 | | | | | 720 |
| Ser | Ile | Ala | Gly | Gly | Asn | Pro | Tyr | Gly | Leu | Phe | Gln | Ile | Gly | Ser | His |
| | | | | 725 | | | | | 730 | | | | | 735 | |
| Ser | Gly | Ala | Ile | Thr | Leu | Glu | Lys | Glu | Ile | Glu | Arg | Arg | His | His | Gly |
| | | | 740 | | | | | 745 | | | | | 750 | | |
| Leu | His | Arg | Leu | Val | Val | Lys | Val | Ser | Asp | Arg | Gly | Lys | Pro | Pro | Arg |
| | | 755 | | | | | 760 | | | | | 765 | | | |
| Tyr | Gly | Thr | Ala | Leu | Val | His | Leu | Tyr | Val | Asn | Glu | Thr | Leu | Ala | Asn |
| | 770 | | | | | 775 | | | | | 780 | | | | |
| Arg | Thr | Leu | Leu | Glu | Thr | Leu | Leu | Gly | His | Ser | Leu | Asp | Thr | Pro | Leu |
| 785 | | | | | 790 | | | | | 795 | | | | | 800 |
| Asp | Ile | Asp | Ile | Ala | Gly | Asp | Pro | Glu | Tyr | Glu | Arg | Ser | Lys | Gln | Arg |
| | | | | 805 | | | | | 810 | | | | | 815 | |
| Gly | Asn | Ile | Leu | Phe | Gly | Val | Val | Ala | Gly | Val | Val | Ala | Val | Ala | Leu |
| | | | 820 | | | | | 825 | | | | | 830 | | |
| Leu | Ile | Ala | Leu | Ala | Val | Leu | Val | Arg | Tyr | Cys | Arg | Gln | Arg | Glu | Ala |
| | | 835 | | | | | 840 | | | | | 845 | | | |
| Lys | Ser | Gly | Tyr | Gln | Ala | Gly | Lys | Lys | Glu | Thr | Lys | Asp | Leu | Tyr | Ala |
| | 850 | | | | | 855 | | | | | 860 | | | | |
| Pro | Lys | Pro | Ser | Gly | Lys | Ala | Ser | Lys | Gly | Asn | Lys | Ser | Lys | Gly | Lys |
| 865 | | | | | 870 | | | | | 875 | | | | | 880 |
| Lys | Ser | Lys | Ser | Pro | Lys | Pro | Val | Lys | Pro | Val | Glu | Asp | Glu | Asp | Glu |
| | | | | 885 | | | | | 890 | | | | | 895 | |
| Ala | Gly | Leu | Gln | Lys | Ser | Leu | Lys | Phe | Asn | Leu | Met | Ser | Asp | Ala | Pro |
| | | | 900 | | | | | 905 | | | | | 910 | | |
| Gly | Asp | Ser | Pro | Arg | Ile | His | Leu | Pro | Leu | Asn | Tyr | Pro | Pro | Gly | Ser |
| | | 915 | | | | | 920 | | | | | 925 | | | |
| Pro | Asp | Leu | Gly | Arg | His | Tyr | Arg | Ser | Asn | Ser | Pro | Leu | Pro | Ser | Ile |
| | 930 | | | | | 935 | | | | | 940 | | | | |
| Gln | Leu | Gln | Pro | Gln | Ser | Pro | Ser | Ala | Ser | Lys | Lys | His | Gln | Val | Val |
| 945 | | | | | 950 | | | | | 955 | | | | | 960 |

| | | | | | | | | | | | | | | |
|---|---|---|---|---|---|---|---|---|---|---|---|---|---|---|
| Gln | Asp | Leu | Pro | Pro<br>965 | Ala | Asn | Thr | Phe | Val<br>970 | Gly | Thr | Gly | Asp<br>975 | Thr | Thr |
| Ser | Thr | Gly | Ser<br>980 | Glu | Gln | Tyr | Ser | Asp<br>985 | Tyr | Ser | Tyr | Arg | Thr<br>990 | Asn | Pro |
| Pro | Lys | Tyr<br>995 | Pro | Ser | Lys | Gln | Val<br>1000 | Gly | Gln | Pro | Phe | Gln<br>1005 | Leu | Ser | Thr |
| Pro | Gln | Pro<br>1010 | Leu | Pro | His | Pro<br>1015 | Tyr | His | Gly | Ala | Ile<br>1020 | Trp | Thr | Glu | Val |
| Trp | Glu<br>1025 | | | | | | | | | | | | | | |

( 2 ) INFORMATION FOR SEQ ID NO:96:

( i ) SEQUENCE CHARACTERISTICS:
        ( A ) LENGTH: 4705 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2827

( x i ) SEQUENCE DESCRIPTION: SEQ ID NO:96:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG         117
                                                              Met
                                                              1
```

| | | | | | | | | | | | | | | | |
|---|---|---|---|---|---|---|---|---|---|---|---|---|---|---|---|
| GTC | CCA | GAG | GCC | TGG | AGG | AGC | GGA | CTG | GTA | AGC | ACC | GGG | AGG | GTA | GTG | 165 |
| Val | Pro | Glu | Ala<br>5 | Trp | Arg | Ser | Gly | Leu<br>10 | Val | Ser | Thr | Gly | Arg<br>15 | Val | Val |
| GGA | GTT | TTG | CTT | CTG | CTT | GGT | GCC | TTG | AAC | AAG | GCT | TCC | ACG | GTC | ATT | 213 |
| Gly | Val | Leu<br>20 | Leu | Leu | Leu | Gly | Ala<br>25 | Leu | Asn | Lys | Ala | Ser<br>30 | Thr | Val | Ile |
| CAC | TAT | GAG | ATC | CCG | GAG | GAA | AGA | GAG | AAG | GGT | TTC | GCT | GTG | GGC | AAC | 261 |
| His | Tyr<br>35 | Glu | Ile | Pro | Glu | Glu<br>40 | Arg | Glu | Lys | Gly | Phe<br>45 | Ala | Val | Gly | Asn |
| GTG | GTC | GCG | AAC | CTT | GGT | TTG | GAT | CTC | GGT | AGC | CTC | TCA | GCC | CGC | AGG | 309 |
| Val<br>50 | Val | Ala | Asn | Leu | Gly<br>55 | Leu | Asp | Leu | Gly | Ser<br>60 | Leu | Ser | Ala | Arg | Arg<br>65 |
| TTC | CCG | GTG | GTG | TCT | GGA | GCT | AGC | CGA | AGA | TTC | TTT | GAG | GTG | AAC | CGG | 357 |
| Phe | Pro | Val | Val | Ser<br>70 | Gly | Ala | Ser | Arg | Arg<br>75 | Phe | Phe | Glu | Val | Asn<br>80 | Arg |
| GAG | ACC | GGA | GAG | ATG | TTT | GTG | AAC | GAC | CGT | CTG | GAT | CGA | GAG | GAG | CTG | 405 |
| Glu | Thr | Gly | Glu<br>85 | Met | Phe | Val | Asn | Asp<br>90 | Arg | Leu | Asp | Arg | Glu<br>95 | Glu | Leu |
| TGT | GGG | ACA | CTG | CCC | TCT | TGC | ACT | GTA | ACT | CTG | GAG | TTG | GTA | GTG | GAG | 453 |
| Cys | Gly | Thr<br>100 | Leu | Pro | Ser | Cys | Thr<br>105 | Val | Thr | Leu | Glu | Leu<br>110 | Val | Val | Glu |
| AAC | CCG | CTG | GAG | CTG | TTC | AGC | GTG | GAA | GTG | GTG | ATC | CAG | GAC | ATC | AAC | 501 |
| Asn | Pro | Leu<br>115 | Glu | Leu | Phe | Ser | Val<br>120 | Glu | Val | Val | Ile | Gln<br>125 | Asp | Ile | Asn |
| GAC | AAC | AAT | CCT | GCT | TTC | CCT | ACC | CAG | GAA | ATG | AAA | TTG | GAG | ATT | AGC | 549 |
| Asp<br>130 | Asn | Asn | Pro | Ala | Phe<br>135 | Pro | Thr | Gln | Glu | Met<br>140 | Lys | Leu | Glu | Ile | Ser<br>145 |
| GAG | GCC | GTG | GCT | CCG | GGG | ACG | CGC | TTT | CCG | CTC | GAG | AGC | GCG | CAC | GAT | 597 |
| Glu | Ala | Val | Ala | Pro<br>150 | Gly | Thr | Arg | Phe | Pro<br>155 | Leu | Glu | Ser | Ala | His<br>160 | Asp |
| CCC | GAT | CTG | GGA | AGC | AAC | TCT | TTA | CAA | ACC | TAT | GAG | CTG | AGC | CGA | AAT | 645 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Pro | Asp | Leu | Gly | Ser | Asn | Ser | Leu | Gln | Thr | Tyr | Glu | Leu | Ser | Arg | Asn |      |
|     |     |     | 165 |     |     |     |     | 170 |     |     |     |     | 175 |     |     |      |

```
GAA TAC TTT GCG CTT CGC GTG CAG ACG CGG GAG GAC AGC ACC AAG TAC     693
Glu Tyr Phe Ala Leu Arg Val Gln Thr Arg Glu Asp Ser Thr Lys Tyr
        180                     185                     190

GCG GAG CTG GTG TTG GAG CGC GCC CTG GAC CGA GAA CGG GAG CCT AGT     741
Ala Glu Leu Val Leu Glu Arg Ala Leu Asp Arg Glu Arg Glu Pro Ser
195                     200                     205

CTC CAG TTA GTG CTG ACG GCG TTG GAC GGA GGG ACC CCA GCT CTC TCC     789
Leu Gln Leu Val Leu Thr Ala Leu Asp Gly Gly Thr Pro Ala Leu Ser
210                     215                     220                     225

GCC AGC CTG CCT ATT CAC ATC AAG GTG CTG GAC GCG AAT GAC AAT GCG     837
Ala Ser Leu Pro Ile His Ile Lys Val Leu Asp Ala Asn Asp Asn Ala
                230                     235                     240

CCT GTC TTC AAC CAG TCC TTG TAC CGG GCG CGC GTT CCT GGA GGA TGC     885
Pro Val Phe Asn Gln Ser Leu Tyr Arg Ala Arg Val Pro Gly Gly Cys
            245                     250                     255

ACC TCC GGC ACG CGC GTG GTA CAA GTC CTT GCA ACG GAT CTG GAT GAA     933
Thr Ser Gly Thr Arg Val Val Gln Val Leu Ala Thr Asp Leu Asp Glu
        260                     265                     270

GGC CCC AAC GGT GAA ATT ATT TAC TCC TTC GGC AGC CAC AAC CGC GCC     981
Gly Pro Asn Gly Glu Ile Ile Tyr Ser Phe Gly Ser His Asn Arg Ala
275                     280                     285

GGC GTG CGG CAA CTA TTC GCC TTA GAC CTT GTA ACC GGG ATG CTG ACA    1029
Gly Val Arg Gln Leu Phe Ala Leu Asp Leu Val Thr Gly Met Leu Thr
290                     295                     300                     305

ATC AAG GGT CGG CTG GAC TTC GAG GAC ACC AAA CTC CAT GAG ATT TAC    1077
Ile Lys Gly Arg Leu Asp Phe Glu Asp Thr Lys Leu His Glu Ile Tyr
                310                     315                     320

ATC CAG GCC AAA GAC AAG GGC GCC AAT CCC GAA GGA GCA CAT TGC AAA    1125
Ile Gln Ala Lys Asp Lys Gly Ala Asn Pro Glu Gly Ala His Cys Lys
            325                     330                     335

GTG TTG GTG GAG GTT GTG GAT GTG AAT GAC AAC GCC CCG GAG ATC ACA    1173
Val Leu Val Glu Val Val Asp Val Asn Asp Asn Ala Pro Glu Ile Thr
        340                     345                     350

GTC ACC TCC GTG TAC AGC CCA GTA CCC GAG GAT GCC TCT GGG ACT GTC    1221
Val Thr Ser Val Tyr Ser Pro Val Pro Glu Asp Ala Ser Gly Thr Val
355                     360                     365

ATC GCT TTG CTC AGT GTG ACT GAC CTG GAT GCT GGC GAG AAC GGG CTG    1269
Ile Ala Leu Leu Ser Val Thr Asp Leu Asp Ala Gly Glu Asn Gly Leu
370                     375                     380                     385

GTG ACC TGC GAA GTT CCA CCG GGT CTC CCT TTC AGC CTT ACT TCT TCC    1317
Val Thr Cys Glu Val Pro Pro Gly Leu Pro Phe Ser Leu Thr Ser Ser
                390                     395                     400

CTC AAG AAT TAC TTC ACT TTG AAA ACC AGT GCA GAC CTG GAT CGG GAG    1365
Leu Lys Asn Tyr Phe Thr Leu Lys Thr Ser Ala Asp Leu Asp Arg Glu
            405                     410                     415

ACT GTG CCA GAA TAC AAC CTC AGC ATC ACC GCC CGA GAC GCC GGA ACC    1413
Thr Val Pro Glu Tyr Asn Leu Ser Ile Thr Ala Arg Asp Ala Gly Thr
        420                     425                     430

CCT TCC CTC TCA GCC CTT ACA ATA GTG CGT GTT CAA GTG TCC GAC ATC    1461
Pro Ser Leu Ser Ala Leu Thr Ile Val Arg Val Gln Val Ser Asp Ile
435                     440                     445

AAT GAC AAC CCT CCA CAA TCT TCT CAA TCT TCC TAC GAC GTT TAC ATT    1509
Asn Asp Asn Pro Pro Gln Ser Ser Gln Ser Ser Tyr Asp Val Tyr Ile
450                     455                     460                     465

GAA GAA AAC AAC CTC CCC GGG GCT CCA ATA CTA AAC CTA AGT GTC TGG    1557
Glu Glu Asn Asn Leu Pro Gly Ala Pro Ile Leu Asn Leu Ser Val Trp
                470                     475                     480

GAC CCC GAC GCC CCG CAG AAT GCT CGG CTT TCT TTC TTT CTC TTG GAG    1605
```

| | | | | | | | | | | | | | | | |
|---|---|---|---|---|---|---|---|---|---|---|---|---|---|---|---|
| Asp | Pro | Asp | Ala | Pro | Gln | Asn | Ala | Arg | Leu | Ser | Phe | Phe | Leu | Leu | Glu |
| | | | 485 | | | | 490 | | | | | | 495 | | |

| | | | | | | | | | | | | | | | | |
|---|---|---|---|---|---|---|---|---|---|---|---|---|---|---|---|---|
| CAA | GGA | GCT | GAA | ACC | GGG | CTA | GTG | GGT | CGC | TAT | TTC | ACA | ATA | AAT | CGT | 1653 |
| Gln | Gly | Ala | Glu | Thr | Gly | Leu | Val | Gly | Arg | Tyr | Phe | Thr | Ile | Asn | Arg | |
| | | 500 | | | | 505 | | | | | 510 | | | | | |
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg | |
| | 515 | | | | | 520 | | | | | 525 | | | | | |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val | |
| 530 | | | | | 535 | | | | | 540 | | | | | 545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp | |
| | | | | 550 | | | | | 555 | | | | | 560 | | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu | |
| | | | 565 | | | | | 570 | | | | | 575 | | | |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val | |
| | | 580 | | | | | 585 | | | | | 590 | | | | |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu | |
| | 595 | | | | | 600 | | | | | 605 | | | | | |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly | |
| 610 | | | | | 615 | | | | | 620 | | | | | 625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln | |
| | | | | 630 | | | | | 635 | | | | | 640 | | |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr | |
| | | | 645 | | | | | 650 | | | | | 655 | | | |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg | |
| | | 660 | | | | | 665 | | | | | 670 | | | | |
| GCC | GAG | TTC | CCC | TCT | GGC | TCT | GCC | CCC | CGG | GAG | CAG | AAA | AAA | AAT | CTC | 2181 |
| Ala | Glu | Phe | Pro | Ser | Gly | Ser | Ala | Pro | Arg | Glu | Gln | Lys | Lys | Asn | Leu | |
| 675 | | | | | 680 | | | | | 685 | | | | | | |
| ACC | TTT | TAT | CTA | CTT | CTT | TCT | CTA | ATC | CTG | GTT | TCT | GTG | GGC | TTC | GTG | 2229 |
| Thr | Phe | Tyr | Leu | Leu | Leu | Ser | Leu | Ile | Leu | Val | Ser | Val | Gly | Phe | Val | |
| 690 | | | | | 695 | | | | | 700 | | | | | 705 | |
| GTC | ACA | GTG | TTC | GGA | GTA | ATC | ATA | TTC | AAA | GTT | TAC | AAG | TGG | AAG | CAG | 2277 |
| Val | Thr | Val | Phe | Gly | Val | Ile | Ile | Phe | Lys | Val | Tyr | Lys | Trp | Lys | Gln | |
| | | | | 710 | | | | | 715 | | | | | 720 | | |
| TCT | AGA | GAC | CTA | TAC | CGA | GCC | CCG | GTG | AGC | TCA | CTG | TAC | CGA | ACA | CCA | 2325 |
| Ser | Arg | Asp | Leu | Tyr | Arg | Ala | Pro | Val | Ser | Ser | Leu | Tyr | Arg | Thr | Pro | |
| | | | 725 | | | | | 730 | | | | | 735 | | | |
| GGG | CCC | TCC | TTG | CAC | GCG | GAC | GCC | GTG | CGG | GGA | GGC | CTG | ATG | TCG | CCG | 2373 |
| Gly | Pro | Ser | Leu | His | Ala | Asp | Ala | Val | Arg | Gly | Gly | Leu | Met | Ser | Pro | |
| | | 740 | | | | | 745 | | | | | 750 | | | | |
| CAC | CTT | TAC | CAT | CAG | GTG | TAT | CTC | ACC | ACG | GAC | TCC | CGC | CGC | AGC | GAC | 2421 |
| His | Leu | Tyr | His | Gln | Val | Tyr | Leu | Thr | Thr | Asp | Ser | Arg | Arg | Ser | Asp | |
| | 755 | | | | | 760 | | | | | 765 | | | | | |
| CCG | CTG | CTG | AAG | AAA | CCT | GGT | GCA | GCC | AGT | CCA | CTG | GCC | AGC | CGC | CAG | 2469 |
| Pro | Leu | Leu | Lys | Lys | Pro | Gly | Ala | Ala | Ser | Pro | Leu | Ala | Ser | Arg | Gln | |
| 770 | | | | | 775 | | | | | 780 | | | | | 785 | |
| AAC | ACG | CTG | CGG | AGC | TGT | GAT | CCG | GTG | TTC | TAT | AGG | CAG | GTG | TTG | GGT | 2517 |
| Asn | Thr | Leu | Arg | Ser | Cys | Asp | Pro | Val | Phe | Tyr | Arg | Gln | Val | Leu | Gly | |
| | | | | 790 | | | | | 795 | | | | | 800 | | |
| GCA | GAG | AGC | GCC | CCT | CCC | GGA | CAG | CAA | GCC | CCG | CCC | AAC | ACG | GAC | TGG | 2565 |

-continued

|  |  |  |  |  |  |  |  |  |  |  |  |  |  |  |
|--|--|--|--|--|--|--|--|--|--|--|--|--|--|--|
| Ala | Glu | Ser | Ala 805 | Pro | Pro | Gly | Gln | Gln 810 | Ala | Pro | Pro | Asn | Thr 815 | Asp | Trp |

CGT TTC TCT CAG GCC CAG AGA CCC GGC ACC AGC GGC TCC CAA AAT GGC  2613
Arg Phe Ser Gln Ala Gln Arg Pro Gly Thr Ser Gly Ser Gln Asn Gly
        820                 825                     830

GAT GAC ACC GGC ACC TGG CCC AAC AAC CAG TTT GAC ACA GAG ATG CTG  2661
Asp Asp Thr Gly Thr Trp Pro Asn Asn Gln Phe Asp Thr Glu Met Leu
        835                 840                     845

CAA GCC ATG ATC TTG GCG TCC GCC AGT GAA GCT GCT GAT GGG AGC TCC  2709
Gln Ala Met Ile Leu Ala Ser Ala Ser Glu Ala Ala Asp Gly Ser Ser
850                 855                 860                 865

ACC CTG GGA GGG GGT GCC GGC ACC ATG GGA TTG AGC GCC CGC TAC GGA  2757
Thr Leu Gly Gly Gly Ala Gly Thr Met Gly Leu Ser Ala Arg Tyr Gly
                870                 875                 880

CCC CAG TTC ACC CTG CAG CAC GTG CCC GAC TAC CGC CAG AAT GTC TAC  2805
Pro Gln Phe Thr Leu Gln His Val Pro Asp Tyr Arg Gln Asn Val Tyr
            885                 890                 895

ATC CCA GGC AGC AAT GCA CAC T GACCAACGCA GCTGGCAAGC GGATGGCAAG    2857
Ile Pro Gly Ser Asn Ala His
            900

GCCCAGCAGG TGGCAATGGC AACAAGAAGA AGTCGGCAAG AAGGAGAAGA AGTAACATGG  2917
AGGCCAGGCC AAGAGCCACA GGGCAGCCTC TCCCCGAACC AGCCCAGCTT CTCCTTACCT  2977
GCACCCAGGC CTCAGAGTTT CAGGGCTAAC CCCCAGAATA CTGGTAGGGG CCAAGGCATC  3037
TCCCTTGGAA ACAGAAACAA GTGCCATCAC ACCATCCCTT CCCCAGGTGT AATATCCAAA  3097
GCAGTTCCGC TGGGAACCCC ATCCAATCAG TGGCTGTACC CATTTGGGTA GTGGGGTTCA  3157
TGTAGACACC AAGAACCATT TGCCACACCC CGTTTAGTTA CAGCTGAACC CTCCATCTTC  3217
CAAATCAATC AGGCCCATCC ATCCATGCC TCCCTCCTCC CCACCCCACT CCAACAGTTC   3277
CTCTTTCCCG AGTAAGGTGG TTGGGGTGTT GAAGTACCAA GTAACCTACA AGCCTCCTAG  3337
TTCTGAAAAG TTGGAAGGGC ATCATGACCT CTTGGCCTCT CCTTTGATTC TCAATCTTCC  3397
CCCAAAGCAT GGTTTGGTGC CAGCCCCTTC ACCTCCTTCC AGAGCCCAAG ATCAATGCTC  3457
AAGTTTTGGA GGACATGATC ACCATCCCCA TGGTACTGAT GCTTGCTGGA TTTAGGGAGG  3517
GCATTTTGCT ACCAAGCCTC TTCCCAACGC CCTGGGACCA GTCTTCTGTT TTGTTTTTCA  3577
TTGTTTGAGC TTTCCACTGC ATGCCTTGAC TTCCCCCACC TCCTCCTCAA ACAAGAGACT  3637
CCACTGCATG TTCCAAGACA GTATGGGGTG GTAAGATAAG GAAGGGAAGT GTGTGGATGT  3697
GGATGGTGGG GGCATGGACA AAGCTTGACA CATCAAGTTA TCAAGGCCTT GGAGGAGGCT  3757
CTGTATGTCC TCAGGGGACT GACAACATCC TCCAGATTCC AGCCATAAAC CAATAACTAG  3817
GCTGGACCCT TCCCACTACA TAATAGGGCT CAGCCAGGCA GCCAGCTTTG GGCTGAGCTA  3877
ACAGGACCAA TGGATTAACT GGCATTTCAG TCCAAGGAAG CTCGAAGCAG GTTTAGGACC  3937
AGGTCCCCTT GAGAGGTCAG AGGGGCCTCT GTGGGTGCTG GGTACTCCAG AGGTGCCACT  3997
GGTGGAAGGG TCAGCGGAGC CCCAGCAGGA AGGGTGGGCC AGCCAGGCCA TTCTTAGTCC  4057
CTGGGTTGGG GAGGCAGGGA GCTAGGGCAG GGACCAAATG AACAGAAAGT CTCAGCCCAG  4117
GATGGGGCTT CTTCAACAGG CCCCTGCCCT CCTGAAGCCT CAGTCCTTCA CCTTGCCAGG  4177
TGCCGTTTCT CTTCCGTGAA GGCCACTGCC CAGGTCCCCA GTGCGCCCCC TAGTGGCCAT  4237
AGCCTGGTTA AAGTTCCCCA GTGCCTCCTT GTGATAGACC TTCTTCTCCC ACCCCCTTCT  4297
GCCCCTGGGT CCCCGGCCAT CCAGCGGGGC TGCCAGAGAA CCCCAGACCT GCCCTTACAG  4357
TAGTGTAGCG CCCCCTCCCT CTTTCGGCTG GTGTAGAATA GCCAGTAGTG TAGTGCGGTG  4417
TGCTTTTACG TGATGGCGGG TGGGCAGCGG GCGGCGGCGT CCGCGCAGCC GTCTGTCCTT  4477

```
GATCTGCCCG CGGCGGCCCG TGTTGTGTTT TGTGCTGTGT CCAGCGCTAA GGCGACCCCC    4537

TCCCCCGTAC TGACTTCTCC TATAAGCGCT TCTCTTCGCA TAGTCACGTA GCTCCACCC     4597

CACCCTCTTC CTGTGTCTCA CGCAAGTTTT ATACTCTAAT ATTTATATGG CTTTTTTCT     4657

TCGACAAAAA AATAATAAAA CGTTTCTTCT GAAAAAAAAA AAAAAAA                  4705
```

( 2 ) INFORMATION FOR SEQ ID NO:97:

( i ) SEQUENCE CHARACTERISTICS:
        ( A ) LENGTH: 904 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
Met Val Pro Glu Ala Trp Arg Ser Gly Leu Val Ser Thr Gly Arg Val
  1               5                  10                  15

Val Gly Val Leu Leu Leu Gly Ala Leu Asn Lys Ala Ser Thr Val
                 20                  25                  30

Ile His Tyr Glu Ile Pro Glu Glu Arg Glu Lys Gly Phe Ala Val Gly
             35                  40                  45

Asn Val Val Ala Asn Leu Gly Leu Asp Leu Gly Ser Leu Ser Ala Arg
     50                  55                  60

Arg Phe Pro Val Val Ser Gly Ala Ser Arg Arg Phe Phe Glu Val Asn
 65                  70                  75                  80

Arg Glu Thr Gly Glu Met Phe Val Asn Asp Arg Leu Asp Arg Glu Glu
                 85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
            115                 120                 125

Asn Asp Asn Asn Pro Ala Phe Pro Thr Gln Glu Met Lys Leu Glu Ile
        130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
            180                 185                 190

Tyr Ala Glu Leu Val Leu Glu Arg Ala Leu Asp Arg Glu Arg Glu Pro
        195                 200                 205

Ser Leu Gln Leu Val Leu Thr Ala Leu Asp Gly Gly Thr Pro Ala Leu
210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
        275                 280                 285

Ala Gly Val Arg Gln Leu Phe Ala Leu Asp Leu Val Thr Gly Met Leu
    290                 295                 300

Thr Ile Lys Gly Arg Leu Asp Phe Glu Asp Thr Lys Leu His Glu Ile
305                 310                 315                 320
```

-continued

| | | | | | | | | | | | | | | | |
|---|---|---|---|---|---|---|---|---|---|---|---|---|---|---|---|
| Tyr | Ile | Gln | Ala | Lys<br>325 | Asp | Lys | Gly | Ala | Asn<br>330 | Pro | Glu | Gly | Ala | His<br>335 | Cys |
| Lys | Val | Leu | Val<br>340 | Glu | Val | Asp | Val<br>345 | Asn | Asp | Asn | Ala | Pro<br>350 | Glu | Ile | |
| Thr | Val | Thr<br>355 | Ser | Val | Tyr | Ser | Pro<br>360 | Val | Pro | Glu | Asp | Ala<br>365 | Ser | Gly | Thr |
| Val | Ile<br>370 | Ala | Leu | Leu | Ser | Val<br>375 | Thr | Asp | Leu | Asp | Ala<br>380 | Gly | Glu | Asn | Gly |
| Leu<br>385 | Val | Thr | Cys | Glu | Val<br>390 | Pro | Pro | Gly | Leu | Pro<br>395 | Phe | Ser | Leu | Thr | Ser<br>400 |
| Ser | Leu | Lys | Asn | Tyr<br>405 | Phe | Thr | Leu | Lys | Thr<br>410 | Ser | Ala | Asp | Leu | Asp<br>415 | Arg |
| Glu | Thr | Val | Pro<br>420 | Glu | Tyr | Asn | Leu | Ser<br>425 | Ile | Thr | Ala | Arg | Asp<br>430 | Ala | Gly |
| Thr | Pro | Ser<br>435 | Leu | Ser | Ala | Leu | Thr<br>440 | Ile | Val | Arg | Val | Gln<br>445 | Val | Ser | Asp |
| Ile | Asn<br>450 | Asp | Asn | Pro | Pro | Gln<br>455 | Ser | Ser | Gln | Ser | Ser<br>460 | Tyr | Asp | Val | Tyr |
| Ile<br>465 | Glu | Glu | Asn | Asn | Leu<br>470 | Pro | Gly | Ala | Pro | Ile<br>475 | Leu | Asn | Leu | Ser | Val<br>480 |
| Trp | Asp | Pro | Asp | Ala<br>485 | Pro | Gln | Asn | Ala | Arg<br>490 | Leu | Ser | Phe | Phe | Leu<br>495 | Leu |
| Glu | Gln | Gly | Ala<br>500 | Glu | Thr | Gly | Leu | Val<br>505 | Gly | Arg | Tyr | Phe | Thr<br>510 | Ile | Asn |
| Arg | Asp | Asn<br>515 | Gly | Ile | Val | Ser | Ser<br>520 | Leu | Val | Pro | Leu | Asp<br>525 | Tyr | Glu | Asp |
| Arg | Arg<br>530 | Glu | Phe | Glu | Leu | Thr<br>535 | Ala | His | Ile | Ser | Asp<br>540 | Gly | Gly | Thr | Pro |
| Val<br>545 | Leu | Ala | Thr | Asn | Ile<br>550 | Ser | Val | Asn | Ile | Phe<br>555 | Val | Thr | Asp | Arg | Asn<br>560 |
| Asp | Asn | Ala | Pro | Gln<br>565 | Val | Leu | Tyr | Pro | Arg<br>570 | Pro | Gly | Gly | Ser | Ser<br>575 | Val |
| Glu | Met | Leu | Pro<br>580 | Arg | Gly | Thr | Ser | Ala<br>585 | Gly | His | Leu | Val | Ser<br>590 | Arg | Val |
| Val | Gly | Trp<br>595 | Asp | Ala | Asp | Ala | Gly<br>600 | His | Asn | Ala | Trp | Leu<br>605 | Ser | Tyr | Ser |
| Leu | Phe<br>610 | Gly | Ser | Pro | Asn | Gln<br>615 | Ser | Leu | Phe | Ala | Ile<br>620 | Gly | Leu | His | Thr |
| Gly<br>625 | Gln | Ile | Ser | Thr | Ala<br>630 | Arg | Pro | Val | Gln | Asp<br>635 | Thr | Asp | Ser | Pro | Arg<br>640 |
| Gln | Thr | Leu | Thr | Val<br>645 | Leu | Ile | Lys | Asp | Asn<br>650 | Gly | Glu | Pro | Ser | Leu<br>655 | Ser |
| Thr | Thr | Ala | Thr<br>660 | Leu | Thr | Val | Ser | Val<br>665 | Thr | Glu | Asp | Ser | Pro<br>670 | Glu | Ala |
| Arg | Ala | Glu<br>675 | Phe | Pro | Ser | Gly | Ser<br>680 | Ala | Pro | Arg | Glu | Gln<br>685 | Lys | Lys | Asn |
| Leu | Thr<br>690 | Phe | Tyr | Leu | Leu | Leu<br>695 | Ser | Leu | Ile | Leu | Val<br>700 | Ser | Val | Gly | Phe |
| Val<br>705 | Val | Thr | Val | Phe | Gly<br>710 | Val | Ile | Ile | Phe | Lys<br>715 | Val | Tyr | Lys | Trp | Lys<br>720 |
| Gln | Ser | Arg | Asp | Leu<br>725 | Tyr | Arg | Ala | Pro | Val<br>730 | Ser | Ser | Leu | Tyr | Arg<br>735 | Thr |
| Pro | Gly | Pro | Ser | Leu | His | Ala | Asp | Ala | Val | Arg | Gly | Gly | Leu | Met | Ser |

```
                        740                    745                    750
Pro His Leu Tyr His Gln Val Tyr Leu Thr Thr Asp Ser Arg Arg Ser
        755                 760              765
Asp Pro Leu Leu Lys Lys Pro Gly Ala Ala Ser Pro Leu Ala Ser Arg
770                     775                 780
Gln Asn Thr Leu Arg Ser Cys Asp Pro Val Phe Tyr Arg Gln Val Leu
785                 790                 795                     800
Gly Ala Glu Ser Ala Pro Pro Gly Gln Gln Ala Pro Pro Asn Thr Asp
                805                 810                 815
Trp Arg Phe Ser Gln Ala Gln Arg Pro Gly Thr Ser Gly Ser Gln Asn
            820                 825                 830
Gly Asp Asp Thr Gly Thr Trp Pro Asn Asn Gln Phe Asp Thr Glu Met
        835                 840                 845
Leu Gln Ala Met Ile Leu Ala Ser Ala Ser Glu Ala Ala Asp Gly Ser
    850                 855                 860
Ser Thr Leu Gly Gly Gly Ala Gly Thr Met Gly Leu Ser Ala Arg Tyr
865                 870                 875                     880
Gly Pro Gln Phe Thr Leu Gln His Val Pro Asp Tyr Arg Gln Asn Val
            885                 890                 895
Tyr Ile Pro Gly Ser Asn Ala His
            900
```

( 2 ) INFORMATION FOR SEQ ID NO:98:

( i ) SEQUENCE CHARACTERISTICS:
        ( A ) LENGTH: 556 amino acids
        ( B ) TYPE: amino acid
        ( D ) TOPOLOGY: linear ( i i ) MOLECULE TYPE: protein ( x i ) SEQUENCE DESCRIPTION: SEQ ID NO:98:

```
Asp Trp Val Ile Pro Pro Ile Asn Leu Pro Glu Asn Ser Arg Gly Pro
1               5                   10                  15
Phe Pro Gln Glu Leu Val Arg Ile Arg Ser Asp Arg Asp Lys Asn Leu
                20                  25                  30
Ser Leu Arg Tyr Thr Val Thr Gly Pro Gly Ala Asp Gln Pro Pro Thr
            35                  40                  45
Gly Ile Phe Ile Ile Asn Pro Ile Ser Gly Gln Leu Ser Val Thr Lys
        50                  55                  60
Pro Leu Asp Arg Glu Gln Ile Ala Arg Phe His Leu Arg Ala His Ala
65                  70                  75                  80
Val Asp Ile Asn Gly Asn Gln Val Glu Asn Pro Ile Asp Ile Val Ile
                85                  90                  95
Asn Val Ile Asp Met Asn Asp Asn Arg Pro Glu Phe Leu His Gln Val
                100                 105                 110
Trp Asn Gly Ser Val Pro Glu Gly Ser Lys Pro Gly Thr Tyr Val Met
            115                 120                 125
Thr Val Thr Ala Ile Asp Ala Asp Asp Pro Asn Ala Leu Asn Gly Met
        130                 135                 140
Leu Arg Tyr Arg Ile Leu Ser Gln Ala Pro Ser Thr Pro Ser Pro Asn
145                 150                 155                 160
Met Phe Thr Ile Asn Asn Glu Thr Gly Asp Ile Ile Thr Val Ala Ala
                165                 170                 175
Gly Leu Asp Arg Glu Lys Val Gln Gln Tyr Thr Leu Ile Ile Gln Ala
                180                 185                 190
```

|     |     |     |     |     |     |     |     |     |     |     |     |     |     |     |
|-----|-----|-----|-----|-----|-----|-----|-----|-----|-----|-----|-----|-----|-----|-----|
| Thr | Asp | Met | Glu | Gly | Asn | Pro | Thr | Tyr | Gly | Leu | Ser | Asn | Thr | Ala | Thr |
|     |     | 195 |     |     |     | 200 |     |     |     |     | 205 |     |     |     |
| Ala | Val | Ile | Thr | Val | Thr | Asp | Val | Asn | Asp | Asn | Pro | Pro | Glu | Phe | Thr |
|     | 210 |     |     |     |     | 215 |     |     |     |     | 220 |     |     |     |
| Ala | Met | Thr | Phe | Tyr | Gly | Glu | Val | Pro | Glu | Asn | Arg | Val | Asp | Ile | Ile |
| 225 |     |     |     |     | 230 |     |     |     |     | 235 |     |     |     |     | 240 |
| Val | Ala | Asn | Leu | Thr | Val | Thr | Asp | Lys | Asp | Gln | Pro | His | Thr | Pro | Ala |
|     |     |     |     | 245 |     |     |     |     | 250 |     |     |     |     | 255 |     |
| Trp | Asn | Ala | Val | Thr | Arg | Ile | Ser | Gly | Gly | Asp | Pro | Thr | Gly | Arg | Phe |
|     |     |     | 260 |     |     |     |     | 265 |     |     |     |     | 270 |     |     |
| Ala | Ile | Gln | Thr | Asp | Pro | Asn | Ser | Asn | Asp | Gly | Leu | Val | Thr | Val | Val |
|     |     | 275 |     |     |     |     | 280 |     |     |     |     | 285 |     |     |     |
| Lys | Pro | Ile | Asp | Phe | Glu | Thr | Asn | Arg | Met | Phe | Val | Leu | Thr | Val | Ala |
|     | 290 |     |     |     |     | 295 |     |     |     |     | 300 |     |     |     |     |
| Ala | Glu | Asn | Gln | Val | Pro | Leu | Ala | Lys | Gly | Ile | Gln | His | Pro | Pro | Gln |
| 305 |     |     |     |     | 310 |     |     |     |     | 315 |     |     |     |     | 320 |
| Ser | Thr | Ala | Thr | Val | Ser | Val | Thr | Val | Ile | Asp | Val | Asn | Glu | Asn | Pro |
|     |     |     |     | 325 |     |     |     |     | 330 |     |     |     |     | 335 |     |
| Tyr | Phe | Ala | Pro | Asn | Pro | Lys | Ile | Ile | Arg | Gln | Glu | Glu | Gly | Leu | His |
|     |     |     | 340 |     |     |     |     | 345 |     |     |     |     | 350 |     |     |
| Ala | Gly | Thr | Met | Leu | Thr | Thr | Phe | Thr | Ala | Gly | Asp | Pro | Asp | Arg | Tyr |
|     |     | 355 |     |     |     |     | 360 |     |     |     |     | 365 |     |     |     |
| Met | Gln | Gln | Asn | Ile | Arg | Tyr | Thr | Lys | Leu | Ser | Asp | Pro | Ala | Asn | Trp |
|     | 370 |     |     |     |     | 375 |     |     |     |     | 380 |     |     |     |     |
| Leu | Lys | Ile | Asp | Pro | Val | Asn | Gly | Gln | Ile | Thr | Thr | Ile | Ala | Val | Leu |
| 385 |     |     |     |     | 390 |     |     |     |     | 395 |     |     |     |     | 400 |
| Asp | Arg | Glu | Ser | Pro | Asn | Val | Lys | Asn | Asn | Ile | Tyr | Asn | Ala | Thr | Phe |
|     |     |     |     | 405 |     |     |     |     | 410 |     |     |     |     | 415 |     |
| Leu | Ala | Ser | Asp | Asn | Gly | Ile | Pro | Pro | Met | Ser | Gly | Thr | Gly | Thr | Leu |
|     |     |     | 420 |     |     |     |     | 425 |     |     |     |     | 430 |     |     |
| Gln | Ile | Tyr | Leu | Leu | Asp | Ile | Asn | Asp | Asn | Ala | Pro | Gln | Val | Leu | Pro |
|     |     | 435 |     |     |     |     | 440 |     |     |     |     | 445 |     |     |     |
| Gln | Glu | Ala | Glu | Thr | Cys | Glu | Thr | Pro | Asp | Pro | Asn | Ser | Ile | Asn | Ile |
|     | 450 |     |     |     |     | 455 |     |     |     |     | 460 |     |     |     |     |
| Thr | Thr | Ala | Leu | Asp | Tyr | Asp | Ile | Asp | Pro | Asn | Ala | Gly | Pro | Phe | Ala |
| 465 |     |     |     |     | 470 |     |     |     |     | 475 |     |     |     |     | 480 |
| Tyr | Asp | Leu | Pro | Leu | Ser | Pro | Val | Thr | Ile | Lys | Arg | Asn | Trp | Thr | Ile |
|     |     |     |     | 485 |     |     |     |     | 490 |     |     |     |     | 495 |     |
| Thr | Arg | Leu | Asn | Gly | Asp | Phe | Ala | Gln | Leu | Asn | Leu | Lys | Ile | Lys | Phe |
|     |     |     | 500 |     |     |     |     | 505 |     |     |     |     | 510 |     |     |
| Leu | Glu | Ala | Gly | Ile | Tyr | Glu | Val | Pro | Ile | Ile | Ile | Thr | Asp | Ser | Gly |
|     |     | 515 |     |     |     |     | 520 |     |     |     |     | 525 |     |     |     |
| Asn | Pro | Pro | Lys | Ser | Asn | Lys | Ser | Ile | Leu | Arg | Val | Arg | Val | Cys | Gln |
|     | 530 |     |     |     |     | 535 |     |     |     |     | 540 |     |     |     |     |
| Cys | Asp | Phe | Asn | Gly | Asp | Cys | Thr | Asp | Val | Asp | Arg |     |     |     |     |
| 545 |     |     |     |     | 550 |     |     |     |     | 555 |     |     |     |     |     |

( 2 ) INFORMATION FOR SEQ ID NO:99:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:99:

| Glu | Asp | Thr | Val | Tyr | Ser | Phe | Asp | Ile | Pro | Glu | Asn | Ala | Gln | Arg | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Tyr | Gln | Val | Gly | Gln | Ile | Val | Ala | Arg | Asp | Ala | Asp | Leu | Gly | Gln | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Gln | Leu | Ser | Tyr | Gly | Val | Val | Ser | Asp | Trp | Ala | Asn | Asp | Val | Phe |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Leu | Asn | Pro | Gln | Thr | Gly | Met | Leu | Thr | Leu | Thr | Ala | Arg | Leu | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Tyr | Glu | Glu | Val | Gln | His | Tyr | Ile | Leu | Ile | Val | Gln | Ala | Gln | Asp | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Gln | Pro | Ser | Leu | Ser | Thr | Thr | Ile | Thr | Val | Tyr | Cys | Asn | Val | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asp | Leu | Asn | Asp | Asn | Ala | Pro | Ile | Phe |
|-----|-----|-----|-----|-----|-----|-----|-----|-----|
|     |     |     | 100 |     |     |     |     | 105 |

( 2 ) INFORMATION FOR SEQ ID NO:100:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:100:

| Asp | Xaa | Asp | Xaa | Gly | Xaa | Asn |
|-----|-----|-----|-----|-----|-----|-----|
| 1   |     |     |     | 5   |     |     |

( 2 ) INFORMATION FOR SEQ ID NO:101:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:101:

| Ala | Xaa | Asp | Xaa | Gly | Xaa | Pro |
|-----|-----|-----|-----|-----|-----|-----|
| 1   |     |     |     | 5   |     |     |

( 2 ) INFORMATION FOR SEQ ID NO:102:

( i ) SEQUENCE CHARACTERISTICS:
  ( A ) LENGTH: 4650 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 495..4103

( x i ) SEQUENCE DESCRIPTION: SEQ ID NO:102:

| CCTCTATTCG | ACATTCTCTT | TGGATTGTTT | TGCTATAACT | TGAAATTTGG | GATGTCACAA | 60  |
|------------|------------|------------|------------|------------|------------|-----|
| ACGAAACTGT | CATCTGTTTC | CGCCAAACTG | TGGTTCTGCT | AATCTCCCAG | GCTGGCAGCA | 120 |
| TTGGAGACTT | GCTGACTTCT | TTCATCCCCC | ACTCTTTTCA | CCTGAAATTC | CTTTCCTTGG | 180 |
| TTTTGCTCTA | AGTCCTATGC | TTCAGTCAGG | GGCCAACCAA | ATCTCACTGC | CTCCTTTTTA | 240 |

-continued

```
TCATGAAGCC TTTGATCACT GATAGTTCTT TTTATATCTT GAAAAATCAC CCTTCCCAGT        300

ACAGTTAATA TTTAGTATCT CTACTCATCT TGGCACTTAC TCACAGCTCC ATAATTCAGT        360

CGTTTTCGTA CCTCTTCATG GTGATGGGGA GCCCTTTGGA GGTGGTGACT GTGCTTTATA        420

CTCCTCATGA TGCTTACATA GTGGCAGGCG TGGAGTGCCC GGAGGCGGCC CTCCTGATTC        480

TGGGGCCTCC CAGG ATG GAG CCC CTG AGG CAC AGC CCA GGC CCT GGG GGG          530
              Met Glu Pro Leu Arg His Ser Pro Gly Pro Gly Gly
               1           5                      10

CAA CGG CTA CTG CTG CCC TCC ATG CTG CTA GCA CTG CTG CTC CTG CTG          578
Gln Arg Leu Leu Leu Pro Ser Met Leu Leu Ala Leu Leu Leu Leu Leu
         15              20              25

GCT CCA TCC CCA GGC CAC GCC ACT CGG GTA GTG TAC AAG GTG CCG GAG          626
Ala Pro Ser Pro Gly His Ala Thr Arg Val Val Tyr Lys Val Pro Glu
         30              35              40

GAA CAG CCA CCC AAC ACC CTC ATT GGG AGC CTC GCA GCC GAC TAT GGT          674
Glu Gln Pro Pro Asn Thr Leu Ile Gly Ser Leu Ala Ala Asp Tyr Gly
 45              50              55                          60

TTT CCA GAT GTG GGG CAC CTG TAC AAG CTA GAG GTG GGT GCC CCG TAC          722
Phe Pro Asp Val Gly His Leu Tyr Lys Leu Glu Val Gly Ala Pro Tyr
                 65              70                      75

CTT CGC GTG GAT GGC AAG ACA GGT GAC ATT TTC ACC ACC GAG ACC TCC          770
Leu Arg Val Asp Gly Lys Thr Gly Asp Ile Phe Thr Thr Glu Thr Ser
                 80              85                      90

ATC GAC CGT GAG GGG CTC CGT GAA TGC CAG AAC CAG CTC CCT GGT GAT          818
Ile Asp Arg Glu Gly Leu Arg Glu Cys Gln Asn Gln Leu Pro Gly Asp
         95             100             105

CCC TGC ATC CTG GAG TTT GAG GTA TCT ATC ACA GAC CTC GTG CAG AAT          866
Pro Cys Ile Leu Glu Phe Glu Val Ser Ile Thr Asp Leu Val Gln Asn
        110             115             120

GCG AGC CCC CGG CTG CTA GAG GGC CAG ATA GAA GTA CAA GAC ATC AAT          914
Ala Ser Pro Arg Leu Leu Glu Gly Gln Ile Glu Val Gln Asp Ile Asn
125             130             135                         140

GAC AAC ACA CCC AAC TTC GCC TCA CCA GTC ATC ACT CTG GCC ATC CCT          962
Asp Asn Thr Pro Asn Phe Ala Ser Pro Val Ile Thr Leu Ala Ile Pro
                145             150                         155

GAG AAC ACC AAC ATC GGC TCA CTC TTC CCC ATC CCG CTG GCT TCA GAC         1010
Glu Asn Thr Asn Ile Gly Ser Leu Phe Pro Ile Pro Leu Ala Ser Asp
        160             165                     170

CGT GAT GCT GGT CCC AAC GGT GTG GCA TCC TAT GAG CTG CAG GTG GCA         1058
Arg Asp Ala Gly Pro Asn Gly Val Ala Ser Tyr Glu Leu Gln Val Ala
        175             180                     185

GAG GAC CAG GAG GAG AAG CAA CCA CAG CTC ATT GTG ATG GGC AAC CTG         1106
Glu Asp Gln Glu Glu Lys Gln Pro Gln Leu Ile Val Met Gly Asn Leu
        190             195                     200

GAC CGT GAG CGC TGG GAC TCC TAT GAC CTC ACC ATC AAG GTG CAG GAT         1154
Asp Arg Glu Arg Trp Asp Ser Tyr Asp Leu Thr Ile Lys Val Gln Asp
205             210             215                         220

GGC GGC AGC CCC CCA CGC GCC ACG AGT GCC CTG CTG CGT GTC ACC GTG         1202
Gly Gly Ser Pro Pro Arg Ala Thr Ser Ala Leu Leu Arg Val Thr Val
                225             230                     235

CTT GAC ACC AAT GAC AAC GCC CCC AAG TTT GAG CGG CCC TCC TAT GAG         1250
Leu Asp Thr Asn Asp Asn Ala Pro Lys Phe Glu Arg Pro Ser Tyr Glu
                240             245                     250

GCC GAA CTA TCT GAG AAT AGC CCC ATA GGC CAC TCG GTC ATC CAG GTG         1298
Ala Glu Leu Ser Glu Asn Ser Pro Ile Gly His Ser Val Ile Gln Val
        255             260             265

AAG GCC AAT GAC TCA GAC CAA GGT GCC AAT GCA GAA ATC GAA TAC ACA         1346
Lys Ala Asn Asp Ser Asp Gln Gly Ala Asn Ala Glu Ile Glu Tyr Thr
270             275                         280
```

| | | | | | | | | | | | | | | | | |
|---|---|---|---|---|---|---|---|---|---|---|---|---|---|---|---|---|
| TTC | CAC | CAG | GCG | CCC | GAA | GTT | GTG | AGG | CGT | CTT | CTT | CGA | CTG | GAC | AGG | 1394 |
| Phe | His | Gln | Ala | Pro | Glu | Val | Val | Arg | Arg | Leu | Leu | Arg | Leu | Asp | Arg | |
| 285 | | | | 290 | | | | 295 | | | | | | | 300 | |
| AAC | ACT | GGA | CTT | ATC | ACT | GTT | CAG | GGC | CCG | GTG | GAC | CGT | GAG | GAC | CTA | 1442 |
| Asn | Thr | Gly | Leu | Ile | Thr | Val | Gln | Gly | Pro | Val | Asp | Arg | Glu | Asp | Leu | |
| | | | | 305 | | | | 310 | | | | | 315 | | | |
| AGC | ACC | CTG | CGC | TTC | TCA | GTG | CTT | GCT | AAG | GAC | CGA | GGC | ACC | AAC | CCC | 1490 |
| Ser | Thr | Leu | Arg | Phe | Ser | Val | Leu | Ala | Lys | Asp | Arg | Gly | Thr | Asn | Pro | |
| | | | 320 | | | | | 325 | | | | 330 | | | | |
| AAG | AGT | GCC | CGT | GCC | CAG | GTG | GTT | GTG | ACC | GTG | AAG | GAC | ATG | AAT | GAC | 1538 |
| Lys | Ser | Ala | Arg | Ala | Gln | Val | Val | Val | Thr | Val | Lys | Asp | Met | Asn | Asp | |
| | | 335 | | | | | 340 | | | | 345 | | | | | |
| AAT | GCC | CCC | ACC | ATT | GAG | ATC | CGG | GGC | ATA | GGG | CTA | GTG | ACT | CAT | CAA | 1586 |
| Asn | Ala | Pro | Thr | Ile | Glu | Ile | Arg | Gly | Ile | Gly | Leu | Val | Thr | His | Gln | |
| | 350 | | | | | 355 | | | | | 360 | | | | | |
| GAT | GGG | ATG | GCT | AAC | ATC | TCA | GAG | GAT | GTG | GCA | GAG | GAG | ACA | GCT | GTG | 1634 |
| Asp | Gly | Met | Ala | Asn | Ile | Ser | Glu | Asp | Val | Ala | Glu | Glu | Thr | Ala | Val | |
| 365 | | | | | 370 | | | | 375 | | | | | | 380 | |
| GCC | CTG | GTG | CAG | GTG | TCT | GAC | CGA | GAT | GAG | GGA | GAG | AAT | GCA | GCT | GTC | 1682 |
| Ala | Leu | Val | Gln | Val | Ser | Asp | Arg | Asp | Glu | Gly | Glu | Asn | Ala | Ala | Val | |
| | | | | 385 | | | | | 390 | | | | | 395 | | |
| ACC | TGT | GTG | GTG | GCA | GGT | GAT | GTG | CCC | TTC | CAG | CTG | CGC | CAG | GCC | AGT | 1730 |
| Thr | Cys | Val | Val | Ala | Gly | Asp | Val | Pro | Phe | Gln | Leu | Arg | Gln | Ala | Ser | |
| | | | 400 | | | | | 405 | | | | 410 | | | | |
| GAG | ACA | GGC | AGT | GAC | AGC | AAG | AAG | AAG | TAT | TTC | CTG | CAG | ACT | ACC | ACC | 1778 |
| Glu | Thr | Gly | Ser | Asp | Ser | Lys | Lys | Lys | Tyr | Phe | Leu | Gln | Thr | Thr | Thr | |
| | | 415 | | | | | 420 | | | | 425 | | | | | |
| CCG | CTA | GAC | TAC | GAG | AAG | GTC | AAA | GAC | TAC | ACC | ATT | GAG | ATT | GTG | GCT | 1826 |
| Pro | Leu | Asp | Tyr | Glu | Lys | Val | Lys | Asp | Tyr | Thr | Ile | Glu | Ile | Val | Ala | |
| | 430 | | | | | 435 | | | | 440 | | | | | | |
| GTG | GAC | TCT | GGC | AAC | CCC | CCA | CTC | TCC | AGC | ACT | AAC | TCC | CTC | AAG | GTG | 1874 |
| Val | Asp | Ser | Gly | Asn | Pro | Pro | Leu | Ser | Ser | Thr | Asn | Ser | Leu | Lys | Val | |
| 445 | | | | | 450 | | | | | 455 | | | | | 460 | |
| CAG | GTG | GTG | GAC | GTC | AAT | GAC | AAC | GCA | CCT | GTC | TTC | ACT | CAG | AGT | GTC | 1922 |
| Gln | Val | Val | Asp | Val | Asn | Asp | Asn | Ala | Pro | Val | Phe | Thr | Gln | Ser | Val | |
| | | | | 465 | | | | 470 | | | | | 475 | | | |
| ACT | GAG | GTC | GCC | TTC | CCG | GAA | AAC | AAC | AAG | CCT | GGT | GAA | GTG | ATT | GCT | 1970 |
| Thr | Glu | Val | Ala | Phe | Pro | Glu | Asn | Asn | Lys | Pro | Gly | Glu | Val | Ile | Ala | |
| | | | 480 | | | | | 485 | | | | 490 | | | | |
| GAG | ATC | ACT | GCC | AGT | GAT | GCT | GAC | TCT | GGC | TCT | AAT | GCT | GAG | CTG | GTT | 2018 |
| Glu | Ile | Thr | Ala | Ser | Asp | Ala | Asp | Ser | Gly | Ser | Asn | Ala | Glu | Leu | Val | |
| | | 495 | | | | | 500 | | | | | 505 | | | | |
| TAC | TCT | CTG | GAG | CCT | GAG | CCG | GCT | GCT | AAG | GGC | CTC | TTC | ACC | ATC | TCA | 2066 |
| Tyr | Ser | Leu | Glu | Pro | Glu | Pro | Ala | Ala | Lys | Gly | Leu | Phe | Thr | Ile | Ser | |
| | 510 | | | | | 515 | | | | | 520 | | | | | |
| CCC | GAG | ACT | GGA | GAG | ATC | CAG | GTG | AAG | ACA | TCT | CTG | GAT | CGG | GAA | CAG | 2114 |
| Pro | Glu | Thr | Gly | Glu | Ile | Gln | Val | Lys | Thr | Ser | Leu | Asp | Arg | Glu | Gln | |
| 525 | | | | | 530 | | | | | 535 | | | | | 540 | |
| CGG | GAG | AGC | TAT | GAG | TTG | AAG | GTG | GTG | GCA | GCT | GAC | CGG | GGC | AGT | CCT | 2162 |
| Arg | Glu | Ser | Tyr | Glu | Leu | Lys | Val | Val | Ala | Ala | Asp | Arg | Gly | Ser | Pro | |
| | | | | 545 | | | | | 550 | | | | | 555 | | |
| AGC | CTC | CAG | GGC | ACA | GCC | ACT | GTC | CTT | GTC | AAT | GTG | CTG | GAC | TGC | AAT | 2210 |
| Ser | Leu | Gln | Gly | Thr | Ala | Thr | Val | Leu | Val | Asn | Val | Leu | Asp | Cys | Asn | |
| | | | 560 | | | | | 565 | | | | | 570 | | | |
| GAC | AAT | GAC | CCC | AAA | TTT | ATG | CTG | AGT | GGC | TAC | AAC | TTC | TCA | GTG | ATG | 2258 |
| Asp | Asn | Asp | Pro | Lys | Phe | Met | Leu | Ser | Gly | Tyr | Asn | Phe | Ser | Val | Met | |
| | | 575 | | | | | 580 | | | | | 585 | | | | |
| GAG | AAC | ATG | CCA | GCA | CTG | AGT | CCA | GTG | GGC | ATG | GTG | ACT | GTC | ATT | GAT | 2306 |
| Glu | Asn | Met | Pro | Ala | Leu | Ser | Pro | Val | Gly | Met | Val | Thr | Val | Ile | Asp | |
| | 590 | | | | | 595 | | | | | 600 | | | | | |

```
GGA GAC AAG GGG GAG AAT GCC CAG GTG CAG CTC TCA GTG GAG CAG GAC    2354
Gly Asp Lys Gly Glu Asn Ala Gln Val Gln Leu Ser Val Glu Gln Asp
605             610                 615                 620

AAC GGT GAC TTT GTT ATC CAG AAT GGC ACA GGC ACC ATC CTA TCC AGC    2402
Asn Gly Asp Phe Val Ile Gln Asn Gly Thr Gly Thr Ile Leu Ser Ser
                625                 630                 635

CTG AGC TTT GAT CGA GAG CAA CAA AGC ACC TAC ACC TTC CAG CTG AAG    2450
Leu Ser Phe Asp Arg Glu Gln Gln Ser Thr Tyr Thr Phe Gln Leu Lys
            640                 645                 650

GCA GTG GAT GGT GGC GTC CCA CCT CGC TCA GCT TAC GTT GGT GTC ACC    2498
Ala Val Asp Gly Gly Val Pro Pro Arg Ser Ala Tyr Val Gly Val Thr
        655                 660                 665

ATC AAT GTG CTG GAC GAG AAT GAC AAC GCA CCC TAT ATC ACT GCC CCT    2546
Ile Asn Val Leu Asp Glu Asn Asp Asn Ala Pro Tyr Ile Thr Ala Pro
    670                 675                 680

TCT AAC ACC TCT CAC AAG CTG CTG ACC CCC CAG ACA CGT CTT GGT GAG    2594
Ser Asn Thr Ser His Lys Leu Leu Thr Pro Gln Thr Arg Leu Gly Glu
685                 690                 695                 700

ACG GTC AGC CAG GTG GCA GCC GAG GAC TTT GAC TCT GGT GTC AAT GCC    2642
Thr Val Ser Gln Val Ala Ala Glu Asp Phe Asp Ser Gly Val Asn Ala
                705                 710                 715

GAG CTG ATC TAC AGC ATT GCA GGT GGC AAC CCT TAT GGA CTC TTC CAG    2690
Glu Leu Ile Tyr Ser Ile Ala Gly Gly Asn Pro Tyr Gly Leu Phe Gln
            720                 725                 730

ATT GGG TCA CAT TCA GGT GCC ATC ACC CTG GAG AAG GAG ATT GAG CGG    2738
Ile Gly Ser His Ser Gly Ala Ile Thr Leu Glu Lys Glu Ile Glu Arg
        735                 740                 745

CGC CAC CAT GGG CTA CAC CGC CTG GTG GTG AAG GTC AGT GAC CGC GGC    2786
Arg His His Gly Leu His Arg Leu Val Val Lys Val Ser Asp Arg Gly
    750                 755                 760

AAG CCC CCA CGC TAT GGC ACA GCC TTG GTC CAT CTT TAT GTC AAT GAG    2834
Lys Pro Pro Arg Tyr Gly Thr Ala Leu Val His Leu Tyr Val Asn Glu
765                 770                 775                 780

ACT CTG GCC AAC CGC ACG CTG CTG GAG ACC CTC CTG GGC CAC AGC CTG    2882
Thr Leu Ala Asn Arg Thr Leu Leu Glu Thr Leu Leu Gly His Ser Leu
                785                 790                 795

GAC ACG CCG CTG GAT ATT GAC ATT GCT GGG GAT CCA GAA TAT GAG CGC    2930
Asp Thr Pro Leu Asp Ile Asp Ile Ala Gly Asp Pro Glu Tyr Glu Arg
            800                 805                 810

TCC AAG CAG CGT GGC AAC ATT CTC TTT GGT GTG GTG GCT GGT GTG GTG    2978
Ser Lys Gln Arg Gly Asn Ile Leu Phe Gly Val Val Ala Gly Val Val
        815                 820                 825

GCC GTG GCC TTG CTC ATC GCC CTG GCG GTT CTT GTG CGC TAC TGC AGA    3026
Ala Val Ala Leu Leu Ile Ala Leu Ala Val Leu Val Arg Tyr Cys Arg
    830                 835                 840

CAG CGG GAG GCC AAA AGT GGT TAC CAG GCT GGT AAG AAG GAG ACC AAG    3074
Gln Arg Glu Ala Lys Ser Gly Tyr Gln Ala Gly Lys Lys Glu Thr Lys
845                 850                 855                 860

GAC CTG TAT GCC CCC AAG CCC AGT GGC AAG GCC TCC AAG GGA AAC AAA    3122
Asp Leu Tyr Ala Pro Lys Pro Ser Gly Lys Ala Ser Lys Gly Asn Lys
                865                 870                 875

AGC AAA GGC AAG AAG AGC AAG TCC CCA AAG CCC GTG AAG CCA GTG GAG    3170
Ser Lys Gly Lys Lys Ser Lys Ser Pro Lys Pro Val Lys Pro Val Glu
            880                 885                 890

GAC GAG GAT GAG GCC GGG CTG CAG AAG TCC CTC AAG TTC AAC CTG ATG    3218
Asp Glu Asp Glu Ala Gly Leu Gln Lys Ser Leu Lys Phe Asn Leu Met
        895                 900                 905

AGC GAT GCC CCT GGG GAC AGT CCC CGC ATC CAC CTG CCC CTC AAC TAC    3266
Ser Asp Ala Pro Gly Asp Ser Pro Arg Ile His Leu Pro Leu Asn Tyr
910                 915                 920
```

| | | | | | | | | | | | | | | | | |
|---|---|---|---|---|---|---|---|---|---|---|---|---|---|---|---|---|
| CCA | CCA | GGC | AGC | CCT | GAC | CTG | GGC | CGC | CAC | TAT | CGC | TCT | AAC | TCC | CCA | 3314 |
| Pro | Pro | Gly | Ser | Pro | Asp | Leu | Gly | Arg | His | Tyr | Arg | Ser | Asn | Ser | Pro | |
| 925 | | | | 930 | | | | | 935 | | | | | | 940 | |
| CTG | CCT | TCC | ATC | CAG | CTG | CAG | CCC | CAG | TCA | CCC | TCA | GCC | TCC | AAG | AAG | 3362 |
| Leu | Pro | Ser | Ile | Gln | Leu | Gln | Pro | Gln | Ser | Pro | Ser | Ala | Ser | Lys | Lys | |
| | | | | 945 | | | | | 950 | | | | | 955 | | |
| CAC | CAG | GTG | GTA | CAG | GAC | CTG | CCA | CCT | GCA | AAC | ACA | TTC | GTG | GGC | ACC | 3410 |
| His | Gln | Val | Val | Gln | Asp | Leu | Pro | Pro | Ala | Asn | Thr | Phe | Val | Gly | Thr | |
| | | | 960 | | | | | 965 | | | | | 970 | | | |
| GGG | GAC | ACC | ACG | TCC | ACG | GGC | TCT | GAG | CAG | TAC | TCC | GAC | TAC | AGC | TAC | 3458 |
| Gly | Asp | Thr | Thr | Ser | Thr | Gly | Ser | Glu | Gln | Tyr | Ser | Asp | Tyr | Ser | Tyr | |
| | | 975 | | | | | 980 | | | | | 985 | | | | |
| CGC | ACC | AAC | CCC | CCC | AAA | TAC | CCC | AGC | AAG | CAG | TTA | CCT | CAC | CGC | CGC | 3506 |
| Arg | Thr | Asn | Pro | Pro | Lys | Tyr | Pro | Ser | Lys | Gln | Leu | Pro | His | Arg | Arg | |
| | 990 | | | | | 995 | | | | | 1000 | | | | | |
| GTC | ACC | TTC | TCG | GCC | ACC | AGC | CAG | GCC | CAG | GAG | CTG | CAG | GAC | CCA | TCC | 3554 |
| Val | Thr | Phe | Ser | Ala | Thr | Ser | Gln | Ala | Gln | Glu | Leu | Gln | Asp | Pro | Ser | |
| 1005 | | | | | 1010 | | | | | 1015 | | | | | 1020 | |
| CAG | CAC | AGT | TAC | TAT | GAC | AGT | GGC | CTG | GAG | GAG | TCT | GAG | ACG | CCG | TCC | 3602 |
| Gln | His | Ser | Tyr | Tyr | Asp | Ser | Gly | Leu | Glu | Glu | Ser | Glu | Thr | Pro | Ser | |
| | | | | 1025 | | | | | 1030 | | | | | 1035 | | |
| AGC | AAG | TCA | TCC | TCA | GGG | CCT | CGA | CTC | GGT | CCC | CTG | GCC | CTG | CCT | GAG | 3650 |
| Ser | Lys | Ser | Ser | Ser | Gly | Pro | Arg | Leu | Gly | Pro | Leu | Ala | Leu | Pro | Glu | |
| | | | 1040 | | | | | 1045 | | | | | 1050 | | | |
| GAT | CAC | TAT | GAG | CGC | ACC | ACC | CCT | GAT | GGC | AGC | ATA | GGA | GAG | ATG | GAG | 3698 |
| Asp | His | Tyr | Glu | Arg | Thr | Thr | Pro | Asp | Gly | Ser | Ile | Gly | Glu | Met | Glu | |
| | | | 1055 | | | | | 1060 | | | | | 1065 | | | |
| CAC | CCC | GAG | AAT | GAC | CTT | CGC | CCT | TTG | CCT | GAT | GTC | GCC | ATG | ACA | GGC | 3746 |
| His | Pro | Glu | Asn | Asp | Leu | Arg | Pro | Leu | Pro | Asp | Val | Ala | Met | Thr | Gly | |
| | 1070 | | | | | 1075 | | | | | 1080 | | | | | |
| ACA | TGT | ACC | CGG | GAG | TGC | AGT | GAG | TTT | GGC | CAC | TCT | GAC | ACA | TGC | TGG | 3794 |
| Thr | Cys | Thr | Arg | Glu | Cys | Ser | Glu | Phe | Gly | His | Ser | Asp | Thr | Cys | Trp | |
| 1085 | | | | 1090 | | | | | 1095 | | | | | 1100 | | |
| ATG | CCT | GGC | CAG | TCA | TCT | CCC | AGC | CGC | CGG | ACC | AAG | AGC | AGC | GCC | CTC | 3842 |
| Met | Pro | Gly | Gln | Ser | Ser | Pro | Ser | Arg | Arg | Thr | Lys | Ser | Ser | Ala | Leu | |
| | | | | 1105 | | | | | 1110 | | | | | 1115 | | |
| AAA | CTC | TCC | ACC | TTC | ATG | CCT | TAC | CAG | GAC | CGA | GGA | GGG | CAG | GAG | CCT | 3890 |
| Lys | Leu | Ser | Thr | Phe | Met | Pro | Tyr | Gln | Asp | Arg | Gly | Gly | Gln | Glu | Pro | |
| | | | 1120 | | | | | 1125 | | | | | 1130 | | | |
| GCG | GGC | GCC | GGC | AGC | CCC | AGC | CCC | CCG | GAA | GAC | CGG | AAC | ACC | AAA | ACG | 3938 |
| Ala | Gly | Ala | Gly | Ser | Pro | Ser | Pro | Pro | Glu | Asp | Arg | Asn | Thr | Lys | Thr | |
| | | | 1135 | | | | | 1140 | | | | | 1145 | | | |
| GCC | CCC | GTG | CGC | CTC | CTG | CCC | TCC | TAC | AGT | GCC | TTC | TCC | CAC | AGT | AGC | 3986 |
| Ala | Pro | Val | Arg | Leu | Leu | Pro | Ser | Tyr | Ser | Ala | Phe | Ser | His | Ser | Ser | |
| | 1150 | | | | | 1155 | | | | | 1160 | | | | | |
| CAT | GAT | TCC | TGC | AAG | GAC | TCG | GCC | ACC | TTG | GAG | GAA | ATC | CCC | CTG | ACC | 4034 |
| His | Asp | Ser | Cys | Lys | Asp | Ser | Ala | Thr | Leu | Glu | Glu | Ile | Pro | Leu | Thr | |
| 1165 | | | | 1170 | | | | | 1175 | | | | | 1180 | | |
| CAG | ACC | TCG | GAC | TTC | CCA | CCC | GCA | GCC | ACA | CCG | GCA | TCT | GCC | CAG | ACG | 4082 |
| Gln | Thr | Ser | Asp | Phe | Pro | Pro | Ala | Ala | Thr | Pro | Ala | Ser | Ala | Gln | Thr | |
| | | | | 1185 | | | | | 1190 | | | | | 1195 | | |
| GCC | AAG | CGC | GAG | ATC | TAC | CTG | TGAGCCCCT | ACTGGCCGGC | CCCCCTCCCC | | | | | | | 4133 |
| Ala | Lys | Arg | Glu | Ile | Tyr | Leu | | | | | | | | | | |
| | 1200 | | | | | | | | | | | | | | | |

| | | |
|---|---|---|
| CAGCGCCGGC CAGCTCCCAA ATGCCCATTC CAGGGCCTCA CTCTCCACCC CTTCAGCGTG | 4193 |
| GACTTCCTGC CAGGGCCCAA GTGGGGGTAT CACTGACCTC ATGACCACGC TGGCCCTTCT | 4253 |
| CCCATGCAGG GTCCAGGTCC TCTCCCCTCA TTTCCATCTC CCAGCCCAGG GGCCCCTTCC | 4313 |
| CCTTTATGGG GCTTCCCCCA GCTGATGCCC AAGAGGGCTC CTCTGCAATG ACTGGGCTCC | 4373 |

```
TTCCCTTGAC TTCCAGGGAG CACCCCCTCG ATTTGGGCAG ATGGTGGAGT CAAGGGTGGG    4433
CAGCGTACTT CTAACTCATT GTTTCCCTCA TGGCCGACCA GGGCGGGGAT AGCATGCCCA    4493
ATTTTAGCCC TGAAGCAGGG CTGAACTGGG GAGCCCCTTT CCCTGGGAGC TCCCAGAGGA    4553
AACTCTTGAC CACCAGTGGC TCCCTGAAGG GCTTTTGTTA CCAAAGGTGG GGTAGGGACG    4613
GGGGTGGGAG TGGAGCGGAG GCCTTGTTTT CCCGTGG                             4650
```

( 2 ) INFORMATION FOR SEQ ID NO:103:

( i ) SEQUENCE CHARACTERISTICS:
        ( A ) LENGTH: 1203 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

```
Met Glu Pro Leu Arg His Ser Pro Gly Pro Gly Gly Gln Arg Leu Leu
 1               5                  10                  15

Leu Pro Ser Met Leu Leu Ala Leu Leu Leu Leu Ala Pro Ser Pro
            20                  25                  30

Gly His Ala Thr Arg Val Val Tyr Lys Val Pro Glu Glu Gln Pro Pro
            35                  40                  45

Asn Thr Leu Ile Gly Ser Leu Ala Ala Asp Tyr Gly Phe Pro Asp Val
     50                  55                  60

Gly His Leu Tyr Lys Leu Glu Val Gly Ala Pro Tyr Leu Arg Val Asp
65                  70                  75                  80

Gly Lys Thr Gly Asp Ile Phe Thr Thr Glu Thr Ser Ile Asp Arg Glu
                85                  90                  95

Gly Leu Arg Glu Cys Gln Asn Gln Leu Pro Gly Asp Pro Cys Ile Leu
                100                 105                 110

Glu Phe Glu Val Ser Ile Thr Asp Leu Val Gln Asn Ala Ser Pro Arg
            115                 120                 125

Leu Leu Glu Gly Gln Ile Glu Val Gln Asp Ile Asn Asp Asn Thr Pro
    130                 135                 140

Asn Phe Ala Ser Pro Val Ile Thr Leu Ala Ile Pro Glu Asn Thr Asn
145                 150                 155                 160

Ile Gly Ser Leu Phe Pro Ile Pro Leu Ala Ser Asp Arg Asp Ala Gly
                165                 170                 175

Pro Asn Gly Val Ala Ser Tyr Glu Leu Gln Val Ala Glu Asp Gln Glu
                180                 185                 190

Glu Lys Gln Pro Gln Leu Ile Val Met Gly Asn Leu Asp Arg Glu Arg
            195                 200                 205

Trp Asp Ser Tyr Asp Leu Thr Ile Lys Val Gln Asp Gly Gly Ser Pro
    210                 215                 220

Pro Arg Ala Thr Ser Ala Leu Leu Arg Val Thr Val Leu Asp Thr Asn
225                 230                 235                 240

Asp Asn Ala Pro Lys Phe Glu Arg Pro Ser Tyr Glu Ala Glu Leu Ser
                245                 250                 255

Glu Asn Ser Pro Ile Gly His Ser Val Ile Gln Val Lys Ala Asn Asp
            260                 265                 270

Ser Asp Gln Gly Ala Asn Ala Glu Ile Glu Tyr Thr Phe His Gln Ala
        275                 280                 285

Pro Glu Val Val Arg Arg Leu Leu Arg Leu Asp Arg Asn Thr Gly Leu
    290                 295                 300

Ile Thr Val Gln Gly Pro Val Asp Arg Glu Asp Leu Ser Thr Leu Arg
```

```
305                    310                    315                    320

Phe Ser Val Leu Ala Lys Asp Arg Gly Thr Asn Pro Lys Ser Ala Arg
                325             330             335

Ala Gln Val Val Thr Val Lys Asp Met Asn Asp Asn Ala Pro Thr
            340             345             350

Ile Glu Ile Arg Gly Ile Gly Leu Val Thr His Gln Asp Gly Met Ala
        355             360             365

Asn Ile Ser Glu Asp Val Ala Glu Thr Ala Val Ala Leu Val Gln
    370             375             380

Val Ser Asp Arg Asp Glu Gly Glu Asn Ala Ala Val Thr Cys Val Val
385             390             395             400

Ala Gly Asp Val Pro Phe Gln Leu Arg Gln Ala Ser Glu Thr Gly Ser
                405             410             415

Asp Ser Lys Lys Lys Tyr Phe Leu Gln Thr Thr Thr Pro Leu Asp Tyr
            420             425             430

Glu Lys Val Lys Asp Tyr Thr Ile Glu Ile Val Ala Val Asp Ser Gly
        435             440             445

Asn Pro Pro Leu Ser Ser Thr Asn Ser Leu Lys Val Gln Val Val Asp
    450             455             460

Val Asn Asp Asn Ala Pro Val Phe Thr Gln Ser Val Thr Glu Val Ala
465             470             475             480

Phe Pro Glu Asn Asn Lys Pro Gly Glu Val Ile Ala Glu Ile Thr Ala
                485             490             495

Ser Asp Ala Asp Ser Gly Ser Asn Ala Glu Leu Val Tyr Ser Leu Glu
            500             505             510

Pro Glu Pro Ala Ala Lys Gly Leu Phe Thr Ile Ser Pro Glu Thr Gly
        515             520             525

Glu Ile Gln Val Lys Thr Ser Leu Asp Arg Glu Gln Arg Glu Ser Tyr
    530             535             540

Glu Leu Lys Val Val Ala Ala Asp Arg Gly Ser Pro Ser Leu Gln Gly
545             550             555             560

Thr Ala Thr Val Leu Val Asn Val Leu Asp Cys Asn Asp Asn Asp Pro
                565             570             575

Lys Phe Met Leu Ser Gly Tyr Asn Phe Ser Val Met Glu Asn Met Pro
            580             585             590

Ala Leu Ser Pro Val Gly Met Val Thr Val Ile Asp Gly Asp Lys Gly
        595             600             605

Glu Asn Ala Gln Val Gln Leu Ser Val Glu Gln Asp Asn Gly Asp Phe
    610             615             620

Val Ile Gln Asn Gly Thr Gly Thr Ile Leu Ser Ser Leu Ser Phe Asp
625             630             635             640

Arg Glu Gln Gln Ser Thr Tyr Thr Phe Gln Leu Lys Ala Val Asp Gly
                645             650             655

Gly Val Pro Pro Arg Ser Ala Tyr Val Gly Val Thr Ile Asn Val Leu
            660             665             670

Asp Glu Asn Asp Asn Ala Pro Tyr Ile Thr Ala Pro Ser Asn Thr Ser
        675             680             685

His Lys Leu Leu Thr Pro Gln Thr Arg Leu Gly Glu Thr Val Ser Gln
    690             695             700

Val Ala Ala Glu Asp Phe Asp Ser Gly Val Asn Ala Glu Leu Ile Tyr
705             710             715             720

Ser Ile Ala Gly Gly Asn Pro Tyr Gly Leu Phe Gln Ile Gly Ser His
                725             730             735
```

```
Ser Gly Ala Ile Thr Leu Glu Lys Glu Ile Glu Arg Arg His His Gly
            740                 745                 750

Leu His Arg Leu Val Val Lys Val Ser Asp Arg Gly Lys Pro Pro Arg
        755                 760                 765

Tyr Gly Thr Ala Leu Val His Leu Tyr Val Asn Glu Thr Leu Ala Asn
    770                 775                 780

Arg Thr Leu Leu Glu Thr Leu Leu Gly His Ser Leu Asp Thr Pro Leu
785                 790                 795                 800

Asp Ile Asp Ile Ala Gly Asp Pro Glu Tyr Glu Arg Ser Lys Gln Arg
            805                 810                 815

Gly Asn Ile Leu Phe Gly Val Val Ala Gly Val Val Ala Val Ala Leu
            820                 825                 830

Leu Ile Ala Leu Ala Val Leu Val Arg Tyr Cys Arg Gln Arg Glu Ala
        835                 840                 845

Lys Ser Gly Tyr Gln Ala Gly Lys Lys Glu Thr Lys Asp Leu Tyr Ala
    850                 855                 860

Pro Lys Pro Ser Gly Lys Ala Ser Lys Gly Asn Lys Ser Lys Gly Lys
865                 870                 875                 880

Lys Ser Lys Ser Pro Lys Pro Val Lys Pro Val Glu Asp Glu Asp Glu
            885                 890                 895

Ala Gly Leu Gln Lys Ser Leu Lys Phe Asn Leu Met Ser Asp Ala Pro
            900                 905                 910

Gly Asp Ser Pro Arg Ile His Leu Pro Leu Asn Tyr Pro Pro Gly Ser
        915                 920                 925

Pro Asp Leu Gly Arg His Tyr Arg Ser Asn Ser Pro Leu Pro Ser Ile
    930                 935                 940

Gln Leu Gln Pro Gln Ser Pro Ser Ala Ser Lys Lys His Gln Val Val
945                 950                 955                 960

Gln Asp Leu Pro Pro Ala Asn Thr Phe Val Gly Thr Gly Asp Thr Thr
            965                 970                 975

Ser Thr Gly Ser Glu Gln Tyr Ser Asp Tyr Ser Tyr Arg Thr Asn Pro
            980                 985                 990

Pro Lys Tyr Pro Ser Lys Gln Leu Pro His Arg Arg Val Thr Phe Ser
        995                 1000                1005

Ala Thr Ser Gln Ala Gln Glu Leu Gln Asp Pro Ser Gln His Ser Tyr
    1010                1015                1020

Tyr Asp Ser Gly Leu Glu Glu Ser Glu Thr Pro Ser Ser Lys Ser Ser
1025                1030                1035                1040

Ser Gly Pro Arg Leu Gly Pro Leu Ala Leu Pro Glu Asp His Tyr Glu
            1045                1050                1055

Arg Thr Thr Pro Asp Gly Ser Ile Gly Glu Met Glu His Pro Glu Asn
            1060                1065                1070

Asp Leu Arg Pro Leu Pro Asp Val Ala Met Thr Gly Thr Cys Thr Arg
        1075                1080                1085

Glu Cys Ser Glu Phe Gly His Ser Asp Thr Cys Trp Met Pro Gly Gln
    1090                1095                1100

Ser Ser Pro Ser Arg Arg Thr Lys Ser Ser Ala Leu Lys Leu Ser Thr
1105                1110                1115                1120

Phe Met Pro Tyr Gln Asp Arg Gly Gly Gln Glu Pro Ala Gly Ala Gly
            1125                1130                1135

Ser Pro Ser Pro Pro Glu Asp Arg Asn Thr Lys Thr Ala Pro Val Arg
            1140                1145                1150

Leu Leu Pro Ser Tyr Ser Ala Phe Ser His Ser Ser His Asp Ser Cys
        1155                1160                1165
```

5,663,300

111                                                                                              112

-continued

Lys Asp Ser Ala Thr Leu Glu Glu Ile Pro Leu Thr Gln Thr Ser Asp
    1170                1175                1180

Phe Pro Pro Ala Ala Thr Pro Ala Ser Ala Gln Thr Ala Lys Arg Glu
1185                1190                1195                1200

Ile Tyr Leu ( 2 ) INFORMATION FOR SEQ ID NO:104:

( i ) SEQUENCE CHARACTERISTICS:
        ( A ) LENGTH: 2789 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2622

( x i ) SEQUENCE DESCRIPTION: SEQ ID NO:104:

CGAAAGCCAT GTCGGACTCG TCGCCCAGCG CCCAAGCGCT AACCCGCTGA AAGTTTCTCA                60

GCGAAATCTC AGGGACGATC TGGACCCCGC TGAGAGGAAC TGCTTTTGAG TGAG ATG                 117
                                                                Met
                                                                 1

GTC CCA GAG GCC TGG AGG AGC GGA CTG GTA AGC ACC GGG AGG GTA GTG                 165
Val Pro Glu Ala Trp Arg Ser Gly Leu Val Ser Thr Gly Arg Val Val
            5                   10                  15

GGA GTT TTG CTT CTG CTT GGT GCC TTG AAC AAG GCT TCC ACG GTC ATT                 213
Gly Val Leu Leu Leu Leu Gly Ala Leu Asn Lys Ala Ser Thr Val Ile
        20                  25                  30

CAC TAT GAG ATC CCG GAG GAA AGA GAG AAG GGT TTC GCT GTG GGC AAC                 261
His Tyr Glu Ile Pro Glu Glu Arg Glu Lys Gly Phe Ala Val Gly Asn
    35                  40                  45

GTG GTC GCG AAC CTT GGT TTG GAT CTC GGT AGC CTC TCA GCC CGC AGG                 309
Val Val Ala Asn Leu Gly Leu Asp Leu Gly Ser Leu Ser Ala Arg Arg
50                  55                  60                  65

TTC CCG GTG GTG TCT GGA GCT AGC CGA AGA TTC TTT GAG GTG AAC CGG                 357
Phe Pro Val Val Ser Gly Ala Ser Arg Arg Phe Phe Glu Val Asn Arg
            70                  75                  80

GAG ACC GGA GAG ATG TTT GTG AAC GAC CGT CTG GAT CGA GAG GAG CTG                 405
Glu Thr Gly Glu Met Phe Val Asn Asp Arg Leu Asp Arg Glu Glu Leu
        85                  90                  95

TGT GGG ACA CTG CCC TCT TGC ACT GTA ACT CTG GAG TTG GTA GTG GAG                 453
Cys Gly Thr Leu Pro Ser Cys Thr Val Thr Leu Glu Leu Val Val Glu
    100                 105                 110

AAC CCG CTG GAG CTG TTC AGC GTG GAA GTG GTG ATC CAG GAC ATC AAC                 501
Asn Pro Leu Glu Leu Phe Ser Val Glu Val Val Ile Gln Asp Ile Asn
115                 120                 125

GAC AAC AAT CCT GCT TTC CCT ACC CAG GAA ATG AAA TTG GAG ATT AGC                 549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT                 597
Glu Ala Val Ala Pro Gly Thr Arg Phe Pro Leu Glu Ser Ala His Asp
        150                 155                 160

CCC GAT CTG GGA AGC AAC TCT TTA CAA ACC TAT GAG CTG AGC CGA AAT                 645
Pro Asp Leu Gly Ser Asn Ser Leu Gln Thr Tyr Glu Leu Ser Arg Asn
    165                 170                 175

GAA TAC TTT GCG CTT CGC GTG CAG ACG CGG GAG GAC AGC ACC AAG TAC                 693
Glu Tyr Phe Ala Leu Arg Val Gln Thr Arg Glu Asp Ser Thr Lys Tyr
            180                 185                 190

```
GCG GAG CTG GTG TTG GAG CGC GCC CTG GAC CGA GAA CGG GAG CCT AGT     741
Ala Glu Leu Val Leu Glu Arg Ala Leu Asp Arg Glu Arg Glu Pro Ser
    195                 200                 205

CTC CAG TTA GTG CTG ACG GCG TTG GAC GGA GGG ACC CCA GCT CTC TCC     789
Leu Gln Leu Val Leu Thr Ala Leu Asp Gly Gly Thr Pro Ala Leu Ser
210                 215                 220                 225

GCC AGC CTG CCT ATT CAC ATC AAG GTG CTG GAC GCG AAT GAC AAT GCG     837
Ala Ser Leu Pro Ile His Ile Lys Val Leu Asp Ala Asn Asp Asn Ala
                    230                 235                 240

CCT GTC TTC AAC CAG TCC TTG TAC CGG GCG CGC GTT CCT GGA GGA TGC     885
Pro Val Phe Asn Gln Ser Leu Tyr Arg Ala Arg Val Pro Gly Gly Cys
                245                 250                 255

ACC TCC GGC ACG CGC GTG GTA CAA GTC CTT GCA ACG GAT CTG GAT GAA     933
Thr Ser Gly Thr Arg Val Val Gln Val Leu Ala Thr Asp Leu Asp Glu
            260                 265                 270

GGC CCC AAC GGT GAA ATT ATT TAC TCC TTC GGC AGC CAC AAC CGC GCC     981
Gly Pro Asn Gly Glu Ile Ile Tyr Ser Phe Gly Ser His Asn Arg Ala
        275                 280                 285

GGC GTG CGG CAA CTA TTC GCC TTA GAC CTT GTA ACC GGG ATG CTG ACA    1029
Gly Val Arg Gln Leu Phe Ala Leu Asp Leu Val Thr Gly Met Leu Thr
290                 295                 300                 305

ATC AAG GGT CGG CTG GAC TTC GAG GAC ACC AAA CTC CAT GAG ATT TAC    1077
Ile Lys Gly Arg Leu Asp Phe Glu Asp Thr Lys Leu His Glu Ile Tyr
                310                 315                 320

ATC CAG GCC AAA GAC AAG GGC GCC AAT CCC GAA GGA GCA CAT TGC AAA    1125
Ile Gln Ala Lys Asp Lys Gly Ala Asn Pro Glu Gly Ala His Cys Lys
                325                 330                 335

GTG TTG GTG GAG GTT GTG GAT GTG AAT GAC AAC GCC CCG GAG ATC ACA    1173
Val Leu Val Glu Val Val Asp Val Asn Asp Asn Ala Pro Glu Ile Thr
            340                 345                 350

GTC ACC TCC GTG TAC AGC CCA GTA CCC GAG GAT GCC TCT GGG ACT GTC    1221
Val Thr Ser Val Tyr Ser Pro Val Pro Glu Asp Ala Ser Gly Thr Val
        355                 360                 365

ATC GCT TTG CTC AGT GTG ACT GAC CTG GAT GCT GGC GAG AAC GGG CTG    1269
Ile Ala Leu Leu Ser Val Thr Asp Leu Asp Ala Gly Glu Asn Gly Leu
370                 375                 380                 385

GTG ACC TGC GAA GTT CCA CCG GGT CTC CCT TTC AGC CTT ACT TCT TCC    1317
Val Thr Cys Glu Val Pro Pro Gly Leu Pro Phe Ser Leu Thr Ser Ser
                390                 395                 400

CTC AAG AAT TAC TTC ACT TTG AAA ACC AGT GCA GAC CTG GAT CGG GAG    1365
Leu Lys Asn Tyr Phe Thr Leu Lys Thr Ser Ala Asp Leu Asp Arg Glu
                405                 410                 415

ACT GTG CCA GAA TAC AAC CTC AGC ATC ACC GCC CGA GAC GCC GGA ACC    1413
Thr Val Pro Glu Tyr Asn Leu Ser Ile Thr Ala Arg Asp Ala Gly Thr
            420                 425                 430

CCT TCC CTC TCA GCC CTT ACA ATA GTG CGT GTT CAA GTG TCC GAC ATC    1461
Pro Ser Leu Ser Ala Leu Thr Ile Val Arg Val Gln Val Ser Asp Ile
        435                 440                 445

AAT GAC AAC CCT CCA CAA TCT TCT CAA TCT TCC TAC GAC GTT TAC ATT    1509
Asn Asp Asn Pro Pro Gln Ser Ser Gln Ser Ser Tyr Asp Val Tyr Ile
450                 455                 460                 465

GAA GAA AAC AAC CTC CCC GGG GCT CCA ATA CTA AAC CTA AGT GTC TGG    1557
Glu Glu Asn Asn Leu Pro Gly Ala Pro Ile Leu Asn Leu Ser Val Trp
                470                 475                 480

GAC CCC GAC GCC CCG CAG AAT GCT CGG CTT TCT TTC TTT CTC TTG GAG    1605
Asp Pro Asp Ala Pro Gln Asn Ala Arg Leu Ser Phe Phe Leu Leu Glu
                485                 490                 495

CAA GGA GCT GAA ACC GGG CTA GTG GGT CGC TAT TTC ACA ATA AAT CGT    1653
Gln Gly Ala Glu Thr Gly Leu Val Gly Arg Tyr Phe Thr Ile Asn Arg
            500                 505                 510
```

-continued

| | | | | | | | | | | | | | | | | |
|---|---|---|---|---|---|---|---|---|---|---|---|---|---|---|---|---|
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg | |
| 515 | | | | | 520 | | | | | 525 | | | | | | |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val | |
| 530 | | | | | 535 | | | | | 540 | | | | | 545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp | |
| | | | | 550 | | | | | 555 | | | | | 560 | | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu | |
| | | | 565 | | | | | 570 | | | | | 575 | | | |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val | |
| | | | 580 | | | | | 585 | | | | | 590 | | | |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu | |
| | 595 | | | | | 600 | | | | | 605 | | | | | |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly | |
| 610 | | | | | 615 | | | | | 620 | | | | | 625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln | |
| | | | | 630 | | | | | 635 | | | | | 640 | | |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr | |
| | | | 645 | | | | | 650 | | | | | 655 | | | |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg | |
| | | 660 | | | | | 665 | | | | | 670 | | | | |
| GCC | GAG | TTC | CCC | TCT | GGC | TCT | GCC | CCC | CGG | GAG | CAG | AAA | AAA | AAT | CTC | 2181 |
| Ala | Glu | Phe | Pro | Ser | Gly | Ser | Ala | Pro | Arg | Glu | Gln | Lys | Lys | Asn | Leu | |
| | 675 | | | | | 680 | | | | | 685 | | | | | |
| ACC | TTT | TAT | CTA | CTT | CTT | TCT | CTA | ATC | CTG | GTT | TCT | GTG | GGC | TTC | GTG | 2229 |
| Thr | Phe | Tyr | Leu | Leu | Leu | Ser | Leu | Ile | Leu | Val | Ser | Val | Gly | Phe | Val | |
| 690 | | | | | 695 | | | | | 700 | | | | | 705 | |
| GTC | ACA | GTG | TTC | GGA | GTA | ATC | ATA | TTC | AAA | GTT | TAC | AAG | TGG | AAG | CAG | 2277 |
| Val | Thr | Val | Phe | Gly | Val | Ile | Ile | Phe | Lys | Val | Tyr | Lys | Trp | Lys | Gln | |
| | | | | 710 | | | | | 715 | | | | | 720 | | |
| TCT | AGA | GAC | CTA | TAC | CGA | GCC | CCG | GTG | AGC | TCA | CTG | TAC | CGA | ACA | CCA | 2325 |
| Ser | Arg | Asp | Leu | Tyr | Arg | Ala | Pro | Val | Ser | Ser | Leu | Tyr | Arg | Thr | Pro | |
| | | | 725 | | | | | 730 | | | | | 735 | | | |
| GGG | CCC | TCC | TTG | CAC | GCG | GAC | GCC | GTG | CGG | GGA | GGC | CTG | ATG | TCG | CCG | 2373 |
| Gly | Pro | Ser | Leu | His | Ala | Asp | Ala | Val | Arg | Gly | Gly | Leu | Met | Ser | Pro | |
| | | 740 | | | | | 745 | | | | | 750 | | | | |
| CAC | CTT | TAC | CAT | CAG | GTG | TAT | CTC | ACC | ACG | GAC | TCC | CGC | CGC | AGC | GAC | 2421 |
| His | Leu | Tyr | His | Gln | Val | Tyr | Leu | Thr | Thr | Asp | Ser | Arg | Arg | Ser | Asp | |
| | 755 | | | | | 760 | | | | | 765 | | | | | |
| CCG | CTG | CTG | AAG | AAA | CCT | GGT | GCA | GCC | AGT | CCA | CTG | GCC | AGC | CGC | CAG | 2469 |
| Pro | Leu | Leu | Lys | Lys | Pro | Gly | Ala | Ala | Ser | Pro | Leu | Ala | Ser | Arg | Gln | |
| 770 | | | | | 775 | | | | | 780 | | | | | 785 | |
| AAC | ACG | CTG | CGG | AGC | TGT | GAT | CCG | GTG | TTC | TAT | AGG | CAG | GTG | TTG | GGT | 2517 |
| Asn | Thr | Leu | Arg | Ser | Cys | Asp | Pro | Val | Phe | Tyr | Arg | Gln | Val | Leu | Gly | |
| | | | | 790 | | | | | 795 | | | | | 800 | | |
| GCA | GAG | AGC | GCC | CCT | CCC | GGA | CAG | GTA | AGG | TTT | AGC | AAG | TCA | TGC | TTG | 2565 |
| Ala | Glu | Ser | Ala | Pro | Pro | Gly | Gln | Val | Arg | Phe | Ser | Lys | Ser | Cys | Leu | |
| | | | 805 | | | | | 810 | | | | | 815 | | | |
| ACC | CTG | TTA | GTG | CCT | TTT | TAT | TCC | TAC | ATC | ATA | TTG | AGA | AGG | CTG | GAG | 2613 |
| Thr | Leu | Leu | Val | Pro | Phe | Tyr | Ser | Tyr | Ile | Ile | Leu | Arg | Arg | Leu | Glu | |
| | | 820 | | | | | 825 | | | | | 830 | | | | |

```
CTG TTT TTT TAGTGATGAA GATGTTTTCC TGGTGATGCA TTCACACTTT                    2662
Leu Phe Phe
    835

CAACTGGCTC TTCCTAGATC AAAGTTAGTG CCTTTGTGAG ATGGTGGCCT GCCAGAGTGT          2722

GGTTTGTGGT CCCATTTCAG GGGGAAGATA CTTGACTCAT CTGTGGACCT AATTCACATC          2782

CTCAGCG                                                                    2789
```

(2) INFORMATION FOR SEQ ID NO:105:

(i) SEQUENCE CHARACTERISTICS:
        (A) LENGTH: 836 amino acids
        (B) TYPE: amino acid
        (D) TOPOLOGY: linear (ii) MOLECULE TYPE: protein (xi) SEQUENCE DESCRIPTION: SEQ ID NO:105:

```
Met Val Pro Glu Ala Trp Arg Ser Gly Leu Val Ser Thr Gly Arg Val
 1               5                  10                  15

Val Gly Val Leu Leu Leu Gly Ala Leu Asn Lys Ala Ser Thr Val
                20              25                  30

Ile His Tyr Glu Ile Pro Glu Glu Arg Glu Lys Gly Phe Ala Val Gly
            35                  40                  45

Asn Val Val Ala Asn Leu Gly Leu Asp Leu Gly Ser Leu Ser Ala Arg
        50                  55                  60

Arg Phe Pro Val Val Ser Gly Ala Ser Arg Arg Phe Phe Glu Val Asn
 65                 70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
               100                 105                 110

Glu Asn Pro Leu Glu Leu Phe Ser Val Glu Val Val Ile Gln Asp Ile
           115                 120                 125

Asn Asp Asn Asn Pro Ala Phe Pro Thr Gln Glu Met Lys Leu Glu Ile
       130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
                180                 185                 190

Tyr Ala Glu Leu Val Leu Glu Arg Ala Leu Asp Arg Glu Arg Glu Pro
            195                 200                 205

Ser Leu Gln Leu Val Leu Thr Ala Leu Asp Gly Gly Thr Pro Ala Leu
        210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
                260                 265                 270

Glu Gly Pro Asn Gly Glu Ile Ile Tyr Ser Phe Gly Ser His Asn Arg
            275                 280                 285

Ala Gly Val Arg Gln Leu Phe Ala Leu Asp Leu Val Thr Gly Met Leu
        290                 295                 300

Thr Ile Lys Gly Arg Leu Asp Phe Glu Asp Thr Lys Leu His Glu Ile
```

|     | 305 |     |     |     | 310 |     |     |     | 315 |     |     |     | 320 |
| --- | --- | --- | --- | --- | --- | --- | --- | --- | --- | --- | --- | --- | --- |

Tyr Ile Gln Ala Lys Asp Lys Gly Ala Asn Pro Glu Gly Ala His Cys
            325             330             335

Lys Val Leu Val Glu Val Val Asp Val Asn Asp Asn Ala Pro Glu Ile
            340             345             350

Thr Val Thr Ser Val Tyr Ser Pro Val Pro Glu Asp Ala Ser Gly Thr
            355             360             365

Val Ile Ala Leu Leu Ser Val Thr Asp Leu Asp Ala Gly Glu Asn Gly
    370             375             380

Leu Val Thr Cys Glu Val Pro Pro Gly Leu Pro Phe Ser Leu Thr Ser
385             390             395             400

Ser Leu Lys Asn Tyr Phe Thr Leu Lys Thr Ser Ala Asp Leu Asp Arg
            405             410             415

Glu Thr Val Pro Glu Tyr Asn Leu Ser Ile Thr Ala Arg Asp Ala Gly
            420             425             430

Thr Pro Ser Leu Ser Ala Leu Thr Ile Val Arg Val Gln Val Ser Asp
            435             440             445

Ile Asn Asp Asn Pro Pro Gln Ser Ser Gln Ser Ser Tyr Asp Val Tyr
    450             455             460

Ile Glu Glu Asn Asn Leu Pro Gly Ala Pro Ile Leu Asn Leu Ser Val
465             470             475             480

Trp Asp Pro Asp Ala Pro Gln Asn Ala Arg Leu Ser Phe Phe Leu Leu
            485             490             495

Glu Gln Gly Ala Glu Thr Gly Leu Val Gly Arg Tyr Phe Thr Ile Asn
            500             505             510

Arg Asp Asn Gly Ile Val Ser Ser Leu Val Pro Leu Asp Tyr Glu Asp
            515             520             525

Arg Arg Glu Phe Glu Leu Thr Ala His Ile Ser Asp Gly Gly Thr Pro
    530             535             540

Val Leu Ala Thr Asn Ile Ser Val Asn Ile Phe Val Thr Asp Arg Asn
545             550             555             560

Asp Asn Ala Pro Gln Val Leu Tyr Pro Arg Pro Gly Gly Ser Ser Val
            565             570             575

Glu Met Leu Pro Arg Gly Thr Ser Ala Gly His Leu Val Ser Arg Val
            580             585             590

Val Gly Trp Asp Ala Asp Ala Gly His Asn Ala Trp Leu Ser Tyr Ser
        595             600             605

Leu Phe Gly Ser Pro Asn Gln Ser Leu Phe Ala Ile Gly Leu His Thr
    610             615             620

Gly Gln Ile Ser Thr Ala Arg Pro Val Gln Asp Thr Asp Ser Pro Arg
625             630             635             640

Gln Thr Leu Thr Val Leu Ile Lys Asp Asn Gly Glu Pro Ser Leu Ser
            645             650             655

Thr Thr Ala Thr Leu Thr Val Ser Val Thr Glu Asp Ser Pro Glu Ala
            660             665             670

Arg Ala Glu Phe Pro Ser Gly Ser Ala Pro Arg Glu Gln Lys Lys Asn
            675             680             685

Leu Thr Phe Tyr Leu Leu Leu Ser Leu Ile Leu Val Ser Val Gly Phe
    690             695             700

Val Val Thr Val Phe Gly Val Ile Ile Phe Lys Val Tyr Lys Trp Lys
705             710             715             720

Gln Ser Arg Asp Leu Tyr Arg Ala Pro Val Ser Ser Leu Tyr Arg Thr
            725             730             735

| | | | | | | | | | | | | | | | |
|---|---|---|---|---|---|---|---|---|---|---|---|---|---|---|---|
| Pro | Gly | Pro | Ser<br>740 | Leu | His | Ala | Asp | Ala<br>745 | Val | Arg | Gly | Gly | Leu<br>750 | Met | Ser |
| Pro | His | Leu<br>755 | Tyr | His | Gln | Val | Tyr<br>760 | Leu | Thr | Thr | Asp | Ser<br>765 | Arg | Arg | Ser |
| Asp | Pro<br>770 | Leu | Leu | Lys | Lys | Pro<br>775 | Gly | Ala | Ala | Ser | Pro<br>780 | Leu | Ala | Ser | Arg |
| Gln<br>785 | Asn | Thr | Leu | Arg | Ser<br>790 | Cys | Asp | Pro | Val | Phe<br>795 | Tyr | Arg | Gln | Val | Leu<br>800 |
| Gly | Ala | Glu | Ser | Ala<br>805 | Pro | Pro | Gly | Gln | Val<br>810 | Arg | Phe | Ser | Lys | Ser<br>815 | Cys |
| Leu | Thr | Leu | Leu<br>820 | Val | Pro | Phe | Tyr | Ser<br>825 | Tyr | Ile | Ile | Leu | Arg<br>830 | Arg | Leu |
| Glu | Leu | Phe<br>835 | Phe | | | | | | | | | | | | |

( 2 ) INFORMATION FOR SEQ ID NO:106:

( i ) SEQUENCE CHARACTERISTICS:
        ( A ) LENGTH: 2751 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2160

( x i ) SEQUENCE DESCRIPTION: SEQ ID NO:106:

| | | | | | |
|---|---|---|---|---|---|
| CGAAAGCCAT | GTCGGACTCG | TCGCCCAGCG | CCCAAGCGCT | AACCCGCTGA | AAGTTTCTCA | 60 |
| GCGAAATCTC | AGGGACGATC | TGGACCCCGC | TGAGAGGAAC | TGCTTTTGAG | TGAG ATG<br>Met<br>1 | 117 |

| | | | | | | | | | | | | | | | | |
|---|---|---|---|---|---|---|---|---|---|---|---|---|---|---|---|---|
| GTC | CCA | GAG | GCC | TGG | AGG | AGC | GGA | CTG | GTA | AGC | ACC | GGG | AGG | GTA | GTG | 165 |
| Val | Pro | Glu | Ala<br>5 | Trp | Arg | Ser | Gly | Leu<br>10 | Val | Ser | Thr | Gly | Arg<br>15 | Val | Val | |
| GGA | GTT | TTG | CTT | CTG | CTT | GGT | GCC | TTG | AAC | AAG | GCT | TCC | ACG | GTC | ATT | 213 |
| Gly | Val | Leu<br>20 | Leu | Leu | Leu | Gly | Ala<br>25 | Leu | Asn | Lys | Ala | Ser<br>30 | Thr | Val | Ile | |
| CAC | TAT | GAG | ATC | CCG | GAG | GAA | AGA | GAG | AAG | GGT | TTC | GCT | GTG | GGC | AAC | 261 |
| His | Tyr<br>35 | Glu | Ile | Pro | Glu | Glu<br>40 | Arg | Glu | Lys | Gly | Phe<br>45 | Ala | Val | Gly | Asn | |
| GTG | GTC | GCG | AAC | CTT | GGT | TTG | GAT | CTC | GGT | AGC | CTC | TCA | GCC | CGC | AGG | 309 |
| Val<br>50 | Val | Ala | Asn | Leu | Gly<br>55 | Leu | Asp | Leu | Gly | Ser<br>60 | Leu | Ser | Ala | Arg | Arg<br>65 | |
| TTC | CCG | GTG | GTG | TCT | GGA | GCT | AGC | CGA | AGA | TTC | TTT | GAG | GTG | AAC | CGG | 357 |
| Phe | Pro | Val | Val | Ser<br>70 | Gly | Ala | Ser | Arg | Arg<br>75 | Phe | Phe | Glu | Val | Asn<br>80 | Arg | |
| GAG | ACC | GGA | GAG | ATG | TTT | GTG | AAC | GAC | CGT | CTG | GAT | CGA | GAG | GAG | CTG | 405 |
| Glu | Thr | Gly | Glu | Met<br>85 | Phe | Val | Asn | Asp | Arg<br>90 | Leu | Asp | Arg | Glu | Glu<br>95 | Leu | |
| TGT | GGG | ACA | CTG | CCC | TCT | TGC | ACT | GTA | ACT | CTG | GAG | TTG | GTA | GTG | GAG | 453 |
| Cys | Gly | Thr<br>100 | Leu | Pro | Ser | Cys | Thr<br>105 | Val | Thr | Leu | Glu | Leu<br>110 | Val | Val | Glu | |
| AAC | CCG | CTG | GAG | CTG | TTC | AGC | GTG | GAA | GTG | GTG | ATC | CAG | GAC | ATC | AAC | 501 |
| Asn | Pro<br>115 | Leu | Glu | Leu | Phe | Ser<br>120 | Val | Glu | Val | Val | Ile<br>125 | Gln | Asp | Ile | Asn | |
| GAC | AAC | AAT | CCT | GCT | TTC | CCT | ACC | CAG | GAA | ATG | AAA | TTG | GAG | ATT | AGC | 549 |
| Asp<br>130 | Asn | Asn | Pro | Ala | Phe<br>135 | Pro | Thr | Gln | Glu | Met<br>140 | Lys | Leu | Glu | Ile | Ser<br>145 | |

```
GAG GCC GTG GCT CCG GGG ACG CGC TTT CCG CTC GAG AGC GCG CAC GAT         597
Glu Ala Val Ala Pro Gly Thr Arg Phe Pro Leu Glu Ser Ala His Asp
            150                 155                 160

CCC GAT CTG GGA AGC AAC TCT TTA CAA ACC TAT GAG CTG AGC CGA AAT         645
Pro Asp Leu Gly Ser Asn Ser Leu Gln Thr Tyr Glu Leu Ser Arg Asn
            165                 170                 175

GAA TAC TTT GCG CTT CGC GTG CAG ACG CGG GAG GAC AGC ACC AAG TAC         693
Glu Tyr Phe Ala Leu Arg Val Gln Thr Arg Glu Asp Ser Thr Lys Tyr
            180                 185                 190

GCG GAG CTG GTG TTG GAG CGC GCC CTG GAC CGA GAA CGG GAG CCT AGT         741
Ala Glu Leu Val Leu Glu Arg Ala Leu Asp Arg Glu Arg Glu Pro Ser
    195                 200                 205

CTC CAG TTA GTG CTG ACG GCG TTG GAC GGA GGG ACC CCA GCT CTC TCC         789
Leu Gln Leu Val Leu Thr Ala Leu Asp Gly Gly Thr Pro Ala Leu Ser
210                 215                 220                 225

GCC AGC CTG CCT ATT CAC ATC AAG GTG CTG GAC GCG AAT GAC AAT GCG         837
Ala Ser Leu Pro Ile His Ile Lys Val Leu Asp Ala Asn Asp Asn Ala
                    230                 235                 240

CCT GTC TTC AAC CAG TCC TTG TAC CGG GCG CGC GTT CCT GGA GGA TGC         885
Pro Val Phe Asn Gln Ser Leu Tyr Arg Ala Arg Val Pro Gly Gly Cys
                245                 250                 255

ACC TCC GGC ACG CGC GTG GTA CAA GTC CTT GCA ACG GAT CTG GAT GAA         933
Thr Ser Gly Thr Arg Val Val Gln Val Leu Ala Thr Asp Leu Asp Glu
        260                 265                 270

GGC CCC AAC GGT GAA ATT ATT TAC TCC TTC GGC AGC CAC AAC CGC GCC         981
Gly Pro Asn Gly Glu Ile Ile Tyr Ser Phe Gly Ser His Asn Arg Ala
275                 280                 285

GGC GTG CGG CAA CTA TTC GCC TTA GAC CTT GTA ACC GGG ATG CTG ACA        1029
Gly Val Arg Gln Leu Phe Ala Leu Asp Leu Val Thr Gly Met Leu Thr
290                 295                 300                 305

ATC AAG GGT CGG CTG GAC TTC GAG GAC ACC AAA CTC CAT GAG ATT TAC        1077
Ile Lys Gly Arg Leu Asp Phe Glu Asp Thr Lys Leu His Glu Ile Tyr
                310                 315                 320

ATC CAG GCC AAA GAC AAG GGC GCC AAT CCC GAA GGA GCA CAT TGC AAA        1125
Ile Gln Ala Lys Asp Lys Gly Ala Asn Pro Glu Gly Ala His Cys Lys
                325                 330                 335

GTG TTG GTG GAG GTT GTG GAT GTG AAT GAC AAC GCC CCG GAG ATC ACA        1173
Val Leu Val Glu Val Val Asp Val Asn Asp Asn Ala Pro Glu Ile Thr
        340                 345                 350

GTC ACC TCC GTG TAC AGC CCA GTA CCC GAG GAT GCC TCT GGG ACT GTC        1221
Val Thr Ser Val Tyr Ser Pro Val Pro Glu Asp Ala Ser Gly Thr Val
    355                 360                 365

ATC GCT TTG CTC AGT GTG ACT GAC CTG GAT GCT GGC GAG AAC GGG CTG        1269
Ile Ala Leu Leu Ser Val Thr Asp Leu Asp Ala Gly Glu Asn Gly Leu
370                 375                 380                 385

GTG ACC TGC GAA GTT CCA CCG GGT CTC CCT TTC AGC CTT ACT TCT TCC        1317
Val Thr Cys Glu Val Pro Pro Gly Leu Pro Phe Ser Leu Thr Ser Ser
                390                 395                 400

CTC AAG AAT TAC TTC ACT TTG AAA ACC AGT GCA GAC CTG GAT CGG GAG        1365
Leu Lys Asn Tyr Phe Thr Leu Lys Thr Ser Ala Asp Leu Asp Arg Glu
                405                 410                 415

ACT GTG CCA GAA TAC AAC CTC AGC ATC ACC GCC CGA GAC GCC GGA ACC        1413
Thr Val Pro Glu Tyr Asn Leu Ser Ile Thr Ala Arg Asp Ala Gly Thr
        420                 425                 430

CCT TCC CTC TCA GCC CTT ACA ATA GTG CGT GTT CAA GTG TCC GAC ATC        1461
Pro Ser Leu Ser Ala Leu Thr Ile Val Arg Val Gln Val Ser Asp Ile
    435                 440                 445

AAT GAC AAC CCT CCA CAA TCT TCT CAA TCT TCC TAC GAC GTT TAC ATT        1509
Asn Asp Asn Pro Pro Gln Ser Ser Gln Ser Ser Tyr Asp Val Tyr Ile
450                 455                 460                 465
```

| | | | | | | | | | | | | | | | | |
|---|---|---|---|---|---|---|---|---|---|---|---|---|---|---|---|---|
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu | Pro | Gly | Ala | Pro | Ile | Leu | Asn | Leu | Ser | Val | Trp | |
| | | | | 470 | | | | | 475 | | | | | 480 | | |
| GAC | CCC | GAC | GCC | CCG | CAG | AAT | GCT | CGG | CTT | TCT | TTC | TTT | CTC | TTG | GAG | 1605 |
| Asp | Pro | Asp | Ala | Pro | Gln | Asn | Ala | Arg | Leu | Ser | Phe | Phe | Leu | Leu | Glu | |
| | | | 485 | | | | | 490 | | | | | 495 | | | |
| CAA | GGA | GCT | GAA | ACC | GGG | CTA | GTG | GGT | CGC | TAT | TTC | ACA | ATA | AAT | CGT | 1653 |
| Gln | Gly | Ala | Glu | Thr | Gly | Leu | Val | Gly | Arg | Tyr | Phe | Thr | Ile | Asn | Arg | |
| | | | 500 | | | | 505 | | | | | 510 | | | | |
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg | |
| | 515 | | | | 520 | | | | | 525 | | | | | | |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val | |
| 530 | | | | | 535 | | | | | 540 | | | | | 545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp | |
| | | | | 550 | | | | | 555 | | | | | 560 | | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu | |
| | | | 565 | | | | | 570 | | | | | 575 | | | |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val | |
| | | 580 | | | | | 585 | | | | | 590 | | | | |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu | |
| | 595 | | | | | 600 | | | | | 605 | | | | | |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly | |
| 610 | | | | | 615 | | | | | 620 | | | | | 625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln | |
| | | | | 630 | | | | | 635 | | | | | 640 | | |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr | |
| | | | 645 | | | | | 650 | | | | | 655 | | | |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg | |
| | | 660 | | | | | 665 | | | | | 670 | | | | |
| GCC | GAG | TTC | CCC | TCT | GGC | TCT | GCC | AGT | TAAACCTTCT | TTAATTATGG | | | | | | 2180 |
| Ala | Glu | Phe | Pro | Ser | Gly | Ser | Ala | Ser | | | | | | | | |
| | 675 | | | | | 680 | | | | | | | | | | |

| | | | | |
|---|---|---|---|---|
| ATTAGCCATT | AACATTTTTG | AAACGTGGAC | CATTTAACCT | CGGCCTACCC | CCTCCAACTG | 2240 |
| TCCTGGTGAT | GAGTTCATTA | GCTAAGTTAA | ATTAATTGAA | CTTTGATCTA | AACCAAAACA | 2300 |
| AATCAGGAAA | ATAAAGCTGT | AAAGGAACTT | ATCAAGCATT | CCAAAACCAA | CTAGAAATTA | 2360 |
| CTTGAAGTTT | CGAGTGAGCA | TTGCCTGTGC | CAGTATTCTT | CATTATAGGA | TTATAAACTC | 2420 |
| GTTTTTTTCC | CAAAGCGCAT | GTCTACGCCA | GGCAGAGGAG | TAATTATTCA | GCCAATTTCA | 2480 |
| TGGATGTAAC | GATGGATATA | AATAATTGAT | AGCACCTAGA | GGCTTCCAGT | TTGGGTGGAA | 2540 |
| GGCTAAAAGT | AGAGGGGAAC | TCACTCACTT | GAGAAATGAT | ATTTAAGTGA | ATAAATAGTT | 2600 |
| CTCTTCTATG | AAACTATTAC | TATTTAGTTC | TCTGGAAAAC | TTAAGTGTAT | TAATGATTAG | 2660 |
| AACATCAAAT | CCTAAGTAAA | GAAATGACAT | TTTAAATATA | AAAGCCAAA | CTTTAAATAA | 2720 |
| ATCATAGAGA | CCTCAGACAT | AATATAGGAA | A | | | 2751 |

( 2 ) INFORMATION FOR SEQ ID NO:107:

( i ) SEQUENCE CHARACTERISTICS:

( A ) LENGTH: 682 amino acids
( B ) TYPE: amino acid
( D ) TOPOLOGY: linear ( i i ) MOLECULE TYPE: protein ( x i ) SEQUENCE DESCRIPTION: SEQ ID NO:107:

| Met | Val | Pro | Glu | Ala | Trp | Arg | Ser | Gly | Leu | Val | Ser | Thr | Gly | Arg | Val |
|---|---|---|---|---|---|---|---|---|---|---|---|---|---|---|---|
| 1 | | | | 5 | | | | | 10 | | | | | 15 | |
| Val | Gly | Val | Leu | Leu | Leu | Gly | Ala | Leu | Asn | Lys | Ala | Ser | Thr | Val | |
| | | | 20 | | | | 25 | | | | | 30 | | | |
| Ile | His | Tyr | Glu | Ile | Pro | Glu | Glu | Arg | Glu | Lys | Gly | Phe | Ala | Val | Gly |
| | | 35 | | | | 40 | | | | | | 45 | | | |
| Asn | Val | Val | Ala | Asn | Leu | Gly | Leu | Asp | Leu | Gly | Ser | Leu | Ser | Ala | Arg |
| | 50 | | | | | 55 | | | | | 60 | | | | |
| Arg | Phe | Pro | Val | Val | Ser | Gly | Ala | Ser | Arg | Arg | Phe | Phe | Glu | Val | Asn |
| 65 | | | | | 70 | | | | 75 | | | | | | 80 |
| Arg | Glu | Thr | Gly | Glu | Met | Phe | Val | Asn | Asp | Arg | Leu | Asp | Arg | Glu | Glu |
| | | | | 85 | | | | | 90 | | | | | 95 | |
| Leu | Cys | Gly | Thr | Leu | Pro | Ser | Cys | Thr | Val | Thr | Leu | Glu | Leu | Val | Val |
| | | | 100 | | | | | 105 | | | | | 110 | | |
| Glu | Asn | Pro | Leu | Glu | Leu | Phe | Ser | Val | Glu | Val | Val | Ile | Gln | Asp | Ile |
| | | | 115 | | | | | 120 | | | | 125 | | | |
| Asn | Asp | Asn | Asn | Pro | Ala | Phe | Pro | Thr | Gln | Glu | Met | Lys | Leu | Glu | Ile |
| | 130 | | | | | 135 | | | | | 140 | | | | |
| Ser | Glu | Ala | Val | Ala | Pro | Gly | Thr | Arg | Phe | Pro | Leu | Glu | Ser | Ala | His |
| 145 | | | | | 150 | | | | | 155 | | | | | 160 |
| Asp | Pro | Asp | Leu | Gly | Ser | Asn | Ser | Leu | Gln | Thr | Tyr | Glu | Leu | Ser | Arg |
| | | | | 165 | | | | | 170 | | | | | 175 | |
| Asn | Glu | Tyr | Phe | Ala | Leu | Arg | Val | Gln | Thr | Arg | Glu | Asp | Ser | Thr | Lys |
| | | | 180 | | | | | 185 | | | | | 190 | | |
| Tyr | Ala | Glu | Leu | Val | Leu | Glu | Arg | Ala | Leu | Asp | Arg | Glu | Arg | Glu | Pro |
| | | 195 | | | | | 200 | | | | | 205 | | | |
| Ser | Leu | Gln | Leu | Val | Leu | Thr | Ala | Leu | Asp | Gly | Gly | Thr | Pro | Ala | Leu |
| | 210 | | | | | 215 | | | | | 220 | | | | |
| Ser | Ala | Ser | Leu | Pro | Ile | His | Ile | Lys | Val | Leu | Asp | Ala | Asn | Asp | Asn |
| 225 | | | | | 230 | | | | | 235 | | | | | 240 |
| Ala | Pro | Val | Phe | Asn | Gln | Ser | Leu | Tyr | Arg | Ala | Arg | Val | Pro | Gly | Gly |
| | | | | 245 | | | | | 250 | | | | | 255 | |
| Cys | Thr | Ser | Gly | Thr | Arg | Val | Val | Gln | Val | Leu | Ala | Thr | Asp | Leu | Asp |
| | | | 260 | | | | | 265 | | | | | 270 | | |
| Glu | Gly | Pro | Asn | Gly | Glu | Ile | Ile | Tyr | Ser | Phe | Gly | Ser | His | Asn | Arg |
| | | 275 | | | | | 280 | | | | | 285 | | | |
| Ala | Gly | Val | Arg | Gln | Leu | Phe | Ala | Leu | Asp | Leu | Val | Thr | Gly | Met | Leu |
| | 290 | | | | | 295 | | | | | 300 | | | | |
| Thr | Ile | Lys | Gly | Arg | Leu | Asp | Phe | Glu | Asp | Thr | Lys | Leu | His | Glu | Ile |
| 305 | | | | | 310 | | | | | 315 | | | | | 320 |
| Tyr | Ile | Gln | Ala | Lys | Asp | Lys | Gly | Ala | Asn | Pro | Glu | Gly | Ala | His | Cys |
| | | | | 325 | | | | | 330 | | | | | 335 | |
| Lys | Val | Leu | Val | Glu | Val | Val | Asp | Val | Asn | Asp | Asn | Ala | Pro | Glu | Ile |
| | | | 340 | | | | | 345 | | | | | 350 | | |
| Thr | Val | Thr | Ser | Val | Tyr | Ser | Pro | Val | Pro | Glu | Asp | Ala | Ser | Gly | Thr |
| | | 355 | | | | | 360 | | | | | 365 | | | |
| Val | Ile | Ala | Leu | Leu | Ser | Val | Thr | Asp | Leu | Asp | Ala | Gly | Glu | Asn | Gly |
| | 370 | | | | | 375 | | | | | 380 | | | | |

-continued

| | | | | | | | | | | | | | | |
|---|---|---|---|---|---|---|---|---|---|---|---|---|---|---|
| Leu 385 | Val | Thr | Cys | Glu | Val 390 | Pro | Pro | Gly | Leu | Pro 395 | Phe | Ser | Leu | Thr | Ser 400 |
| Ser | Leu | Lys | Asn | Tyr 405 | Phe | Thr | Leu | Lys | Thr 410 | Ser | Ala | Asp | Leu | Asp 415 | Arg |
| Glu | Thr | Val | Pro 420 | Glu | Tyr | Asn | Leu | Ser 425 | Ile | Thr | Ala | Arg | Asp 430 | Ala | Gly |
| Thr | Pro | Ser 435 | Leu | Ser | Ala | Leu | Thr 440 | Ile | Val | Arg | Val | Gln 445 | Val | Ser | Asp |
| Ile | Asn 450 | Asp | Asn | Pro | Pro | Gln 455 | Ser | Ser | Gln | Ser | Ser 460 | Tyr | Asp | Val | Tyr |
| Ile 465 | Glu | Glu | Asn | Asn | Leu 470 | Pro | Gly | Ala | Pro | Ile 475 | Leu | Asn | Leu | Ser | Val 480 |
| Trp | Asp | Pro | Asp | Ala 485 | Pro | Gln | Asn | Ala | Arg 490 | Leu | Ser | Phe | Phe | Leu 495 | Leu |
| Glu | Gln | Gly | Ala 500 | Glu | Thr | Gly | Leu | Val 505 | Gly | Arg | Tyr | Phe | Thr 510 | Ile | Asn |
| Arg | Asp | Asn 515 | Gly | Ile | Val | Ser | Ser 520 | Leu | Val | Pro | Leu | Asp 525 | Tyr | Glu | Asp |
| Arg | Arg 530 | Glu | Phe | Glu | Leu | Thr 535 | Ala | His | Ile | Ser | Asp 540 | Gly | Gly | Thr | Pro |
| Val 545 | Leu | Ala | Thr | Asn | Ile 550 | Ser | Val | Asn | Ile | Phe 555 | Val | Thr | Asp | Arg | Asn 560 |
| Asp | Asn | Ala | Pro | Gln 565 | Val | Leu | Tyr | Pro | Arg 570 | Pro | Gly | Gly | Ser | Ser 575 | Val |
| Glu | Met | Leu | Pro 580 | Arg | Gly | Thr | Ser | Ala 585 | Gly | His | Leu | Val | Ser 590 | Arg | Val |
| Val | Gly | Trp 595 | Asp | Ala | Asp | Ala | Gly 600 | His | Asn | Ala | Trp | Leu 605 | Ser | Tyr | Ser |
| Leu | Phe 610 | Gly | Ser | Pro | Asn | Gln 615 | Ser | Leu | Phe | Ala | Ile 620 | Gly | Leu | His | Thr |
| Gly 625 | Gln | Ile | Ser | Thr | Ala 630 | Arg | Pro | Val | Gln | Asp 635 | Thr | Asp | Ser | Pro | Arg 640 |
| Gln | Thr | Leu | Thr | Val 645 | Leu | Ile | Lys | Asp | Asn 650 | Gly | Glu | Pro | Ser | Leu 655 | Ser |
| Thr | Thr | Ala | Thr 660 | Leu | Thr | Val | Ser | Val 665 | Thr | Glu | Asp | Ser | Pro 670 | Glu | Ala |
| Arg | Ala | Glu 675 | Phe | Pro | Ser | Gly | Ser 680 | Ala | Ser | | | | | | |